(12) United States Patent
Henderson et al.

(10) Patent No.: US 6,432,700 B1
(45) Date of Patent: *Aug. 13, 2002

(54) ADENOVIRUS VECTORS CONTAINING HETEROLOGOUS TRANSCRIPTION REGULATORY ELEMENTS AND METHODS OF USING SAME

(75) Inventors: Daniel R. Henderson, Palo Alto; De-Chao Yu, Foster City, both of CA (US)

(73) Assignee: Cell Genesys, Inc., Foster City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/033,556

(22) Filed: Mar. 2, 1998

Related U.S. Application Data

(60) Provisional application No. 60/039,597, filed on Mar. 3, 1997, provisional application No. 60/039,762, filed on Mar. 3, 1997, provisional application No. 60/039,763, filed on Mar. 3, 1997, and provisional application No. 60/054,523, filed on Aug. 4, 1997.

(51) Int. Cl.[7] .............................................. C12N 15/00
(52) U.S. Cl. .................. 435/320.1; 424/93.2; 424/93.6; 424/199.1; 424/204.1; 424/233.1; 435/252.3; 514/44; 536/23.1; 536/23.4; 536/23.72; 536/24.1
(58) Field of Search .............................. 424/93.2, 93.6, 424/199.1, 204.1, 233.1; 435/5, 172.3, 252.3, 320.1, 325, 455, 456; 514/44; 536/23.1, 23.4, 23.72, 24.1; 935/57, 65

(56) References Cited

U.S. PATENT DOCUMENTS 5,698,443 A * 12/1997 Henderson et al. ...... 435/320.1
5,998,205 A * 12/1999 Hallenbeck et al. ......... 435/325
6,197,293 B1 * 3/2001 Henderson et al. ......... 424/93.2

FOREIGN PATENT DOCUMENTS

WO 96-17053 A1 * 6/1996
WO 96-34969 A2 * 11/1996

* cited by examiner

*Primary Examiner*—Jeffrey Stucker
*Assistant Examiner*—Ulrike Winkler
(74) *Attorney, Agent, or Firm*—Linda R. Judge; Pamela J. Sherwood; Bozicevic, Field & Francis LLP

(57) ABSTRACT

Replication-competent adenovirus vectors specific for target cells and methods of use of such viruses are provided. These adenoviruses comprise a first adenoviral gene under control of a cell specific heterologous (i.e., non-adenoviral) transcriptional regulatory element (TRE) and at least a second gene under control of a second heterologous TRE, where the heterologous TREs are different from each other in polynucleotide sequence but functional in the same cell. The adenoviral gene can be, for example, a gene required for adenoviral replication. The second gene can be, for example, a second adenoviral gene or a transgene, such as a gene which can contribute to cytotoxicity in the target cell. Adenoviral replication can be restricted to target cells in which the heterologous TREs are functional and thus, the adenovirus vectors can provide selective cytotoxicity to the target cells, particularly neoplastic cells.

17 Claims, 15 Drawing Sheets

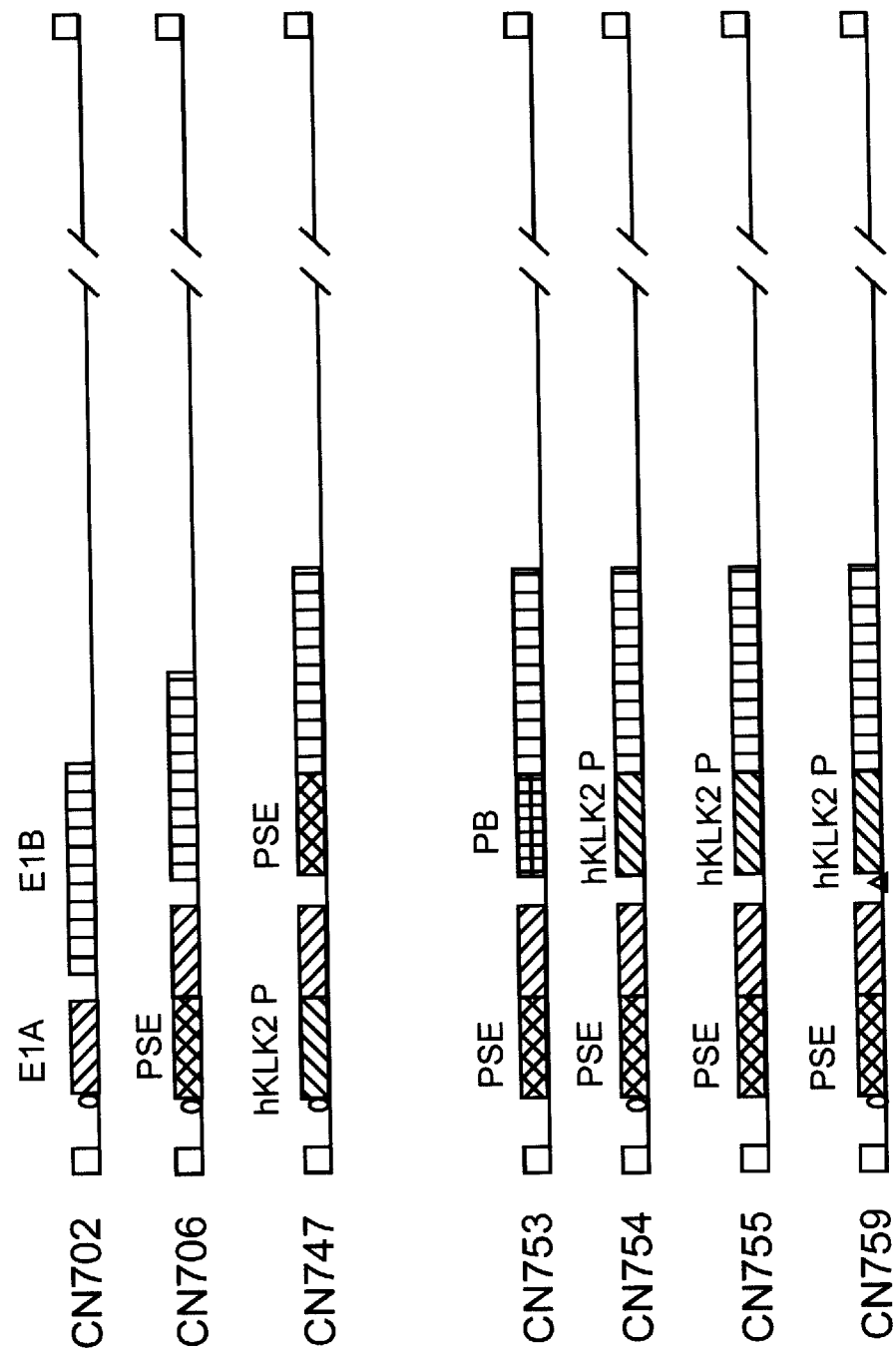

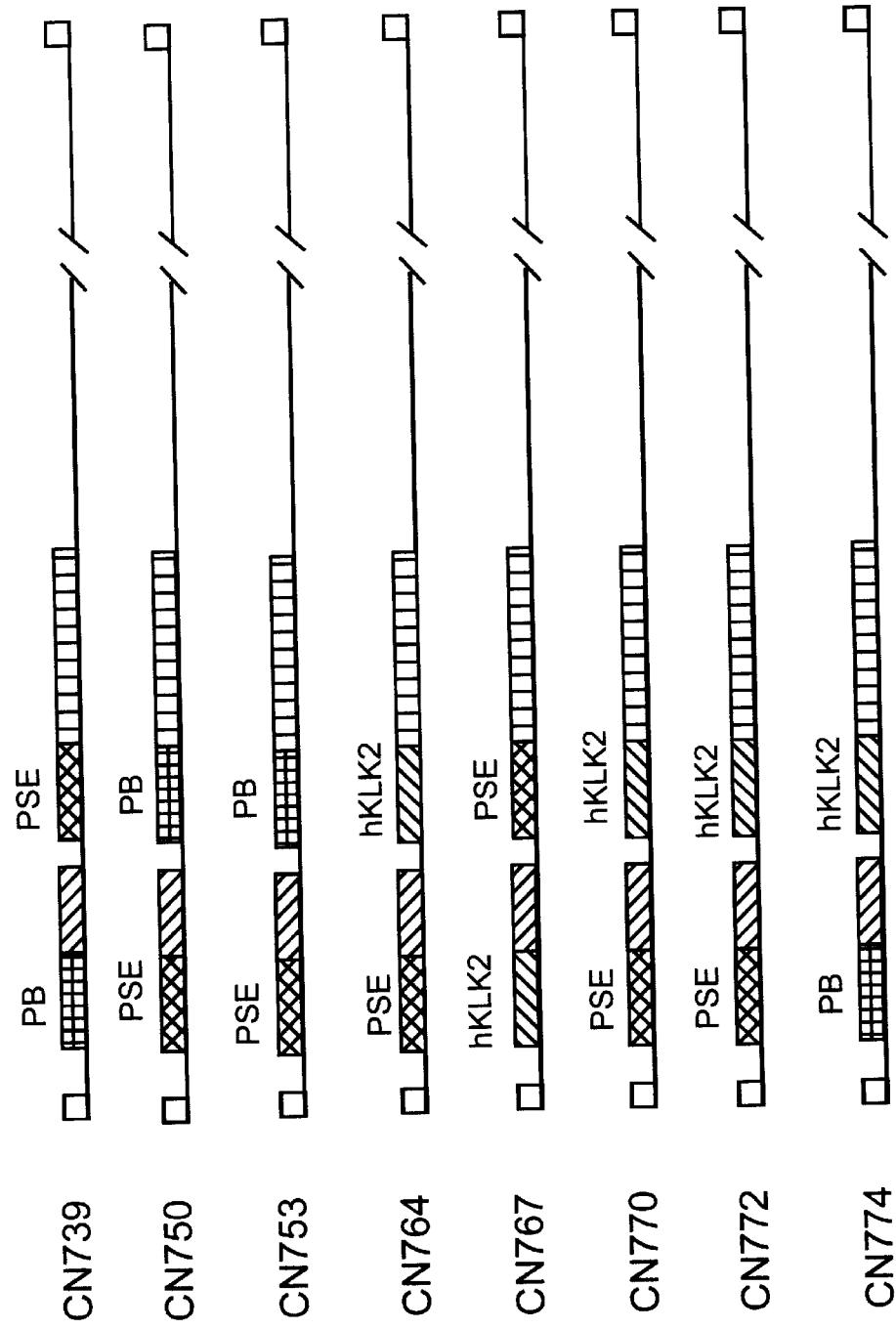

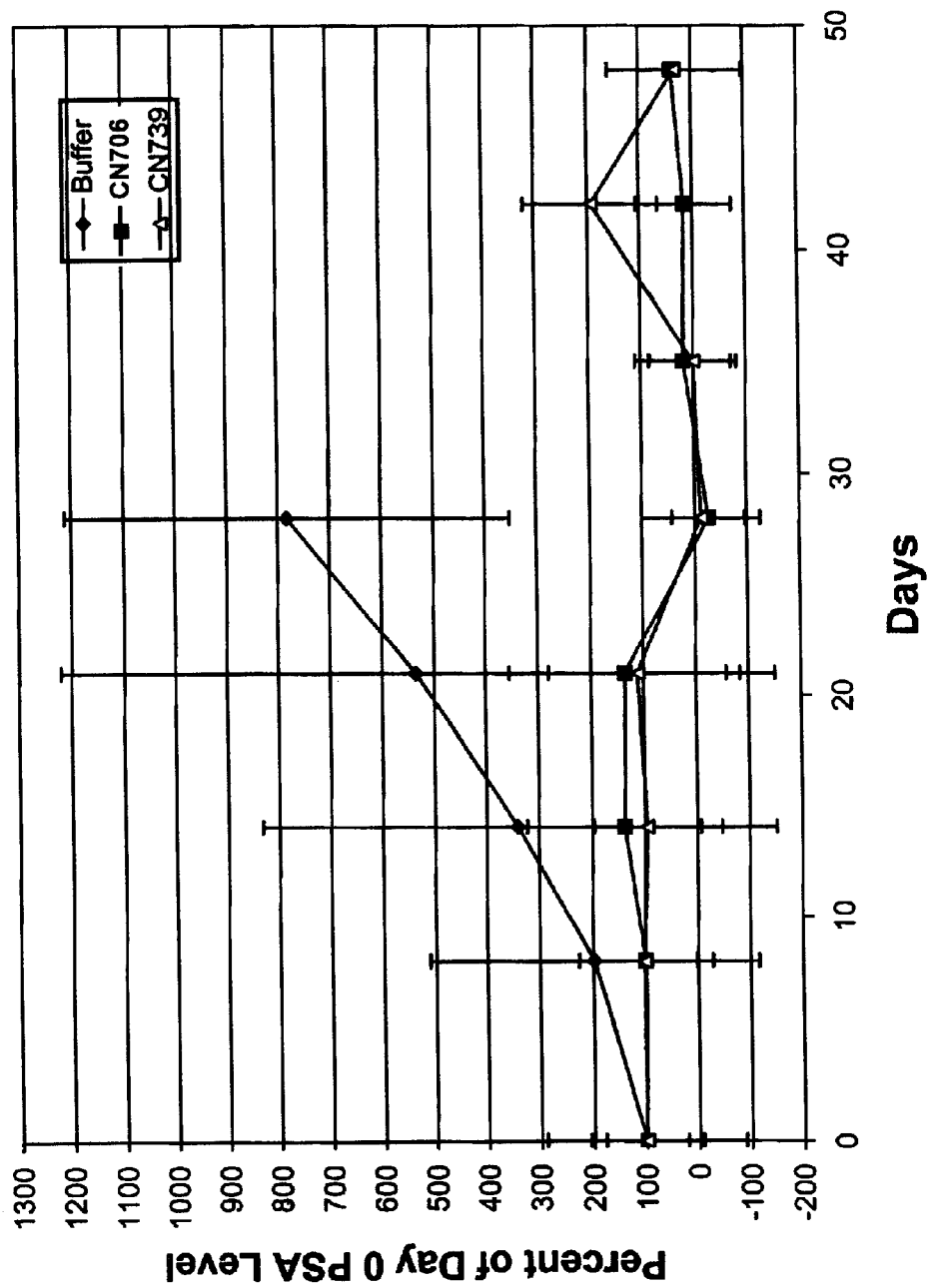

Cytoxity of Ad Viral Vectors in LNCaP Cells

Extracellular Virus Yield in Ad Infected A549 Cells

Note: Buffer treated animals were sacrificed after four weeks because of excessive tumor burden

ADENOVIRUS VECTORS CONTAINING HETEROLOGOUS TRANSCRIPTION REGULATORY ELEMENTS AND METHODS OF USING SAME

CROSS-REFERENCE TO RELATED APPLICATIONS

This application claims the benefit of U.S. Ser. No. 60/039,597 filed Mar. 3, 1997; U.S. Serial No. 60/039,762, filed Mar. 3, 1997; U.S. Ser. No. 60/039,763, filed Mar. 3, 1997; and U.S. Ser. No. 60/054,523, filed Aug. 4, 1997.

STATEMENT OF RIGHTS TO INVENTIONS MADE UNDER FEDERALLY SPONSORED RESEARCH (Not applicable).

TECHNICAL FIELD

This invention relates to cell transfection using adenovirus vectors, providing replication-competent adenovirus vectors and methods of their use. More specifically, it relates to cell-specific replication of adenovirus vectors in cells through the use of cell-specific, non-adenoviral transcriptional regulatory elements.

BACKGROUND ART

In spite of numerous advances in medical research, cancer remains the second leading cause of death in the United States. In the industrialized nations, roughly one in five persons will die of cancer. Traditional modes of clinical care, such as surgical resection, radiotherapy and chemotherapy, have a significant failure rate, especially for solid tumors. Neoplasia resulting in benign tumors can usually be completely cured by removing the mass surgically. If a tumor becomes malignant, as manifested by invasion of surrounding tissue, it becomes much more difficult to eradicate. Once a malignant tumor metastasizes, it is much less likely to be eradicated.

Excluding basal cell carcinoma, there are over one million new cases of cancer per year in the United States alone, and cancer accounts for over one half million deaths per year in this country. In the world as a whole, the five most common cancers are those of lung, stomach, breast, colon/rectum, and uterine cervix, and the total number of new cases per year is over 6 million.

Lung cancer is one of the most refractory of solid tumors because inoperable cases are up to 60% and the 5-year survival is only 13%. In particular, adenocarcinomas, which comprise about one-half of the total lung cancer cases, are mostly chemo-radioresistant. Gastric (i.e., stomach) carcinoma is one of the most prevalent forms of cancers in East Asia, including Japan and Korea. Although extensive surgical operations have been combined with chemotherapy and immunotherapy, the mortality of gastric cancer is still high, due to carcinomatous peritonitis and liver metastasis at advanced stages. Colorectal cancer is the third most common cancer and the second leading cause of cancer deaths. Pancreatic cancer is virtually always fatal. Thus, current treatment prospects for many patients with these carcinomas are unsatisfactory, and the prognosis is poor.

Hepatocellular carcinoma (HCC or malignant hepatoma) is one of the most common cancers in the world, and is especially problematic in Asia. Treatment prospects for patients with hepatocellular carcinoma are dim. Even with improvements in therapy and availability of liver transplant, only a minority of patients are cured by removal of the tumor either by resection or transplantation. For the majority of patients, the current treatments remain unsatisfactory, and the prognosis is poor.

Breast cancer is one of the most common cancers in the United States, with an annual incidence of about 182,000 new cases and nearly 50,000 deaths. In the industrial nations, approximately one in eight women can expect to develop breast cancer. The mortality rate for breast cancer has remained unchanged since 1930. It has increased an average of 0.2% per year, but decreased in women under 65 years of age by an average of 0.3% per year. See e.g., Marchant (1994) Contemporary Management of Breast Disease II: Breast Cancer, in: *Obstetrics and Gynecology Clinics of North America* 21:555–560; and Colditz (1993) *Cancer Suppl.* 71:1480–1489.

Despite ongoing improvement in the understanding of the disease, breast cancer has remained resistant to medical intervention. Most clinical initiatives are focused on early diagnosis, followed by conventional forms of intervention, particularly surgery and chemotherapy. Such interventions are of limited success, particularly in patients where the tumor has undergone metastasis. There is a pressing need to improve the arsenal of therapies available to provide more precise and more effective treatment in a less invasive way.

Prostate cancer is the fastest growing neoplasm in men with an estimated 244,000 new cases in the United States being diagnosed in 1995, of which approximately 44,000 deaths will result. Prostate cancer is now the most frequently diagnosed cancer in men. Prostate cancer is latent; many men carry prostate cancer cells without overt signs of disease. It is associated with a high morbidity. Cancer metastasis to bone (late stage) is common and is almost always fatal.

Current treatments include radical prostatectomy, radiation therapy, hormonal ablation and chemotherapy. Unfortunately, in approximately 80% of cases, diagnosis of prostate cancer is established when the disease has already metastasized to the bones, thus limiting the effectiveness of surgical treatments. Hormonal therapy frequently fails with time with the development of hormone-resistant tumor cells. Although chemotherapeutic agents have been used in the treatment of prostate cancer, no single agent has demonstrated superiority over its counterparts, and no drug combination seems particularly effective. The generally drug-resistant, slow-growing nature of most prostate cancers makes them particularly unresponsive to standard chemotherapy.

A major, indeed the overwhelming, obstacle to cancer therapy is the problem of selectivity; that is, the ability to inhibit the multiplication of tumor cells, while leaving unaffected the function of normal cells. For example, in prostate cancer therapy, the therapeutic ratio, or ratio of tumor cell killing to normal cell killing of traditional tumor chemotherapy, is only 1.5:1. Thus, more effective treatment methods and pharmaceutical compositions for therapy and prophylaxis of neoplasia are needed.

Of particular interest is development of more specific, targeted forms of cancer therapy, especially for cancers that are difficult to treat successfully. In contrast to conventional cancer therapies, which result in relatively non-specific and often serious toxicity, more specific treatment modalities attempt to inhibit or kill malignant cells selectively while leaving healthy cells intact.

One possible treatment approach for many of these cancers is gene therapy, whereby a gene of interest is introduced into the malignant cell. See, for gene therapy for prostate cancer, Boulikas (1997) *Anticancer Res.* 17:1471–1505. The gene of interest may encode a protein which converts into a toxic substance upon treatment with another compound, or an enzyme that converts a prodrug to a drug. For example, introduction of the herpes simplex gene encoding thymidine kinase (HSV-tk) renders cells conditionally sensitive to ganciclovir. Zjilstra et al. (1989) *Nature* 342: 435; Mansour et al. (1988) *Nature* 336: 348; Johnson et al. (1989) *Science* 245: 1234; Adair et al. (1989) *Proc. Natl. Acad. Sci. USA* 86: 4574; Capecchi (1989) *Science* 244: 1288. Alternatively, the gene of interest may encode a compound that is directly toxic, such as diphtheria toxin. For these treatments to be rendered specific to cancer cells, the gene of interest can be under control of a transcriptional regulatory element (TRE) that is specifically (i.e., preferentially) activated in the cancer cells. Cell or tissue specific expression can be achieved by using a TRE with cell-specific enhancers and/or promoters. See generally Huber et al. (1995) *Adv. Drug Delivery Reviews* 17:279–292.

A variety of viral and non-viral (e.g., liposomes) vehicles, or vectors, have been developed to transfer these genes. Of the viruses proposed for gene transfer, adenoviruses are among the most easily produced and purified. Adenovirus also has the advantage of effecting high efficiency of transduction and does not require cell proliferation for efficient transduction of cell. In addition, adenovirus can infect a wide variety of cells in vitro and in vivo. For general background references regarding adenovirus and development of adenoviral vector systems, see Graham et al. (1973) *Virology* 52:456–467; Takiff et al. (1981) *Lancet* 11:832–834; Berkner et al. (1983) *Nucleic Acid Research* 11: 6003–6020; Graham (1984) *EMBO J* 3:2917–2922; Bett et al. (1993) *J. Virology* 67:5911–5921; and Bett et al. (1994) *Proc. Natl. Acad. Sci. USA* 91:8802–8806.

When used as gene transfer vehicles, adenovirus vectors are often designed to be replication-defective and are thus deliberately engineered to fail to replicate in the target cells of interest. In these vehicles, the early adenovirus gene products E1A and/or E1B are deleted and provided in trans by the packaging cell line 293. Graham et al. (1987) *J. Gen. Virol* 36:59–72; Graham (1977) *J. Genetic Virology* 68:937–940. The gene to be transduced is commonly inserted into adenovirus in the E1A and E1B region of the virus genome. Bett et al. (1994). Replication-defective adenovirus vectors as vehicles for efficient transduction of genes have been described by, inter alia, Stratford-Perricaudet (1990) *Human Gene Therapy* 1:241–256; Rosenfeld (1991) *Science* 252:431–434; Wang et al. (1991) *Adv. Exp. Med. Biol.* 309:61–66; Jaffe et al. (1992) *Nat. Gen.* 1:372–378; Quantin et al. (1992) *Proc. Natl. Acad. Sci. USA* 89:2581–2584; Rosenfeld et al. (1992) *Cell* 68:143–155; Stratford-Perricaudet et al. (1992) *J. Clin. Invest.* 90:626–630; Le Gal Le Salle et al. (1993) *Science* 259:988–990 Mastrangeli et al. (1993) *J. Clin. Invest.* 91:225–234; Ragot et al. (1993) *Nature* 361:647–650; Hayaski et al. (1994) *J. Biol. Chem.* 269:23872–23875; Bett et al. (1994).

The virtually exclusive focus in development of adenoviral vectors for gene therapy is use of adenovirus merely as a vehicle for introducing the gene of interest, not as an effector in itself. Replication of adenovirus has been viewed as an undesirable result, largely due to the host immune response. In the treatment of cancer by replication-defective adenoviruses, the host immune response limits the duration of repeat doses at two levels. First, the capsid proteins of the adenovirus delivery vehicle itself are immunogenic. Second, viral late genes are frequently expressed in transduced cells, eliciting cellular immunity. Thus, the ability to repeatedly administer cytokines, tumor suppressor genes, ribozymes, suicide genes, or genes which convert prodrug to an active drug has been limited by the immunogenicity of both the gene transfer vehicle and the viral gene products of the transfer vehicle as well as the transient nature of gene expression.

Adenoviruses generally undergo an effective lytic replication cycle following infection of a host cell. In addition to lysing the infected cell, the replicative process of adenovirus blocks the transport and translation host cell mRNA thus inhibiting protein synthesis of the infected cell. For a review of adenoviruses and adenovirus replication, see Shenk, T. and Horwitz, M. S., *Virology,* third edition, Fields, B. N. et al., eds., Raven Press Limited, New York (1996), Chapters 67 and 68, respectively.

Taking advantage of the cytotoxic effects associated with adenovirus replication, replication-competent adenovirus vectors have recently been described as agents for effecting selective cell growth inhibition. See Henderson et al., U.S. Pat. No. 5,698,443; Hallenbeck et al., WO 96/17053. In such systems, a cell-specific transcriptional regulatory element (TRE) controls the expression of a gene essential for viral replication, and thus, viral replication is limited to a cell population in which the TRE is functional. For example, an attenuated, replication-competent adenovirus (CN706) has been generated by inserting the prostate-specific antigen (PSA) promoter and enhancer (PSE-TRE) upstream of the E1A transcription unit in adenovirus serotype 5 (Ad5). CN706 demonstrates selective cytotoxicity toward PSA expressing cells in vitro and in vivo. Rodriguez et al. (1997) *Cancer Res.* 57:2559–2563.

In sum, there is a need for vector constructs that are capable of eliminating essentially all cancerous cells in a minimum number of administrations before specific immunological response against the vector prevents further treatment. Particularly, there is a continuing serious need for improved replication-competent adenovirus vectors in which cell-specific replication can be further elevated, while minimizing the extent of replication in non-target (i.e., non-cancerous cells). The present invention provides selectively replicating adenovirus vectors that can be employed in these contexts.

SUMMARY OF THE INVENTION

The present invention provides an adenovirus vector comprising a first adenovirus gene under transcriptional control of a first heterologous transcriptional regulatory element (TRE) and at least a second gene under transcriptional control of a second heterologous TRE, wherein the first heterologous TREs is cell-specific, the first heterologous TRE is different from the second heterologous TRE and the heterologous TREs are functional in the same cell.

In one aspect, the invention provides an adenovirus vector in which the cell specific heterologous TRE controls the transcription of a gene essential for adenovirus replication.

In another aspect, the invention provides an adenovirus vector in which the second heterologous TRE controls the transcription of a transgene.

The invention further provides host cells containing the adenovirus vectors of the invention.

Further provided are methods of using the adenoviral vectors of the invention. In one aspect, methods are provided for using the adenovirus vectors described herein which entail introducing these vector(s) into a cell.

In another aspect, methods are provided for conferring selective cytotoxicity on a cell which allows the heterologous TREs to function that entail contacting the cells with an adenovirus vector described herein, wherein the adenovirus vector enters the cell.

In another aspect, methods are provided for suppressing tumor growth, comprising contacting a target cell with an adenovirus vector described herein such that the adenovirus vector enters the cell.

In another aspect, methods are provided for modifying the genotype of a target cell, comprising contacting the cell with an adenovirus vector described herein, wherein the adenovirus vector enters the cell.

In yet another aspect, methods are provided for propagating the adenovirus vectors of the invention, comprising combining the adenovirus vectors with cells which allow the heterologous TREs to function, such that the adenovirus vector enters the cell and is propagated.

BRIEF DESCRIPTION OF THE DRAWINGS

FIGS. 2(A)–(C) are schematic diagrams of examples of adenovirus vectors in which the E1A and E1B genes are under transcriptional control of prostate cell specific heterologous TREs. CN702 is an example of a wild-type Adenovirus type 5 and CN706 contains a single gene (E1A) under control of a single prostate cell specific TRE, one derived from the PSA gene.

FIG. 7 is a line graph showing serum PSA levels in mice treated with an adenovirus, CN739, in which multiple adenoviral early genes are placed under control of prostate cell specific heterologous TREs.

MODES FOR CARRYING OUT THE INVENTION

Figure 1:
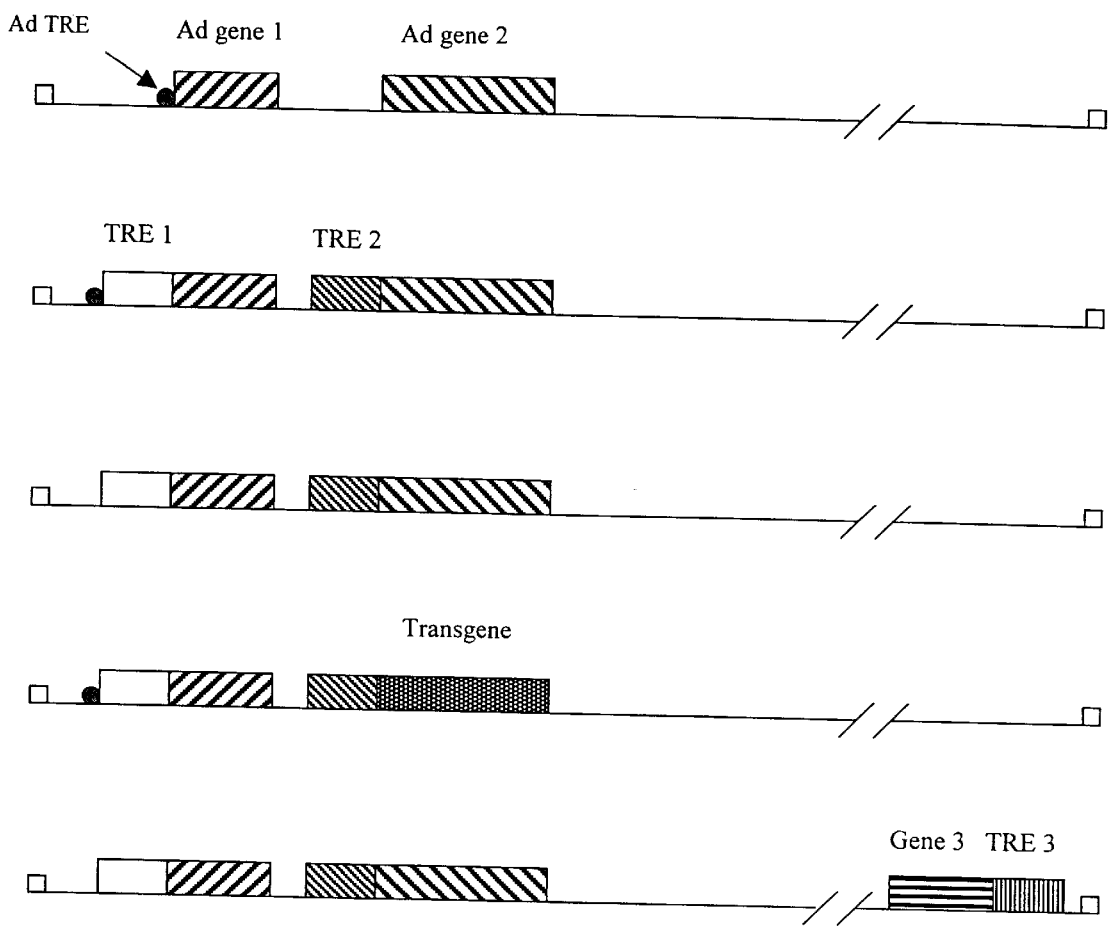
FIG. 1 depicts schematic diagrams of examples of adenovirus vectors in which various genes are under transcriptional control of various heterologous TREs. The heterologous TREs contained in an adenovirus vector are different from each other and from the endogenous adenovirus TREs. All of the heterologous TREs in an adenovirus vector are functional in the same cell and at least one of the TREs is cell specific.

We have discovered and constructed replication-competent adenovirus vectors containing heterologous cell-specific transcriptional regulatory elements (TREs) which can preferentially replicate in cells that allow function of said TREs and have developed methods of using these adenovirus vectors. The adenovirus vectors of this invention comprise a first adenovirus gene under the transcriptional control of a cell-specific heterologous TRE and at least one other gene, such as an adenoviral gene or a transgene, under control of another heterologous TRE which is different from the first TRE, where the heterologous TREs are functional in the same cell but are not the same in polynucleotide sequence (i.e., have different polynucleotide sequences). Preferably, at least two of the heterologous TREs in an adenovirus vector are cell specific for the same cell. Preferably, the adenovirus gene is one that enhances cell death, more preferably one that is essential for adenovirus replication. Preferably, at least one of the adenovirus genes necessary for cell replication is an early gene. Preferably, the genes under transcriptional control of the heterologous TREs are necessary for replication. By providing for cell-specific transcription through the use of multiple heterologous TREs, the invention provides adenovirus vectors that can be used for cell-specific cytotoxic effects due to selective replication.

The adenovirus vectors of the invention replicate preferentially in TRE functional cells (i.e., at a higher yield than in TRE non-functional cells). This replication preference is indicated by comparing the level of replication (i.e., titer) in cells in which the TRE is active to the level of replication in cells in which the TRE is not active. The replication preference is even more significant, as the adenovirus vectors of the invention actually replicate at a significantly lower rate in TRE non-functional cells than wild type virus. Comparison of the adenovirus titer of a TRE active cell type to the titer of a TRE inactive cell type provides a key indication that the overall replication preference is enhanced due to the replication in TRE active cells as well as depressed replication in TRE inactive cells. This is especially useful in the cancer context, in which targeted cell killing is desirable.

The adenovirus vectors of this invention, with the inclusion of at least two different heterologous TREs, are more stable and provide even more cell specificity with regard to replication than previously described adenovirus vectors. Adenovirus vectors have been constructed in which each of the E1A and E1B genes have been placed under transcriptional control of two different heterologous TREs, for example, TREs from the PSA gene (PSE-TRE) and the probasin gene (PB-TRE) and TREs from the PSA gene and the hKLK2 gene (hKLK2-TRE).

We have found, for example, that adenoviruses containing the PSE-TRE and the PB-TRE and adenovirus containing the PSE-TRE and the hKLK2-TRE appear to possess a stable genome, exhibit higher levels of cell specificity with regard to replication than CN706, an adenovirus with the PSE-TRE controlling the E1A gene, and replicate as efficiently as CN706 in prostate cells. As shown herein, in vitro and in vivo results indicate the CN739 (adenovirus with a PB-TRE controlling the E1A gene and a PSE-TRE controlling the E1B gene, described below) and CN764 (adenovirus with a PSE-TRE controlling the E1A gene and an hKLK2-TRE controlling the E1B gene, described below) have a 10 to 100-fold higher cell specificity in replication than CN706, while retaining similar prostate tumor killing capacity. Thus, this invention provides an even more attenuated replication competent virus by controlling replication genes with two different heterologous, cell-specific TREs.

Previous attempts to achieve this level of specificity through the construction of adenovirus vectors with the same heterologous TRE controlling transcription of two adenoviral vector genes appear to have resulted in unstable genomes and undesirable polynucleotide sequence rearrangements. Examination of such adenoviruses, with techniques such as restriction enzyme digestion and Southern blot analysis, revealed alterations in the size of adenoviral polynucleotide fragments after viral replication. Without wishing to be bound by theory, such genome instability may be the result of homologous recombination through the duplicated TRE sequences.

The adenovirus vectors provided by the present invention, in which two different heterologous TREs are used to control replication, achieve a stability of the viral genome and an even higher level of target cell specificity than previously described adenoviruses.

The invention uses and takes advantage of what has been considered an undesirable aspect of adenoviral vectors, namely, their replication and possible concomitant immunogenicity. Runaway infection is prevented due to the cell-specific requirements for viral replication. Without wishing to be bound by any particular theory, the inventors note that production of adenovirus proteins can serve to activate and/or stimulate the immune system, either generally or specifically toward target cells producing adenoviral proteins which can be an important consideration in the cancer context, where patients are often moderately to severely immunocompromised.

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology" (D. M. Weir & C. C. Blackwell, eds.); "Gene Transfer Vectors for Mammalian Cells" (J. M. Miller & M. P. Calos, eds., 1987); "Current Protocols in Molecular Biology" (F. M. Ausubel et al., eds., 1987); "PCR: The Polymerase Chain Reaction", (Mullis et al., eds., 1994); and "Current Protocols in Immunology" (J. E. Coligan et al., eds., 1991).

For techniques related to adenovirus, see, inter alia, Felgner and Ringold (1989) *Nature* 337:387–388; Berkner and Sharp (1983) *Nucl. Acids Res.* 11:6003–6020; Graham (1984) *EMBO J.* 3:2917–2922; Bett et al. (1993) *J. Virology* 67:5911–5921; Bett et al. (1994) *Proc. Natl. Acad. Sci. USA* 91:8802–8806.

Definitions

As used herein, "adenovirus" refers to the virus itself or derivatives thereof. The term covers all serotypes and subtypes and both naturally occurring and recombinant forms, except where indicated otherwise.

The term "polynucleotide" as used herein refers to a polymeric form of nucleotides of any length, either ribonucleotides or deoxynucleotides. Thus, this term includes single-, double- and triple-stranded DNA, as well as single- and double-stranded RNA, RNA-DNA hybrids, or a polymer comprising purine and pyrimidine bases, or other natural, chemically, biochemically modified, non-natural or derivatized nucleotide bases. The backbone of the polynucleotide can comprise sugars and phosphate groups (as may typically be found in RNA or DNA), or modified or substituted sugar or phosphate groups. Alternatively, the backbone of the polynucleotide can comprise a polymer of synthetic subunits such as phosphoramidates and thus can be a oligodeoxynucleoside phosphoramidate (P-NH2) or a mixed phosphoramidate-phosphodiester oligomer. Peyrottes et al. (1996) *Nucleic Acids Res.* 24: 1841–8; Chaturvedi et al. (1996) *Nucleic Acids Res.* 24: 2318–23; Schultz et al. (1996) *Nucleic Acids Res.* 24: 2966–73. A phosphorothioate linkage can be used in place of a phosphodiester linkage. Braun et al. (1988) *J. Immunol.* 141: 2084–9; Latimer et al. (1995) *Mol. Immunol.* 32: 1057–1064. Preferably, the polynucleotide is DNA. As used herein, "DNA" includes not only bases A, T, C, and G, but also includes any of their analogs or modified forms of these bases, such as methylated nucleotides, internucleotide modifications such as uncharged linkages and thioates, use of sugar analogs, and modified and/or alternative backbone structures, such as polyamides. In addition, a double-stranded polynucleotide can be obtained from the single-stranded polynucleotide product of chemical synthesis either by synthesizing the complementary strand and annealing the strands under appropriate conditions, or by synthesizing the complementary strand de novo using a DNA polymerase with an appropriate primer.

The term "gene" is well understood in the art and is a polynucleotide encoding a polypeptide. In addition to the polypeptide coding regions, a gene includes non-coding regions including, but not limited to, introns, transcribed but untranslated segments, and regulatory elements upstream and downstream of the coding segments.

As used herein, a "transcriptional regulatory element", or "TRE" is a polynucleotide sequence, preferably a DNA sequence, that regulates (i.e., controls) transcription of an operably-linked polynucleotide sequence by an RNA polymerase to form RNA. As used herein, a TRE increases transcription of an operably linked polynucleotide sequence in a host cell that allows the TRE to function. The TRE comprises an enhancer element and/or promoter element, which may or may not be derived from the same gene. The promoter and enhancer components of a TRE may be in any orientation and/or distance from the coding sequence of interest, and comprise multimers of the foregoing, as long as the desired transcriptional activity is obtained. As discussed herein, a TRE may or may not lack a silencer element.

An "enhancer" is a term well understood in the art and is a polynucleotide sequence derived from a gene which increases transcription of a gene which is operably-linked to a promoter to an extent which is greater than the transcription activation effected by the promoter itself when operably-linked to the gene, i.e. it increases transcription from the promoter. Having "enhancer activity" is a term well understood in the art and means what has been stated, i.e., it increases transcription of a gene which is operably linked to a promoter to an extent which is greater than the increase in transcription effected by the promoter itself when operably linked to the gene, i.e., it increases transcription from the promoter.

A polynucleotide or polynucleotide region has a certain percentage (for example, 80%, 85%, 90%, or 95%) of "sequence identity" to another sequence means that, when aligned, that percentage of bases are the same in comparing the two sequences. This alignment and the percent homology or sequence identity can be determined using software programs known in the art, for example those described in *Current Protocols in Molecular Biology* (F. M. Ausubel et al., eds., 1987) Supplement 30, section 7.7.18, Table 7.7.1. A preferred alignment program is ALIGN Plus (Scientific and Educational Software, Pennsylvania).

In the context of adenovirus vector(s), a first heterologous TRE is "different" from a second (or another) heterologous TRE when the polynucleotide sequence identity between the two heterologous TREs is less than about 95%, preferably less than about 90%, preferably less than about 85%, preferably less than about 75%. Generally, "different TREs" are derived from the transcriptional regulatory regions of different genes. "Different TREs" may also be derived from the transcriptional regulatory region of the same gene, as long as the sequence identity between them is less than the values listed above (i.e., less than about 95%, preferably less than about 90%, preferably less than about 85%, preferably less than about 75%). Although two different TREs are not identical in polynucleotide sequence, they may be functional in the same cell and may also have the same cell-specificity.

As used herein, a TRE derived from a specific gene is referred to by the gene from which it was derived and is a polynucleotide sequence which regulates transcription of an operably linked polynucleotide sequence in a host cell that expresses said gene. For example, as used herein, a "human glandular kallikrein transcriptional regulatory element", or "hKLK2-TRE" is a polynucleotide sequence, preferably a DNA sequence, which increases transcription of an operably linked polynucleotide sequence in a host cell that allows an hKLK2-TRE to function, such as a cell (preferably a mammalian cell, even more preferably a human cell) that expresses androgen receptor. An hKLK2-TRE is thus responsive to the binding of androgen receptor and comprises at least a portion of an hKLK2 promoter and/or an hKLK2 enhancer (i.e., the ARE or androgen receptor binding site).

As used herein, a "probasin (PB) transcriptional regulatory element", or "PB-TRE" is a polynucleotide sequence, preferably a DNA sequence, which selectively increases transcription of an operably-linked polynucleotide sequence in a host cell that allows a PB-TRE to function, such as a cell (preferably a mammalian cell, even more preferably a human cell) that expresses androgen receptor. A PB-TRE is thus responsive to the binding of androgen receptor and comprises at least a portion of a PB promoter and/or a PB enhancer (i.e., the ARE or androgen receptor binding site).

As used herein, a "prostate-specific antigen (PSA) transcriptional regulatory element", or "PSA-TRE", or "PSE-TRE" is polynucleotide sequence, preferably a DNA sequence, which selectively increases transcription of an operably linked polynucleotide sequence in a host cell that allows a PSA-TRE to function, such as a cell (preferably a mammalian cell, even more preferably a human cell) that expresses androgen receptor. A PSE-TRE is thus responsive to the binding of androgen receptor and comprises at least a portion of a PSA promoter and/or a PSA enhancer (i.e., the ARE or androgen receptor binding site).

As used herein, a "carcinoembryonic antigen (CEA) transcriptional regulatory element", or "CEA-TRE" is polynucleotide sequence, preferably a DNA sequence, which selectively increases transcription of an operably linked polynucleotide sequence in a host cell that allows a CEA-TRE to function, such as a cell (preferably a mammalian cell, even more preferably a human cell) that expresses CEA. The CEA-TRE is responsive to transcription factors and/or co-factor(s) associated with CEA-producing cells and comprises at least a portion of the CEA promoter and/or enhancer.

As used herein, an "α-fetoprotein (AFP) transcriptional regulatory element", or "AFP-TRE" is polynucleotide sequence, preferably a DNA sequence, which selectively increases transcription (of an operably linked polynucleotide sequence) in a host cell that allows an AFP-TRE to function, such as a cell (preferably a mammalian cell, even more preferably a human cell) that expresses AFP. The AFP-TRE is responsive to transcription factors and/or co-factor(s) associated with AFP-producing cells and comprises at least a portion of the AFP promoter and/or enhancer.

As used herein, an "a mucin gene (MUC) transcriptional regulatory element", or "MUC1-TRE" is a polynucleotide sequence, preferably a DNA sequence, which selectively increases transcription (of an operably-linked polynucleotide sequence) in a host cell that allows an MUC1-TRE to function, such as a cell (preferably a mammalian cell, even more preferably a human cell) that expresses MUC1. The MUC1-TRE is responsive to transcription factors and/or co-factor(s) associated with MUC1-producing cells and comprises at least a portion of the MUC1 promoter and/or enhancer.

A "cell-specific TRE" is preferentially functional in a specific type of cell relative to other types of cells of different functionality. A cell-specific TRE may or may not be tumor cell specific.

As used herein, the term "target cell-specific" is intended to mean that the TRE sequences to which a gene essential for replication of an adenoviral vector is operably linked, or to which a transgene is operably linked, functions specifically in that target cell so that replication proceeds in that target cell, or so that a transgene polynucleotide is expressed in that target cell. This can occur by virtue of the presence in that target cell, and not in non-target cells, of transcription factors that activate transcription driven by the operably linked transcriptional control sequences. It can also occur by virtue of the absence of transcription inhibiting factors that normally occur in non-target cells and prevent transcription driven by the operably linked transcriptional control sequences. The term "target cell-specific", as used herein, is intended to include cell type specificity, tissue specificity, as well as specificity for a cancerous state of a given target cell. In the latter case, specificity for a cancerous state of a normal cell is in comparison to a normal, non-cancerous counterpart.

The activity of a TRE generally depends upon the presence of transcriptional regulatory factors and/or the absence of transcriptional regulatory inhibitors. Transcriptional activation can be measured in a number of ways known in the art (and described in more detail below), but is generally measured by detection and/or quantitation of mRNA or the protein product of the coding sequence under control of (i.e., operatively linked to) the TRE. As discussed herein, a TRE can be of varying lengths, and of varying sequence composition. By transcriptional activation, it is intended that transcription will be increased above basal levels in the target cell by at least about 2-fold, preferably at least about 5-fold, preferably at least about 10-fold, more preferably at least about 20-fold. More preferably at least about 50-fold, more preferably at least about 100-fold, even more preferably at least about 200-fold, even more preferably at least about 400- to about 500-fold, even more preferably, at least about 1000-fold. Basal levels are generally the level of activity, if any, in a non-target cells, or the level of activity (if any) of a reporter construct lacking the TRE of interest as tested in a target cell type.

A "functionally-preserved" variant of a TRE is a TRE which differs from another TRE, but still retains ability to increase transcription of an operably linked polynucleotide, especially cell-specific transcription activity. The difference in a TRE can be due to differences in linear sequence, arising from, for example, single or multiple base mutation(s), addition(s), deletion(s), and/or modification(s) of the bases. The difference can also arise from changes in the sugar(s), and/or linkage(s) between the bases of a TRE.

Certain point mutations within sequences of TREs have been shown to decrease transcription factor binding and gene activation. One of skill in the art would recognize that some alterations of bases in and around known the transcription factor binding sites are more likely to negatively affect gene activation and cell-specificity, while alterations in bases which are not involved in transcription factor binding are not as likely to have such effects. Certain mutations are also capable of increasing TRE activity. Testing of the effects of altering bases may be performed in vitro or in vivo by any method known in the art, such as mobility shift assays, or transfecting vectors containing these alterations in TRE functional and TRE non-functional cells. Additionally, one of skill in the art would recognize that point mutations and deletions can be made to a TRE sequence without altering the ability of the sequence to regulate transcription.

"Under transcriptional control" is a term well-understood in the art and indicates that transcription of a polynucleotide sequence, usually a DNA sequence, depends on its being operably (operatively) linked to an element which contributes to the regulation of, either promotes or inhibits, transcription.

The term "operably linked" relates to the orientation of polynucleotide elements in a functional relationship. A TRE is operably linked to a coding segment if the TRE promotes transcription of the coding sequence. Operably linked means that the DNA sequences being linked are generally contiguous and, where necessary to join two protein coding regions, contiguous and in the same reading frame. However, since enhancers generally function when separated from the promoter by several kilobases and intronic sequences may be of variable length, some polynucleotide elements may be operably linked but not contiguous.

As used herein, "a cell which allows a TRE to function" or a cell in which the function of a TRE is "sufficiently preserved", or "a cell in which a TRE is functional" is a cell in which the TRE, when operably linked to a promoter (if not included in the TRE) and a reporter gene, increases expression of the reporter gene at least about 2-fold, preferably at least about 5-fold, preferably at least about 10-fold, more preferably at least about 20-fold, more preferably at least about 50-fold, more preferably at least about 100-fold, more preferably at least about 200-fold, even more preferably at least about 400- to about 500-fold, even more preferably at least about 1000-fold, when compared to the expression of the same promoter and reporter gene when not operably linked to said TRE. Methods for measuring levels (whether relative or absolute) of expression are known in the art and are described herein.

A "target cell" is any cell that allows a heterologous TRE to function. Preferably, a target cell is a mammalian cell, more preferably a human cell.

As used herein, "neoplastic cells", "neoplasia", "tumor", "tumor cells", "cancer", and "cancer cells" (used interchangably) refer to cells which exhibit relatively autonomous growth, so that they exhibit an aberrant growth phenotype characterized by a significant loss of control of cell proliferation. Neoplastic cells can be benign or malignant.

"Androgen receptor", or AR as used herein refers to a protein whose function is to specifically bind to androgen and, as a consequence of the specific binding, recognize and bind to an androgen response element (ARE), following which the AR is capable of regulating transcriptional activity. The AR is a nuclear receptor that, when activated, binds to cellular androgen-responsive element(s). In normal cells the AR is activated by androgen, but in non-normal cells (including malignant cells) the AR may be activated by non-androgenic agents, including hormones other than androgens. Encompassed in the term "androgen receptor" are mutant forms of an androgen receptor, as long as the function is sufficiently preserved. Mutants include androgen receptors with amino acid additions, insertions, truncations and deletions, as long as the function is sufficiently preserved. In this context, a functional androgen receptor is one that binds both androgen and, upon androgen binding, an ARE.

An "adenovirus vector" or "adenoviral vector" (used interchangeably) is a term well understood in the art and generally comprises a polynucleotide (defined herein) comprising all or a portion of an adenovirus genome. For the purpose of the present invention, an adenovirus vector contains a heterologous TRE operably linked to a polynucleotide. The operably linked polynucleotide can be adenoviral or heterologous. An adenovirus is exemplified by, but not limited to, Ad2, Ad5, Ad12, and Ad40. The terms "vector", "polynucleotide vector", "construct", "polynucleotide construct" and "vector construct" are used interchangeably herein. An adenoviral vector of this invention may be in any of several forms, including, but not limited to, naked DNA, DNA encapsulated in an adenovirus coat, DNA packaged in another viral or viral-like form (such as herpes simplex, and AAV), DNA encapsulated in liposomes, DNA complexed with polylysine, complexed with synthetic polycationic molecules, conjugated with transferrin, complexed with compounds such as PEG to immunologically "mask" the molecule and/or increase half-life, or conjugated to a non-viral protein. For purposes of this invention, adenovirus vectors are replication-competent in a target cell.

"Heterologous" means derived from a genotypically distinct entity from that of the rest of the entity to which it is being compared.

A "heterologous" TRE is one which is not associated with or derived from a wild-type adenovirus. Examples of heterologous TREs are the albumin promoter or enhancer and other viral promoters and enhancers, such as SV40. Examples of preferred heterologous TREs are provided herein.

A "heterologous gene" or "transgene" is any gene that is not present in wild-type adenovirus. Preferably, the transgene will also not be expressed or present in the target cell prior to introduction by the adenovirus vector. Examples of preferred transgenes are provided below.

An "endogenous" promoter, enhancer, or TRE is native to or derived from adenovirus.

"Replication" and "propagation" are used interchangeably and refer to the ability of an adenovirus vector of the invention to reproduce or proliferate. This term is well understood in the art. For purposes of this invention, replication involves production of adenovirus proteins and is generally directed to reproduction of adenovirus. Replication can be measured using assays standard in the art and described herein, such as a burst assay or plaque assay. "Replication" and "propagation" include any activity directly or indirectly involved in the process of virus manufacture, including, but not limited to, viral gene expression, production of viral proteins, nucleic acids or other components, packaging of viral components into complete viruses, and cell lysis.

A "gene essential for replication" is a gene whose transcription is required for the vector to replicate in a cell.

The terms "polypeptide", "peptide" and "protein" are used interchangeably to refer to polymers of amino acids of any length. These terms also include proteins that are post-translationally modified through reactions that include glycosylation, acetylation and phosphorylation.

A "host cell" includes an individual cell or cell culture which can be or has been a recipient of an adenoviral vector of this invention. Host cells include progeny of a single host cell, and the progeny may not necessarily be completely identical (in morphology or in total DNA complement) to the original parent cell due to natural, accidental, or deliberate mutation and/or change. A host cell includes cells transfected or infected in vivo with an adenoviral vector of this invention.

As used herein, "cytotoxicity" is a term well understood in the art and refers to a state in which one or more of a cell's usual biochemical or biological functions are aberrantly compromised (i.e., inhibited or elevated). These activities include, but are not limited to, metabolism, cellular replication, DNA replication, transcription, translation, and uptake of molecules. "Cytotoxicity" includes cell death and/or cytolysis. Assays are known in the art which indicate cytotoxicity, such as dye exclusion, $^3$H-thymidine uptake, and plaque assays. The term "selective cytotoxicity", as used herein, refers to the cytotoxicity conferred by an adenoviral vector of the present invention on a cell which allows a TRE to function when compared to the cytotoxicity conferred by an adenoviral vector of the present invention on a cell which does not allow, or is less permissive for, the same TRE to function. Such cytotoxicity may be measured, for example, by plaque assays, reduction or stabilization in size of a tumor comprising target cells, or the reduction or stabilization of serum levels of a marker characteristic of the tumor cells or a tissue-specific marker, e.g., a cancer marker such as prostate specific antigen.

As used herein, a "cytotoxic" gene is a gene whose expression in a cell, either alone or in conjunction with adenovirus replication, enhances the degree and/or rate of cytotoxic and/or cytolytic activity in the cell.

A "therapeutic" gene is a gene whose expression in a cell is associated with a desirable result. In the cancer context, this desirable result may be, for example, cytotoxicity, repression or slowing of cell growth, and/or cell death.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents, solubilization, or enrichment for certain components, such as proteins or polynucleotides. The term "biological sample" encompasses a clinical sample, and also includes cells in culture, cell supernatants, cell lysates, serum, plasma, biological fluid, and tissue samples.

An "individual" is a vertebrate, preferably a mammal, more preferably a human. Mammals include, but are not limited to, farm animals, sport animals, and pets.

An "effective amount" is an amount sufficient to effect beneficial or desired clinical results. An effective amount can be administered in one or more administrations. For purposes of this invention, an effective amount of an adenoviral vector is an amount that is sufficient to palliate, ameliorate, stabilize, reverse, slow or delay the progression of the disease state.

As used herein, "treatment" is an approach for obtaining beneficial or desired clinical results. For purposes of this invention, beneficial or desired clinical results include, but are not limited to, alleviation of symptoms, diminishment of extent of disease, stabilized (i.e., not worsening) state of disease, preventing spread (i.e., metastasis) of disease, delay or slowing of disease progression, amelioration or palliation of the disease state, and remission (whether partial or total), whether detectable or undetectable. "Treatment" can also mean prolonging survival as compared to expected survival if not receiving treatment.

"Palliating" a disease means that the extent and/or undesirable clinical manifestations of a disease state are lessened and/or time course of the progression is slowed or lengthened, as compared to not administering adenoviral vectors of the present invention.

Adenoviral Vectors Comprising Heterologous TREs

The present invention provides adenoviral vectors which comprise a first adenovirus gene under transcriptional control of a heterologous (i.e., non-adenovirus) TRE and at least a second gene under transcriptional control of a second heterologous TRE, wherein the two heterologous TREs are different from each other (in nucleotide sequence) but are functional in the same cell. In addition, at least the first heterologous TRE is cell-specific. Preferably, the adenovirus gene is one that contributes to cytotoxicity (whether direct and/or indirect), more preferably one that contributes to and/or causes cell death, and even more preferably the first adenoviral gene is essential from adenovirus replication. Examples of an adenovirus gene that contributes to cytotoxicity include, but are not limited to, the adenovirus death protein gene. See FIG. 1 for diagrammatic examples.

Because the adenovirus vector(s) is selectively (i.e. preferentially) replication-competent for propagation in target cells which allow the function of the heterologous TREs, these cells will be preferentially subject to the cytotoxic and/or cytolytic effects of adenoviral proliferation. Preferably, target cells are neoplastic cells, although any cell for which it is desirable and/or tolerable to sustain this cytotoxic activity may be a target cell. By combining the adenovirus vector(s) with the mixture of target and non-target cells, in vitro or in vivo, the adenovirus vector(s) preferentially replicates in the target cells. Once the target cells are destroyed due to selective cytotoxic and/or cytolytic replication, the adenovirus vector(s) replication is significantly reduced, lessening the probability of runaway infection and undesirable bystander effects. In vitro cultures may be retained to continually monitor the mixture (such as, for example, a biopsy or other appropriate biological sample) for occurrence (i.e. presence) and/or recurrence of the target cell, e.g., a cancer cell in which the cell specific TRE is functional.

To ensure cytotoxicity further, one or more transgenes having a cytotoxic effect may also be present and under the selective transcriptional control of a heterologous TRE. Additionally, or alternatively, an adenovirus gene that contributes to cytotoxicity and/or cell death (such as the adenovirus death protein (ADP) gene) may be included in the adenoviral vector, either free of, or under, the selective transcriptional control of a heterologous TRE. In these embodiments, one may provide higher confidence that the target cells will be destroyed.

In one embodiment, the invention provides an adenovirus vector comprising an adenovirus gene essential for replication under transcriptional control of a heterologous, cell specific TRE, wherein the TRE selectively regulates the expression of said gene in a target cell. Further, the adenovirus vector comprises a second gene under transcriptional control of a second heterologous TRE, wherein the first and second heterologous TREs are functional in the same cell and the TREs are different from each other.

Cell, or tissue, specific transcriptional regulatory elements are well known in the art. TREs may be derived from the transcriptional regulatory sequences of a single gene or from different genes and combined to produce a functional TRE. A cell-specific TRE is preferentially functional in a limited population (or type) of cells, e.g., prostate cells or liver cells.

As is known in the art, activity of TREs can be inducible. Inducible TREs generally exhibit low activity in the absence of the inducer, and are up-regulated in the presence of the inducer. Inducible TREs may be preferred when expression is desired only at certain times or at certain locations, or when it is desirable to titrate the level of expression using an inducing agent. For example, transcriptional activity from the PSE-TRE, PB-TRE and hKLK2-TRE is inducible by androgen, as described herein. Accordingly, in one embodiment, a heterologous TRE of the adenovirus vector is inducible.

As mentioned, TRE can also comprise multimers. For example, a TRE can comprise a tandem series of at least two, at least three, at least four, at least five promoter fragments. Alternatively, a TRE could have one or more promoter regions along with one or more enhancer regions. These multimers may also contain promoter and/or enhancer sequences from different genes. In addition, the promoter and enhancer components of a TRE may be in any orientation and/or distance from the coding sequence of interest, as long as the desired cell-specific transcriptional activity is obtained.

A TRE used in the present invention may or may not lack a silencer. The presence of a silencer (i.e., a negative regulatory element known in the art) can assist in shutting off transcription (and thus replication) in non-permissive cells. Thus, presence of a silencer can confer enhanced cell-specific replication by more effectively preventing adenoviral vector replication in non-target cells. Alternatively, lack of a silencer may assist in effecting replication in target cells, thus conferring enhanced cell-specific replication due to more effective replication in target cells.

When used in an adenovirus vector of the present invention, the heterologous TREs have a different polynucleotide sequence from each other. Accordingly, in a given adenovirus vector, the sequence identity between the two heterologous TREs is less than about 95%, preferably less than about 90%, more preferably less than about 85%, more preferably less than 80%, even more preferably less than about 75%. Despite the difference in sequence identity, the heterologous TREs of a given adenovirus vector are functional in the same cell. The difference(s) may arise from, for example, varying the sequence of a TRE derived from a single gene. It is possible to generate such TREs using standard methods in the art and/or allowing sequences to alter during the course of propagation. The difference(s) may also arise from TREs that are derived from different genes.

As is readily appreciated by one skilled in the art, a TRE is a polynucleotide sequence, and, as such, can exhibit function over a variety of sequence permutations. Methods of nucleotide substitution, addition, and deletion are known in the art, and readily available functional assays (such as the CAT or luciferase reporter gene assay) allow one of ordinary skill to determine whether a sequence variant exhibits requisite cell-specific transcription function.

Hence, functionally preserved variants of TREs may also be used including nucleic acid substitutions, additions, and/or deletions. Accordingly, variants of TREs must retain function in the target cell but need not be of maximal function.

It is possible that certain base modifications will result in enhanced expression levels and/or cell-specificity. Nucleic acid sequence deletions or additions within a TRE may decrease or increase transcription if they bring transcription regulatory protein binding sites too close or too far away or rotate them so they are on opposite sides of the DNA helix, as is known in the art. Thus, while the inventors are not wishing to be bound by a single theory, it is possible that certain modifications will result in modulated resultant expression levels, including enhanced cell-specific expression levels. Achievement of enhanced expression levels may be especially desirable in the case of more aggressive forms of neoplastic growth, or when a more rapid and/or aggressive pattern of cell killing is warranted (due to an immunocompromised condition of the individual, for example).

Transcriptional activity (including decrease or enhancement) can be measured in a number of ways known in the art (and described in more detail below), but is generally measured by detection and/or quantitation of mRNA or the protein product of the coding sequence under control of (i.e., operably linked to) a TRE. As discussed herein, a TRE can be of varying lengths, and of varying sequence composition. By transcriptional activity, it is intended that transcription due to the presence of the enhancer is increased above basal levels (i.e., promoter alone; lacking enhancer) in the target cell by at least about 2-fold, preferably at least about 5-fold, preferably at least about 10-fold, more preferably at least about 20-fold, more preferably at least about 50-fold, more preferably at least about 100-fold, more preferably at least about 200-fold, even more preferably at least about 400- to about 500-fold, even more preferably at least about 1000-fold. Basal levels are generally the level of activity, if any, in a non-target cell, or the level of activity (if any) of a reporter construct lacking a TRE as tested in a non-target cell.

Maximal transcriptional activation activity of a TRE may not always be necessary to achieve a desired result. The level of induction afforded by a fragment of a TRE may be sufficient in certain applications to achieve a desired result. For example, if used for treatment or palliation of a disease state, less-than-maximal responsiveness may be sufficient for the desired result, if, for example, the target cells are not especially virulent and/or the extent of disease is relatively confined.

The size of the heterologous TREs will be determined in part by the capacity of the adenoviral vector, which in turn depends upon the contemplated form of the vector (see below). Generally minimal sizes are preferred, as this provides potential room for insertion of other sequences which may be desirable, such as transgenes (discussed below) or other additional regulatory sequences. However, if no additional sequences are contemplated, or if, for example, an adenoviral vector will be maintained and delivered free of any viral packaging constraints, larger DNA sequences may be used as long as the resultant adenoviral vector is rendered replication-competent.

If no adenovirus sequences have been deleted, an adenoviral vector can be packaged with extra sequences totaling up to about 5% of the genome size, or approximately 1.8 kb. If non-essential sequences are removed from the adenovirus genome, an additional 4.6 kb of insert can be tolerated (i.e., a total of about 1.8 kb plus 4.6 kb, which is about 6.4 kb). Examples of non-essential adenoviral sequences that can be deleted are E3 and E4 (as long as the E4 ORF6 is maintained).

In order to minimize non-specific replication, endogenous (i.e., adenovirus) TREs should preferably be removed. This would also provide more room for inserts in an adenoviral vector, which may be of special concern if an adenoviral vector will be packaged as a virus (see below). Even more importantly, deletion of endogenous TREs would prevent a possibility of a recombination event whereby a heterologous TRE is deleted and the endogenous TRE assumes transcriptional control of its respective adenovirus coding sequences (thus allowing non-specific replication). In one embodiment, an adenoviral vector of the invention is constructed such that the endogenous transcription control sequences of adenoviral genes are deleted and replaced by a heterologous TREs. However, endogenous TREs may be maintained in the adenovirus vector(s), provided that sufficient cell-specific replication preference is preserved. These embodiments can be constructed by providing heterologous TREs intervening between the endogenous TRE and the replication gene coding segment. Requisite cell-specific replication preference is indicated by conducting assays that compare replication of the adenovirus vector in a cell which allows function of the heterologous TREs with replication in a cell which does not.

Generally, it is intended that replication is increased above basal levels in the target cell by at least about 2-fold, preferably at least about 5-fold, preferably at least about 10-fold more preferably at least about 20-fold, more preferably at least about 50-fold, more preferably at least about 100-fold, more preferably at least about 200-fold, even more preferably at least about 400- to about 500-fold, even more preferably at least about 1000-fold. The acceptable differential can be determined empirically (using, for example, Northern assays or other known in the art) and will depend upon the anticipated use of the adenoviral vector and/or the desired result.

(a) Exemplary Heterologous TREs

Cell, or tissue, specific transcriptional regulatory elements are well known in the art. Methods to identify such elements are also well known in the art. The cell specific TREs provided below are illustrative examples and not meant to limit the invention.

In one embodiment, the invention includes adenovirus vectors wherein the heterologous TREs are prostate cell specific. For example, TREs that function preferentially in prostate cells and can be used in the present invention to target adenovirus replication to prostate neoplasia, include, but are not limited to, TREs derived from the prostate-specific antigen gene (PSA-TRE), the glandular kallikrein-1 gene (from the human gene, hKLK2-TRE), and the probasin gene (PB-TRE). All three of these genes are preferentially expressed in prostate cells and the expression is androgen-inducible. Generally, expression of genes responsive to androgen induction requires the presence of an androgen receptor (AR).

PSA is synthesized exclusively by normal, hyperplastic, and malignant prostatic epithelia; hence, its tissue-specific expression has made it an excellent biomarker for benign prostatic hyperplasia (BPH) and prostatic carcinoma (CaP). Normal serum levels of PSA are typically below 5 ng/ml, with elevated levels indicative of BPH or CaP. Lundwall et al. (1987) FEBS Lett. 214: 317; Lundwall (1989) Biochem. Biophys. Res. Comm. 161: 1151; and Riegmann et al. (1991) Molec. Endocrin. 5: 1921.

The region of the PSA gene that is used to provide cell specificity dependent upon androgens, particular in prostate cells, involves approximately 6.0 kilobases. Schuur et al. (1996) J. Biol. Chem. 271:7043–7051. An enhancer region of approximately 1.5 kb in humans is located between nt −5322 and nt −3739, relative to the transcription start site of the PSA gene. The PSA promoter consists of the sequence from about nt −540 to nt +8 relative to the transcription start site. Juxtapositioning of these two genetic elements yield a fully functional, minimal prostate-specific enhancer/promoter (PSE) TRE. Other portions of the approximately 6.0 kb region of the PSA gene can be used in the present invention, as long as requisite functionality is maintained.

The PSE and PSA TRE depicted in (SEQ ID NO:1) is the same as that given in GenBank Accession No. U37672, and published. Schuur et al. (1996). A variant PSA-TRE nucleotide sequence is depicted in (SEQ ID NO:2). This is the PSA-TRE contained within CN706 clone 35.190.13. CN706 is an adenoviral vector in which the E1A gene in Ad5 is under transcriptional control of a PSA-TRE. CN706 demonstrates selective cytotoxicity toward PSA-expressing cells in vitro and in vivo. Rodriguez et al. (1997). CN706 was passaged through 293 and LNCaP cells. A clone, designated 35.190.13 was isolated. The structure of this clone was confirmed by PCR, restriction endonuclease digestion and Southern blotting. Both DNA strands of the CN706 clone 35.190.13 were sequenced between positions 1 and 3537. Seven single base pair changes were found in the PSE, compared to the sequence reported by Schuur et al. (1996). These point mutations are not in the ARE and are thus not likely to affect the function of the enhancer. One mutation was found in the PSA promoter region, but is not likely to affect gene expression from this promoter. In addition to these mutations, a missense mutation was found in the first exon of E1A. This C to G transition at position 3032 results in a Glu to Arg change in the E1A protein sequence. This mutation does not appear to diminish E1A function.

Human glandular kallikrein (hKLK2, encoding the hK2 protein) is expressed exclusively in the prostate and its expression is up-regulated by androgens primarily by transcriptional activation. Wolf et al. (1992) Molec. Endocrinol. 6:753–762. Morris (1989) Clin. Exp. Pharm. Physiol. 16:345–351; Qui et al. (1990) J. Urol. 144:1550–1556; Young et al. (1992) Biochem. 31:818–824. The levels of hK2 found in various tumors and in the serum of patients with prostate cancer differ substantially from those of PSA and indicate that hK2 antigen may be a significant marker for prostate cancer. Circulating hK2 in different relative proportions to PSA has been detected in the serum of patients with prostate cancer. Charlesworth et al. (1997) Urology 49:487–493. Expression of hK2 has been detected in each of 257 radical prostatectomy specimens analyzed. Darson et al. (1997) *Urology* 49:857–862. The intensity and extent of hK2 expression, detected using specific antibodies, increased from benign epithelium to high-grade prostatic intraepithelial neoplasia (PIN) and adenocarcinoma, whereas PSA and prostate acid phosphatase displayed an inverse pattern of immunoreactivity. Darson et al. (1997). Indeed, it has been reported that a certain percentage of PSA-negative tumors have detectable hK2. Tremblay et al. (1997) *Am. J. Pathol.* 150:455–459.

The activity of the hKLK2 5' promoter has been previously described and a region up to −2256 relative to the transcription start site was previously disclosed. Schedlich et al. (1987) *DNA* 6:429–437. The hKLK2 promoter is androgen responsive and, in plasmid constructs wherein the promoter alone controls the expression of a reporter gene, expression of the reporter gene is increased approximately 10-fold in the presence of androgen. Murtha et al. (1993) *Biochem.* 32:6459–6464. hKLK2 enhancer activity is found within a polynucleotide sequence approximately nt −12,014 to nt −2257 relative to the start of transcription (depicted in SEQ ID NO:3) and, when this sequence is operably linked to an hKLK2 promoter and a reporter gene, transcription of operably-linked sequences in prostate cells increases in the presence of androgen at levels approximately 30- to approximately 100-fold over the level of transcription in the absence of androgen. This induction is generally orientation independent and position independent. Enhancer activity has also been demonstrated in the following regions (all relative to the transcription start site): about nt −3993 to about nt −3643 (nt 8021 to 8371 of SEQ ID NO:3), about nt −4814 to about nt −3643 (nt 7200 to 8371 of SEQ ID NO:3), about nt −5155 to about nt −3387 (nt 6859 to 8627 of SEQ ID NO:3), about nt −6038 to about nt −2394 (nt 5976 to 9620 of SEQ ID NO:3).

Thus, an hKLK2 enhancer can be operably linked to an hKLK2 promoter or a heterologous promoter to form an hKLK2 transcriptional regulatory element (hKLK2-TRE). An hKLK2-TRE can then be operably linked to a heterologous polynucleotide to confer hKLK2-TRE-specific transcriptional regulation on the linked gene, thus increasing its expression.

The rat probasin (PB) gene encodes a nuclear and secreted protein, probasin, that is only expressed in the dorsolateral prostate. Dodd et al. (1983) *J. Biol. Chem.* 258:10731–10737; Matusik et al. (1986) *Biochem. Cell. Biol.* 64: 601–607; and Sweetland et al. (1988) *Mol. Cell. Biochem.* 84: 3–15. The dorsolateral lobes of the murine prostate are considered the most homologous to the peripheral zone of the human prostate, where approximately 68% of human prostate cancers are thought to originate.

A PB-TRE has been shown in an approximately 0.5 kb fragment of sequence upstream of the probasin coding sequence, from about nt −426 to about nt +28 relative to the transcription start site,as depicted in (SEQ ID NO:4). This minimal promoter sequence from the PB gene appears to provide sufficient information to direct development and hormone-regulated expression of an operably linked heterologous gene specifically to the prostate in transgenic mice. Greenberg et al. (1994) *Mol. Endocrinol.* 8:230–239.

Thus, TREs derived from prostate cell specific TREs, including, but not limited to, those described herein, may be used in the present invention to generate stable adenovirus vectors that preferentially replicate in cells in which the TREs are functional, such as cells expressing an AR, particularly cells derived from prostate neoplasia. Accordingly, and by way of example, the invention includes adenovirus vectors in which the first heterologous TRE is a PSA-TRE (e.g., PSE-TRE) and the second heterologous TRE is a PB-TRE, in which the first heterologous TRE is a PB-TRE and the second heterologous TRE is a PSA-TRE (e.g., PSE-TRE), in which the first heterologous TRE is an hKLK2-TRE and the second heterologous TRE is a PSA-TRE (e.g., PSE-TRE), in which the first heterologous TRE is a PSA-TRE (e.g., PSE-TRE) and the second heterologous TRE is an hKLK2-TRE, in which the first heterologous TRE is an hKLK2-TRE and the second heterologous TRE is a PB-TRE, in which the first heterologous TRE is a PB-TRE and the second heterologous TRE is an hKLK2-TRE, as described above. See Examples 1–4, FIG. 2.

In the present invention, replication-competent adenovirus vectors directed at specific target cells may also be generated with the use of TREs that are preferentially functional in the target tumor cells. Non-limiting examples of tumor cell-specific heterologous TREs, and non-limiting examples of respective potential target cells, include TREs from the following genes: α-fetoprotein (AFP) (liver cancer), mucin-like glycoprotein DF3 (MUC1) (breast carcinoma), carcinoembryonic antigen (CEA) (colorectal, gastric, pancreatic, breast, and lung cancers), plasminogen activator urokinase (uPA) and its receptor gene (breast, colon, and liver cancers), E2F1 (cell cycle S-phase specific promoter) (tumors with disrupted retinoblastoma gene function), HER-2/neu (c-erbB2/neu) (breast, ovarian, stomach, and lung cancers).

In the present invention, tumor-specific TREs may be used in conjunction with tissue-specific TREs from the following exemplary genes (tissue in which the TREs are specifically functional are in parentheses): hypoxia responsive element, vascular endothelial growth factor receptor (endothelium), albumin (liver), factor VII (liver), fatty acid synthase (liver), Von Willebrand factor (brain endothelium), alpha-actin and myosin heavy chain (both in smooth muscle), synthetast I (small intestine), Na—K—Cl transporter (kidney). Additional tissue specific TREs are known in the art.

Accordingly, in one embodiment, the cell specific, heterologous TRE is tumor cell specific. Preferably, both heterologous TREs are tumor cell specific and functional in the same cell. In another embodiment, one of the first heterologous TREs is tumor cell specific and the second heterologous TRE is tissue specific, whereby both TREs are function in the same cell.

AFP is an oncofetal protein, the expression of which is primarily restricted to developing tissues of endodermal origin (yolk sac, fetal liver, and gut), although the level of its expression varies greatly depending on the tissue and the developmental stage. AFP is of clinical interest because the serum concentration of AFP is elevated in a majority of hepatoma patients, with high levels of AFP found in patients with advanced disease. The serum AFP levels in patients appear to be regulated by AFP expression in hepatocellular carcinoma but not in surrounding normal liver. Thus, the AFP gene appears to be regulated to hepatoma cell-specific expression.

Cell-specific TREs from the AFP gene have been identified. For example, the cloning and characterization of human AFP-specific enhancer activity is described in Watanabe et al. (1987) *J. Biol. Chem.* 262:4812–4818. The entire 5' AFP flanking region (containing the promoter, putative silencer, and enhancer elements) is contained within approximately 5 kb upstream from the transcription start site (SEQ ID NO:5).

The AFP enhancer region in human is located between about nt −3954 and about nt −3335, relative to the transcription start site of the AFP gene. The human AFP promoter encompasses a region from about nt −174 to about nt +29. Juxtapositioning of these two genetic elements, as depicted in SEQ ID NO:6, yields a fully functional AFP-TRE. Ido et al. (1995) describe a 259 bp promoter fragment (nt −230 to nt +29) that is specific for HCC. *Cancer Res.* 55:3105–3109. The AFP enhancer contains two regions, denoted A and B, located between nt −3954 and nt −3335 relative to the transcription start site. The promoter region contains typical TATA and CAAT boxes. Preferably, the AFP-TRE contains at least one enhancer region. More preferably, the AFP-TRE contains both enhancer regions.

Suitable target cells for adenoviral vectors containing AFP-TREs are any cell type that allow an AFP-TRE to function. Preferred are cells that express, or produce, AFP, including, but not limited to, tumor cells expressing AFP. Examples of such cells are hepatocellular carcinoma cells, gonadal and other germ cell tumors (especially endodermal sinus tumors), brain tumor cells, ovarian tumor cells, acinar cell carcinoma of the pancreas (Kawamoto et al. (1992) *Hepatogastroenterology* 39:282–286), primary gall bladder tumor (Katsuragi et al. (1989) *Rinsko Hoshasen* 34:371–374), uterine endometrial adenocarcinoma cells (Koyama et al. (1996) *Jpn. J. Cancer Res.* 87:612–617), and any metastases of the foregoing (which can occur in lung, adrenal gland, bone marrow, and/or spleen). In some cases, metastatic disease to the liver from certain pancreatic and stomach cancers produce AFP. Especially preferred are hepatocellular carcinoma cells and any of their metastases. AFP production can be measured using assays standard in the art, such as RIA, ELISA or Western blots (immunoassays) to determine levels of AFP protein production or Northern blots to determine levels of AFP mRNA production. Alternatively, such cells can be identified and/or characterized by their ability to activate transcriptionally an AFP-TRE (i.e., allow an AFP-TRE to function).

The protein urokinase plasminogen activator (uPA) and its cell surface receptor, urokinase plasminogen activator receptor (uPAR), are expressed in many of the most frequently occurring neoplasia and appear to represent important proteins in cancer metastasis. Both proteins are implicated in breast, colon, prostate, liver, renal, lung and ovarian cancer. Transcriptional regulatory elements that regulate uPA and uPAR transcription have been extensively studied. Riccio et al. (1985) *Nucleic Acids Res.* 13:2759–2771; Cannio et al., (1991) *Nucleic Acids Res.* 19:2303–2308.

Thus, cell-specific TREs, including but not limited to those described herein, could be used in the present invention to generate stable adenovirus vectors that preferentially replicate in cells in which the TREs are functional, such as cells derived from liver neoplasia. In one embodiment, the invention includes adenovirus vectors wherein at least one of the heterologous TREs are liver cell-specific. Accordingly, and by way of example, the invention includes adenovirus vectors in which the first heterologous TRE is an AFP-TRE and the second heterologous TRE is an uPA-TRE, in which the first heterologous TRE is an uPA-TRE and the second heterologous TRE is an AFP-TRE, in which the first heterologous TRE is an AFP-TRE and the second heterologous TRE is an albumin-TRE, in which the first heterologous TRE is an albumin-TRE and the second heterologous TRE is an AFP-TRE, as described above.

CEA is a 180,000-Dalton glycoprotein tumor-associated antigen present on endodermally-derived neoplasia of the gastrointestinal tract, such as colorectal, gastric (stomach) and pancreatic cancer, as well as other adenocarcinomas such as breast and lung cancers. CEA is of clinical interest because circulating CEA can be detected in the great majority of patients with CEA-positive tumors. In lung cancer, about 50% of total cases have circulating CEA, with high concentrations of CEA (greater than 20 ng/ml) often detected in adenocarcinomas. Approximately 50% of patients with gastric carcinoma are serologically positive for CEA.

The 5' upstream flanking sequence of the CEA gene has been shown to confer cell-specific activity. The CEA promoter region, approximately the first 424 nucleotides upstream of the translational start site in the 5' flanking region of the gene, was shown to confer cell-specific activity when the region provided higher promoter activity in CEA-producing cells than in non-producing HeLa cells. Schrewe et al. (1990) *Mol. Cell. Biol.* 10:2738–2748. In addition, cell-specific enhancer regions have been found. WO/95/14100. The entire 5' CEA flanking region (containing the promoter, putative silencer, and enhancer elements) appears to be contained within approximately 14.5 kb upstream from the transcription start site. Richards et al. (1995); WO 95/14100. Further characterization of the 5' flanking region of the CEA gene by Richards et al. (1995) indicated two upstream regions, −13.6 to −10.7 kb or −6.1 to −4.0 kb, when linked to the multimerized promoter resulted in high-level and selective expression of a reporter construct in CEA-producing LoVo and SW1463 cells. Richards et al. (1995) also localized the promoter region to nt −90 and nt +69 relative to the transcriptional start site, with region nt −41 to nt −18 as essential for expression. WO95/14100 describes a series of 5' flanking CEA fragments which confer cell-specific activity, such as about nt −299 to about nt +69; about nt −90 to about nt +69; nt −14,500 to nt −10,600; nt −13,600 to nt −10,600, nt −6100 to nt −3800. In addition, cell specific transcription activity is conferred on an operably linked gene by the CEA fragment from nt −402 to nt +69, depicted in (SEQ ID NO:7). Any CEA-TREs used in the present invention are derived from mammalian cells, including but not limited to, human cells. Thus, any of the CEA-TREs may be used in the invention as long as requisite desired functionality is displayed in the adenovirus vector. The cloning and characterization of CEA sequences have been described in the literature and are thus made available for practice of this invention and need not be described in detail herein.

The protein product of the MUC1 gene (known as mucin or MUC1 protein; episialin; polymorphic epithelial mucin or PEM; EMA; DF3 antigen; NPGP; PAS-O; or CA15.3 antigen) is normally expressed mainly at the apical surface of epithelial cells lining the glands or ducts of the stomach, pancreas, lungs, trachea, kidney, uterus, salivary glands, and mammary glands. Zotter et al. (1988) *Cancer Rev.* 11–12: 55–101; and Girling et al. (1989) *Int. J. Cancer* 43: 1072–1076. However, mucin is overexpressed in 75–90% of human breast carcinomas. Kufe et al. (1984) *Hybridoma* 3: 223–232. For reviews, see Hilkens (1988) *Cancer Rev.* 11–12: 25–54; and Taylor-Papadimitriou, et al. (1990) *J. Nucl. Med. Allied Sci.* 34: 144–150. Mucin protein expression correlates with the degree of breast tumor differentiation. Lundy et al. (1985) *Breast Cancer Res. Treat.* 5: 269–276. This overexpression appears to be controlled at the transcriptional level.

Overexpression of the MUC1 gene in human breast carcinoma cells MCF-7 and ZR-75-1 appears to be regulated at the transcriptional level. Kufe et al. (1984); Kovarik (1993) *J. Biol. Chem.* 268:9917–9926; and Abe et al. (1990) *J. Cell. Physiol.* 143: 226–231. The regulatory sequences of the MUC1 gene have been cloned, including the approximately 0.9 kb upstream of the transcription start site which contains a TRE that appears to be involved in cell-specific transcription, depicted in SEQ ID NO:8. Abe et al. (1993) *Proc. Natl. Acad. Sci. USA* 90: 282–286; Kovarik et al. (1993); and Kovarik et al. (1996) *J. Biol. Chem.* 271:18140–18147.

Any MUC1-TREs used in the present invention are derived from mammalian cells, including but not limited to, human cells. Preferably, the MUC1-TRE is human. In one embodiment, the MUC1-TRE may contain the entire 0.9 kb 5' flanking sequence of the MUC1 gene. In other embodiments, the MUC1-TREs comprise the following sequences (relative to the transcription start site of the MUC1 gene): about nt −725 to about nt +31, nt −743 to about nt +33, nt −750 to about nt +33, and nt −598 to about nt +485 (operably-linked to a promoter).

The c-erbB2/neu gene (HER-2/neu or HER) is a transforming gene that encodes a 185 kD epidermal growth factor receptor-related transmembrane glycoprotein. In humans, the c-erbB2/neu protein is expressed during fetal development, however, in adults, the protein is weakly detectable (by immunohistochemistry) in the epithelium of many normal tissues. Amplification and/or over-expression of the c-erbB2/neu gene has been associated with many human cancers, including breast, ovarian, uterine, prostate, stomach and lung cancers. The clinical consequences of the c-erbB2/neu protein over-expression have been best studied in breast and ovarian cancer. c-erbB2/neu protein overexpression occurs in 20 to 40% of intraductal carcinomas of the breast and 30% of ovarian cancers, and is associated with a poor prognosis in subcategories of both diseases. Human, rat and mouse c-erbB2/neu TREs have been identified and shown to confer c-erbB2/neu expressing cell specific activity. Tal et al. (1987) *Mol. Cell. Biol.* 7:2597–2601; Hudson et al. (1990) *J. Biol. Chem.* 265:4389–4393; Grooteclaes et al. (1994) *Cancer Res.* 54:4193–4199; Ishii et al. (1987) *Proc. Natl. Acad. Sci. USA* 84:4374–4378; Scott et al. (1994) *J. Biol. Chem.* 269:19848–19858.

Thus, TREs derived from breast cell-specific TREs, including, but not limited to, those described herein, may be used in the present invention to generate stable adenovirus vectors that preferentially replicate in cells in which the TREs are functional, particularly cells derived from breast neoplasia. In one embodiment, the invention includes adenovirus vectors wherein the heterologous TREs are breast cell-specific. Accordingly, and by way of example, the invention includes adenovirus vectors in which the first heterologous TRE is a CEA-TRE and the second heterologous TRE is a MUC1-TRE, in which the first heterologous TRE is a MUC1-TRE and the second heterologous TRE is a CEA-TRE, in which the first heterologous TRE is a MUC1-TRE and the second heterologous TRE is a HER-TRE, in which the first heterologous TRE is a HER-TRE and the second heterologous TRE is an MUC1-TRE, in which the first heterologous TRE is a MUC1-TRE and the second heterologous TRE is a uPA-TRE, in which the first heterologous TRE is a uPA-TRE and the second heterologous TRE is a MUC1-TRE, in which the first heterologous TRE is a uPA-TRE and the second heterologous TRE is an HER-TRE, in which the first heterologous TRE is an HER-TRE and the second heterologous TRE is a uPA-TRE, as described above.

Thus, TREs derived from colon cell-specific TREs, including, but not limited to, those described herein, may be used in the present invention to generate stable adenovirus vectors that preferentially replicate in cells in which the TREs are functional, particularly cells derived from colon neoplasia. In one embodiment, the invention includes adenovirus vectors wherein the heterologous TREs are colon cell-specific. Accordingly, and by way of example, the invention includes adenovirus vectors in which the first heterologous TRE is a CEA-TRE and the second heterologous TRE is a uPA-TRE, in which the first heterologous TRE is a uPA-TRE and the second heterologous TRE is a CEA-TRE, as described above.

As described above, some of the exemplary TREs are specific for more than one cell-type and thus, more than one type of neoplasia. Accordingly, adenovirus vectors of the present invention, as exemplified above, may be useful in the treatment of more than one type of neoplasm, as can be determined by the information provided herein.

The TREs listed above are provided as non-limiting examples of TREs that would function in the instant invention. Additional cell-specific TREs are known in the art, as are methods to identify and test cell specificity of suspected TREs. Further, and as noted above, the invention does not require that the TREs be derived from different genes. As long as the TRE sequences are sufficiently different, and the requisite functionality is diplayed, the different TREs may be derived from the same gene.

For example, activity of a TRE can be determined as follows. A TRE polynucleotide sequence or set of such sequences can be generated using methods known in the art, such as chemical synthesis, site-directed mutagenesis, PCR, and/or recombinant methods. The sequence(s) to be tested can be inserted into a vector containing a promoter (if no promoter element is present in the TRE) and an appropriate reporter gene encoding a reporter protein, including, but not limited to, chloramphenicol acetyl transferase (CAT), β-galactosidase (encoded by the lacZ gene), luciferase (encoded by the luc gene), alkaline phosphatase, green fluorescent protein, and horse radish peroxidase. Such vectors and assays are readily available, from, inter alia, commercial sources. Plasmids thus constructed are transfected into a suitable host cell to test for expression of the reporter gene as controlled by the putative TRE using transfection methods known in the art, such as calcium phosphate precipitation, electroporation, liposomes (lipofection), and DEAE dextran.

After introduction of the TRE-reporter gene construct into a host cell under appropriate conditions, TRE activity may be measured by detection and/or quantitation of reporter gene-derived mRNA or protein product. The reporter gene protein can be detected directly (e.g., immunochemically) or through its enzymatic activity, if any, with an appropriate substrate. Generally, to determine cell specific activity of a TRE, the TRE-reporter gene constructs are introduced into a variety of cell types. The amount of TRE activity is determined in each cell type and compared to that of a reporter gene construct without the TRE. A TRE is cell specific when it is preferentially functional in a specific type of cell over a different type of cell.

For example, the specificity of PB-TRE activity for prostate cell that express the androgen receptor (AR) was demonstrated as follows. The region of the PB 5'-flanking DNA (nt −426 to nt +28) (SEQ ID NO:4) including the endogenous promoter sequences was inserted upstream of the firefly luciferase gene to generate a chimeric PB-TRE-luc plasmid. Cationic-mediated, transient transfection of LNCaP (PSA-producing and AR-producing prostate carcinoma cells) and PC-3 (PSA-deficient and AR-deficient prostate carcinoma cells) cells was performed. The results showed that LNCaP cells transfected with PB-TRE-luc had approximately 400 times more activity than untransfected cells, indicating that the PB-TRE was intact. Further, the overall luciferase activity recovered in the cellular extracts of transfected LNCaP cells was about 30–40-fold higher than that measured in the cellular extracts of transfected PC-3 cells. Thus, the results indicate that PB-TRE expression is preferentially functional in PSA-producing, AR-producing prostate carcinoma cells as compared to PSA-deficient, AR-deficient prostate carcinoma cells and that PB-TRE is capable of mediating specific expression in cells producing the androgen receptor.

(b) Exemplary Genes Under Transcriptional Control of the Heterologous TREs

Any of the various serotypes of adenovirus can be used, such as Ad2, Ad5, Ad12, and Ad40. For purposes of illustration the serotype adenovirus 5 (Ad5) is exemplified herein.

In some embodiments, a cell specific, heterologous TRE is used to control transcription of an adenovirus gene and a second heterologous TRE, different from (i.e., not the same as) the first heterologous TRE, is used to control transcription of a second gene to provide an adenovirus vector so that replication-competence is preferentially achievable in target cells which allow for function of the cell-specific TRE. In addition, the two heterologous TREs are functional in the target cell. Preferably, the first adenovirus gene is essential for adenoviral replication, even more preferably, both genes are essential for adenoviral replication. Preferably, at least one of the genes is an early gene, such as E1A, E1B, E2, or E4. (E3 is not essential for viral replication.) Preferably, both genes under control of the heterologous TREs are early genes. More preferably, the early gene under cell-specific TRE control is E1A and/or E1B. Examples 1, 2 and 5 provide a more detailed description of such constructs.

The E1A gene is expressed immediately after viral infection (0–2 hours) and before any other viral genes. E1A protein acts as a trans-acting positive-acting transcriptional regulatory factor, and is required for the expression of the other early viral genes E1B, E2, E3, E4, and the promoter-proximal major late genes. Despite the nomenclature, the promoter proximal genes driven by the major late promoter are expressed during early times after Ad5 infection. Flint (1982) *Biochem. Biophys. Acta* 651:175–208; Flint (1986) *Advances Virus Research* 31:169–228; Grand (1987) *Biochem. J.* 241:25–38. In the absence of a functional E1A gene, viral infection does not proceed, because the gene products necessary for viral DNA replication are not produced. Nevins (1989) *Adv. Virus Res.* 31:35–81. The transcription start site of Ad5 E1A is at nt 498 and the ATG start site of the E1A protein is at nt 560 in the virus genome.

The E1B protein functions in trans and is necessary for transport of late mRNA from the nucleus to the cytoplasm. Defects in E1B expression result in poor expression of late viral proteins and an inability to shut off host cell protein synthesis. The promoter of E1B has been implicated as the defining element of difference in the host range of Ad40 and Ad5: clinically Ad40 is an enterovirus, whereas Ad5 causes acute conjunctivitis. Bailey et al. (1993) *Virology* 193:631; Bailey et al. (1994) *Virology* 202:695–706. The E1B promoter of Ad5 consists of a single high-affinity recognition site for Sp1 and a TATA box.

Accordingly, in one embodiment, the adenovirus E1A gene is under transcriptional control of the cell specific, heterologous TRE. In another embodiment, the adenovirus E1B gene is under transcriptional control of the cell specific, heterologous TRE. In another embodiment, both the adenovirus E1A and E1B genes are under transcriptional control of two different heterologous TREs, preferably both TREs are cell specific.

The E2 region of adenovirus codes for proteins related to replication of the adenoviral genome, including the 72 kD DNA-binding protein, the 80 kD precursor terminal protein and the viral DNA polymerase. The E2 region of Ad5 is transcribed in a rightward orientation from two promoters, termed E2 early and E2 late, mapping at 76.0 and 72.0 map units, respectively. While the E2 late promoter is transiently active during late stages of infection and is independent of the E1A transactivator protein, the E2 early promoter is crucial during the early phases of viral replication.

The E2 early promoter, mapping in Ad5 from 27050–27150, consists of a major and a minor transcription initiation site, the latter accounting for about 5% of the E2 transcripts, two non-canonical TATA boxes, two E2F transcription factor binding sites and an ATF transcription factor binding site. For a detailed review of the E2 promoter architecture see Swaminathan et al., *Curr. Topics in Micro. and Imm.* (1995) 199 part 3:177–194.

The E2 late promoter overlaps with the coding sequences of a gene encoded by the counterstrand and is therefore not amenable for genetic manipulation. However, the E2 early promoter overlaps only for a few base pairs with sequences coding for a 33 kD protein on the counterstrand. Notably, the SpeI restriction site (Ad5 position 27082) is part of the stop codon for the above mentioned 33 kD protein and conveniently separates the major E2 early transcription initiation site and TATA-binding protein site from the upstream transcription factor binding sites E2F and ATF. Therefore, insertion of a heterologous TRE having SpeI ends into the SpeI site in the plus strand would disrupt the endogenous E2 early promoter of Ad5 and should allow TRE-regulated expression of E2 transcripts.

The E4 gene has a number of transcription products. The E4 region codes for two polypeptides which are responsible for stimulating the replication of viral genomic DNA and for stimulating late gene expression. The protein products of open reading frames (ORFs) 3 and 6 can both perform these functions by binding the 55-kD protein from E1B and heterodimers of E2F-1 and DP-1. The ORF 6 protein requires interaction with the E1B 55-kD protein for activity while the ORF 3 protein does not. In the absence of functional protein from ORF 3 and ORF 6, plaques are produced with an efficiency less than $10^{-6}$ that of wild type virus. To restrict further the viral replication to target cells, E4 ORFs 1–3 can be deleted, making viral DNA replication and late gene synthesis dependent on E4 ORF 6 protein. By combining such a mutant with sequences in which the E1B region is regulated by a target cell-specific TRE, a virus can be obtained in which both the E1B function and E4 function are dependent on the target cell-specific TRE driving E1B.

The major late genes relevant to the subject invention are L1, L2 and L3, which encode proteins of the Ad5 virus virion. All of these genes (typically coding for structural proteins) are probably required for adenoviral replication. The late genes are all under the control of the major late promoter (MLP), which is located in Ad5 at +5986 to +6048.

In one embodiment, the adenovirus E4 gene is under transcriptional control of the cell specific, heterologous TRE. In another embodiment, an adenovirus late gene is under transcriptional control of the cell specific, heterologous TRE. In another embodiment, one early gene and one late gene are under transcriptional control of differrent heterologous TREs.

In addition to conferring selective cytotoxic and/or cytolytic activity by virtue of preferential replication competence in cells which allow function of the heterologous TREs, the adenovirus vectors of this invention can further include a heterologous polynucleotide (transgene) under the control of a heterologous TRE. In this way, various genetic capabilities may be introduced into target cells. For example, in certain instances, it may be desirable to enhance the degree and/or rate of cytotoxic activity, due to, for example, the relatively refractory nature or particular aggressiveness of the target cell. This could be accomplished by coupling the cell-specific replicative cytotoxic activity with cell-specific expression of, for example, HSV-tk and/or cytosine deaminase (cd), which renders cells capable of metabolizing 5-fluorocytosine (5-FC) to the chemotherapeutic agent 5-fluorouracil (5-FU). Using these types of transgenes may also confer a bystander effect.

Other desirable transgenes that may be introduced via an adenovirus vector(s) include genes encoding cytotoxic proteins, such as the A chains of diphtheria toxin, ricin or abrin (Palmiter et al. (1987) *Cell* 50: 435; Maxwell et al. (1987) *Mol. Cell. Biol.* 7: 1576; Behringer et al. (1988) *Genes Dev.* 2: 453; Messing et al. (1992) *Neuron* 8: 507; Piatak et al. (1988) *J. Biol. Chem.* 263: 4937; Lamb et al. (1985) *Eur. J. Biochem.* 148: 265; Frankel et al. (1989) *Mol. Cell. Biol.* 9: 415), genes encoding a factor capable of initiating apoptosis, sequences encoding antisense transcripts or ribozymes, which among other capabilities may be directed to mRNAs encoding proteins essential for proliferation, such as structural proteins, or transcription factors; viral or other pathogenic proteins, where the pathogen proliferates intracellularly, genes that encode an engineered cytoplasmic variant of a nuclease (e.g. RNase A) or protease (e.g. awsin, papain, proteinase K, carboxypeptidase, etc.), or encode the Fas gene, and the like. Other genes of interest include potential therapeutic genes such as cytokines, antigens, transmembrane proteins, and the like, such as IL-1, -2, -6, -12, GM-CSF, G-CSF, M-CSF, IFN-α, -β, -γ, TNF-α, -β, TGF-α, -β, NGF, and the like. The positive effector genes could be used in an early phase, followed by cytotoxic activity due to replication.

In some embodiments, the adenovirus death protein (ADP), encoded within the E3 region, is maintained (i.e., contained) in the adenovirus vector. The ADP gene, under control of the major late promoter (MLP), appears to code for a protein (ADP) that is important in expediting host cell lysis. Tollefson et al. (1996) *J. Virol.* 70(4):2296; Tollefson et al. (1992) *J. Virol.* 66(6):3633. Thus, adenoviral vectors containing the ADP gene may render the adenoviral vector more potent, making possible more effective treatment and/or a lower dosage requirement.

Accordingly, the invention provides adenovirus vectors in which a first adenovirus gene is in under transcriptional control of a first heterologous cell-specific TRE and a polynucleotide sequence encoding an ADP under control of a second heterologous TRE, which is different from the first TRE but functional in the same cell as the first TRE, preferably the first adenovirus gene is essential for replication. A DNA sequence encoding an ADP and the amino acid sequence of an ADP are depicted in SEQ ID NO:9 and SEQ ID NO:10, respectively. Briefly, an ADP coding sequence is obtained preferably from Ad2 (since this is the strain in which ADP has been more fully characterized) using techniques known in the art, such as PCR. Preferably, the Y leader (which is an important sequence for correct expression of late genes) is also obtained and ligated to the ADP coding sequence. The ADP coding sequence (with or without the Y leader) can then be introduced into the adenoviral genome, for example, in the E3 region (where the ADP coding sequence will be driven by the MLP). The ADP coding sequence could also be inserted in other locations of the adenovirus genome, such as the E4 region. Alternatively, the ADP coding sequence could be operably linked to a heterologous TRE, including, but not limited to, another viral TRE, a tissue specific TRE such as that of AFP, CEA, hKLK2, MUC1, PSE and PB.

It is understood that the present invention does not exclude adenovirus vectors containing additional genes under control of the heterologous TREs. Accordingly, the invention provides adenoviral vectors comprising a third gene under transcriptional control of a third heterologous TRE where all of the heterologous TREs are different from each other in polynucleotide sequence but all are functional in the same cell. Preferably, the third gene is one that contributes to cytotoxicity (whether direct and/or indirect), more preferably one that contributes to and/or enhances cell death, and even more preferably the third gene is essential from adenovirus replication. Preferably the third heterologous TRE is target cell specific. For example, an adenovirus vector may contain a PB-TRE, a PSE-TRE and an hKLK2-TRE, each prostate cell specific and each controlling the transcription of a different gene.

As is known in the art and described herein, the ability of enhancers to increase transcription of an operably linked gene is independent of its orientatoin and distance relative to the gene. Accordingly, the invention provides adenoviral vectors comprising at least an additional gene (beyond the first and the second genes) under transcriptional control of the second heterologous TRE. Preferably, the additional gene is one that contributes to cytotoxicity (whether direct and/or indirect), more preferably one that enhances cell death, and even more preferably the third gene is essential from adenovirus replication.

(c) Delivery of Adenoviral Vectors to Cells

The adenoviral vectors can be used in a variety of forms, including, but not limited to, naked polynucleotide (usually DNA) constructs; polynucleotide constructs complexed with agents to facilitate entry into cells, such as cationic liposomes or other compounds such as polylysine; packaged into infectious adenovirus particles (which may render the adenoviral vector(s) more immunogenic); packaged into other particulate viral forms such as HSV or AAV; complexed with agents to enhance or dampen an immune response; complexed with agents that facilitate in vivo transfection, such as DOTMA™, DOTAP™, and polyamines.

If an adenoviral vector is packaged into an adenovirus, the adenovirus itself may be selected to further enhance targeting. For example, adenovirus fibers mediate primary contact with cellular receptor(s) aiding in tropism. See, e.g., Amberg et al. (1997) *Virol.* 227:239–244. If a particular subgenus of an adenovirus serotype displayed tropism for a target cell type and/or reduced affinity for non-target cell types, such subgenus (or subgenera) could be used to further increase cell-specificity of cytotoxicity and/or cytolysis.

The adenoviral vectors may be delivered to the target cell in a variety of ways, including, but not limited to, liposomes, general transfection methods that are well known in the art (such as calcium phosphate precipitation and electroporation), and direct injection, and intravenous infusion. The means of delivery will depend in large part on the particular adenoviral vector (including its form) as well as the type and location of the target cells (i.e., whether the cells are in vitro or in vivo).

If used in a packaged adenovirus, adenovirus vectors may be administered in an appropriate physiologically acceptable carrier at a dose of about $10^4$ to about $10^{14}$. The multiplicity of infection will generally be in the range of about 0.001 to 100. If administered as a polynucleotide construct (i.e., not packaged as a virus) about 0.01 μg to 1000 μg of an adenoviral vector can be administered. The adenoviral vectors may be administered one or more times, depending upon the intended use and the immune response potential of the host or may be administered as multiple simultaneous injections. If an immune response is undesirable, the immune response may be diminished by employing a variety of immunosuppressants, so as to permit repetitive administration, without a strong immune response. If packaged as another viral form, such as HSV, an amount to be administered is based on standard knowledge about that particular virus (which is readily obtainable from, for example, published literature) and can be determined empirically.

Host Cells

The present invention also provides host cells comprising (i.e., transformed with) the adenoviral vectors described herein. Both prokaryotic and eukaryotic host cells can be used as long as sequence requisite for maintenance in that host, such as appropriate replication origin(s), are present. For convenience, selectable markers are also provided. Prokaryotic host include bacterial cells, for example, *E. coli* and mycobacteria. Among eukaryotic host cells are yeast, insect, avian, amphibian, plant and mammalian host cells. Host systems are known in the art and need not be described in detail herein. Suitable host cells also include any cells that produce proteins and other factors necessary for expression of the gene under control of the heterologous TREs, such factors necessary for said expression are produced naturally or recombinantly.

Suitable host cells for the adenovirus include any eukaryotic cell type that allows function of the heterologous TREs, preferably mammalian. For example, if the heterologous TRE(s) used is prostate cell-specific, the cells are preferably prostate cells, for example LNCaP cells. The prostate cells used may or may not be producing an androgen receptor, depending on whether the promoter used is androgen-inducible. If an androgen-inducible promoter is used, non-androgen receptor producing cells, such as HLF, HLE, and 3T3 and the non-AR-producing prostate cancer cells PC3 and DU145 can be used, provided an androgen receptor-encoding expression vector is introduced into the cells along with the adenovirus. If the heterologous TRE(s) used is derived from the AFP gene, for example, suitable host cells include any cell type that produces AFP, including but not limited to, Hep3B, HepG2, HuH7, HuH1/C12. Activity of a given TRE in a given cell can be assessed by measuring the level of expression of a operably-linked reporter gene using standard assays. The comparison of expression between cells in which the TRE is suspected of being functional and the control cell indicates the presence or absence of transcriptional enhancement.

Comparisons between or among various TREs can be assessed by measuring and comparing levels of expression within a single cell line. It is understood that absolute transcriptional activity of a TRE will depend on several factors, such as the nature of the target cell, delivery mode and form of a TRE, and the coding sequence that is to be selectively transcriptionally activated. To compensate for various plasmid sizes used, activities can be expressed as relative activity per mole of transfected plasmid. Alternatively, the level of transcription (i.e., mRNA) can be measured using standard Northern analysis and hybridization techniques. Levels of transfection (i.e., transfection efficiencies) are measured by co-transfecting a plasmid encoding a different reporter gene under control of a different TRE, such as the CMV immediate early promoter. This analysis can also indicate negative regulatory regions, i.e., silencers.

Compositions

The present invention also includes compositions, including pharmaceutical compositions, containing the adenoviral vectors described herein. Such compositions are useful for administration in vivo, for example, when measuring the degree of transduction and/or effectiveness of cell killing in an individual. Preferably, these compositions further comprise a pharmaceutically acceptable excipient. These compositions, which can comprise an effective amount of an adenoviral vector of this invention in a pharmaceutically acceptable excipient, are suitable for systemic administration to individuals in unit dosage forms, sterile parenteral solutions or suspensions, sterile non-parenteral solutions or oral solutions or suspensions, oil in water or water in oil emulsions and the like. Formulations for parenteral and nonparenteral drug delivery are known in the art and are set forth in *Remington's Pharmaceutical Sciences*, 18$^{th}$ Edition, Mack Publishing (1990). Compositions also include lyophilized and/or reconstituted forms of the adenoviral vectors (including those packaged as a virus, such as adenovirus) of the invention.

Kits

The present invention also encompasses kits containing an adenoviral vector of this invention. These kits can be used for diagnostic and/or monitoring purposes, preferably monitoring. Procedures using these kits can be performed by clinical laboratories, experimental laboratories, medical practitioners, or private individuals. Kits embodied by this invention allow someone to detect the presence of target cells in a suitable biological sample, such as biopsy specimens.

The kits of the invention comprise an adenoviral vector described herein in suitable packaging. The kit may optionally provide additional components that are useful in the procedure, including, but not limited to, buffers, developing reagents, labels, reacting surfaces, means for detection, control samples, instructions, and interpretive information.

Preparation of the Adenovirus Vectors of the Invention

The adenovirus vectors of this invention can be prepared using recombinant techniques that are standard in the art. Generally, heterologous TREs are inserted 5' to the adenoviral genes of interest, preferably one or more early genes (although late gene(s) may be used). Heterologous TREs can be prepared using oligonucleotide synthesis (if the sequence is known) or recombinant methods (such as PCR and/or restriction enzymes). Convenient restriction sites, either in the natural adeno-DNA sequence or introduced by methods such as PCR or site-directed mutagenesis, provide an insertion site for the heterologous TREs. Accordingly, convenient restriction sites for annealing (i.e., inserting) heterologous TREs can be engineered onto the 5' and 3' ends of the heterologous TRE using standard recombinant methods, such as PCR.

Polynucleotides used for making adenoviral vectors of this invention may be obtained using standard methods in the art such as chemical synthesis recombinant methods and/or obtained from biological sources.

Adenovirus vectors containing all replication-essential elements, with the desired elements (e.g., E1A) under control of heterologous TREs, are conveniently prepared by homologous recombination or in vitro ligation of two plasmids, one providing the left-hand portion of adenovirus and the other providing the right-hand portion. The resultant adenovirus vector contains at least two different heterologous TREs, with at least one of the heterologous TREs cell-specific and one adenovirus gene under control of a first heterologous TRE and a second gene under control of a second heterologous TRE. If homologous recombination is used, the two plasmids should share at least about 500 bp of sequence overlap. Each plasmid, as desired, may be independently manipulated, followed by cotransfection in a competent host, providing complementing genes as appropriate, or the appropriate transcription factors for initiation of transcription from the heterologous TREs for propagation of the adenovirus. Plasmids are generally introduced into a suitable host cell such as 293 cells using appropriate means of transduction, such as cationic liposomes. Alternatively, in vitro ligation of the right and left-hand portions of the adenovirus genome can be used to construct recombinant adenovirus derivative containing all the replication-essential portions of adenovirus genome. Berkner et al. (1983) *Nucleic Acid Research* 11:6003–6020; Bridge et al. (1989) *J. Virol.* 63:631–638.

For convenience, plasmids are available that provide the necessary portions of adenovirus. Plasmid pXC.1 (McKinnon (1982) *Gene* 19:33–42) contains the wild-type left-hand end of Ad5, from Adenovirus 5 nt 22 to 5790. pBHG10 (Bett et al. (1994) *Proc. Natl. Acad. Sci. USA* 91:8802–8806; Microbix Biosystems Inc., Toronto) provides the right-hand end of Ad5, with a deletion in E3. The deletion in E3 provides room in the virus to insert a 3-kb of TRE sequence or transgene sequence without deleting the endogenous enhancer-promoter. The gene for E3 is located on the opposite strand from E4 (r-strand). pBHG11 [Bett et al. (1994)] provides an even larger E3 deletion (an additional 0.3 kb is deleted).

For manipulation of the early genes, the transcription start site of AdS E1A is at nt 498 and the ATG start site of this gene's coding segment is at nt 560 in the virus genome. This region can be used for insertion of a heterologous TRE. A restriction site may be introduced by employing PCR, where the primer that is employed may be limited to the Ad5 genome, or may involve a portion of the plasmid carrying the Ad5 genomic DNA. For example, where pBR322 is used, the primers may use the EcoRI site in the pBR322 backbone and the XbaI site at nt 1339 of Ad5. By carrying out the PCR in two steps, where overlapping primers at the center of the region introduce a 30 sequence change resulting in a unique restriction site, one can provide for insertion of a heterologous TRE at that site.

A similar strategy may be used for insertion of a heterologous TRE to regulate E1B. The E1B promoter of Ad5 consists of a single high-affinity recognition site for Sp1 and a TATA box. This region extends from Ad5 nt 1636 to 1701. By insertion of a cell-specific, heterologous TRE in this region, one can provide for cell-specific transcription of the E1B gene. By employing the left-hand region modified with a cell-specific TRE regulating E1A as the template for introducing a second, different cell-specific TRE to regulate E1B, the resulting adenovirus vector will be dependent upon the cell-specific transcription factors for expression of both E1A and E1B. Examples 1, 2 and 5 provide a more detailed description of how such constructs can be prepared.

Similarly, a heterologous TRE may be inserted upstream of the E2 gene to make its expression cell-specific. The E2 early promoter, mapping in Ad5 from 27050–27150, consists of a major and a minor transcription initiation site, the latter accounting for about 5% of the E2 transcripts, two non-canonical TATA boxes, two E2F transcription factor binding sites and an ATF transcription factor binding site (for a detailed review of the E2 promoter architecture see Swaminathan et al., *Curr. Topics in Microbiol. and Immunol.* (1995) 199 part 3:177–194).

The E2 late promoter overlaps with the coding sequences of a gene encoded by the counterstrand and is therefore not amenable to genetic manipulation. However, the E2 early promoter overlaps only for a few base pairs with sequences coding for a 33-kD protein on the counterstrand. Notably, the SpeI restriction site (Ad5 position 27082) is part of the stop codon for the above mentioned 33 kD protein and conveniently separates the major E2 early transcription initiation site and TATA-binding protein site from the upstream transcription factor biding sites E2F and ATF. Therefore, insertion of a heterologous TRE having SpeI ends into the SpeI site in the plus-strand would disrupt the endogenous E2 early promoter of Ad5 and should allow TRE regulated expression of E2 transcripts.

For E4, one must use the right hand portion of the adenovirus genome. The E4 transcription start site is predominantly at nt 35609, the TATA box at nt 35638 and the first AUG/CUG of ORF1 is at nt 35532. Virtanen et al. (1984) *J.Virol.* 51: 822–831. Using any of the above strategies for the other genes, a heterologous TRE may be introduced upstream from the transcription start site. For the construction of mutants in the E4 region, the co-transfection and homologous recombination are performed in W162 cells (Weinberg et al. (1983) *Proc. Natl. Acad. Sci. USA* 80:5383–5386) which provide E4 proteins in trans to complement defects in synthesis of these proteins.

Methods of packaging adenovirus polynucleotides into adenovirus particles are known in the art and are described in the Examples.

Methods Using the Adenovirus Vectors of the Invention

The subject vectors can be used for a wide variety of purposes, which will vary with the desired or intended result. Accordingly, the present invention includes methods using the adenoviral vectors described above. In one embodiment, methods for using adenovirus vectors comprise introducing an adenovirus vector into a cell, preferably a eukaryotic cell, more preferably a mammalian cell.

In one embodiment, methods for using adenovirus vectors comprise introducing an adenovirus vector into a target cell, preferably a neoplastic cell. In another embodiment, methods for using adenovirus vectors comprise introducing an adenovirus vector into a prostate cell. In another embodiment, methods for using adenovirus vectors comprise introducing an adenovirus vector into a liver cell. In another embodiment, methods for using adenovirus vectors comprise introducing an adenovirus vector into a breast cancer cell. In another embodiment, methods for using adenovirus vectors comprise introducing an adenovirus vector into a colon cancer cell.

In one embodiment, methods are provided for conferring selective cytotoxicity in cells which allow function of the target cell-specific TRE, comprising contacting cells with an adenovirus vector described herein, such that the adenovirus vector(s) enters, i.e., transduces the cell(s). Cytotoxicity can be measured using standard assays in the art, such as dye exclusion, $^3$H-thymidine incorporation, and/or lysis. See Example 3, FIG. 3.

In another embodiment, methods are provided for propagating an adenovirus specific for cells which allow function of the heterologous TREs, preferably eukaryotic cells, more preferably mammalian cells. These methods entail combining an adenovirus vector with mammalian cells which allow function of the heterologous TREs, whereby said adenovirus is propagated.

Another embodiment provides methods of killing cells that allow a heterologous TRE to function comprising combining the mixture of cells with an adenovirus vector of the present invention. The mixture of cells is generally a mixture of cancerous cells in which the heterologous TREs are functional and normal cells, and can be an in vivo mixture or in vitro mixture.

The invention also includes methods for detecting cells in which the heterologous TREs are functional in a biological sample. These methods are particularly useful for monitoring the clinical and/or physiological condition of an individual (i.e., mammal), whether in an experimental or clinical setting. For these methods, cells of a biological sample are contacted with an adenovirus vector, and replication of the adenoviral vector is detected. A suitable biological sample is one in which target cells may be or are suspected to be present. Generally, in mammals, a suitable clinical sample is one in which target cancerous cells are suspected to be present. Such cells can be obtained, for example, by needle biopsy or other surgical procedure. Cells to be contacted may be treated to promote assay conditions such as selective enrichment and/or solubilization. In these methods, target cells can be detected using in vitro assays that detect proliferation, which are standard in the art. Examples of such standard assays include, but are not limited to, burst assays (which measure virus yields) and plaque assays (which measure infectious particles per cell). Also, propagation can be detected by measuring specific adenoviral DNA replication, which are also standard assays.

The invention also provides methods of modifying the genotype of a target cell, comprising contacting the target cell with an adenovirus vector described herein, wherein the adenoviral vector enters the cell.

The invention further provides methods of suppressing tumor cell growth, comprising contacting a tumor cell with an adenoviral vector of the invention such that the adenoviral vector enters the tumor cell and exhibits selective cytotoxicity for the tumor cell. As used herein, "tumor cells" and "tumor" refer to cells which exhibit relatively autonomous growth, so that they exhibit an aberrant growth phenotype characterized by a significant loss of control of cell proliferation. Tumor cell growth can be assessed by any means known in the art, including, but not limited to, measuring tumor size, determining whether tumor cells are proliferating using a $^3$H-thymidine incorporation assay, or counting tumor cells. "Suppressing" tumor cell growth means any or all of the following states: slowing, delaying, and stopping tumor growth, as well as tumor shrinkage. "Suppressing" tumor growth indicates a growth state that is curtailed when compared to growth without contact with, i.e., transfection by, an adenoviral vector described herein. See Example 4, FIG. 6.

The invention also provides methods of lowering the levels of a tumor cell marker in an individual, comprising administering to the individual an adenoviral vector of the present invention, wherein the adenoviral vector is selectively cytotoxic toward cells producing the tumor cell marker. Tumor cell markers include, but are not limited to, PSA, carcinoembryonic antigen and hK2. Methods of measuring the levels of a tumor cell marker are known to those of ordinary skill in the art and include, but are not limited to, immunological assays, such as enzyme-linked immunosorbent assay (ELISA), using antibodies specific for the tumor cell marker. In general, a biological sample is obtained from the individual to be tested, and a suitable assay, such as an ELISA, is performed on the biological sample. See Example 4, FIG. 7.

The invention also provides methods of treatment, in which an effective amount of an adenoviral vector(s) described herein is administered to an individual. For example, treatment using an adenoviral vector(s) in which at least one heterologous TRE is specific for prostate cells (e.g., PSE-TRE, PB-TRE, and/or hKLK2-TRE) is indicated in individuals with prostate-associated diseases as described above, such as hyperplasia and cancer. In this example, also indicated are individuals who are considered to be at risk for developing prostate-associated diseases, such as those who have had disease which has been resected and those who have had a family history of prostate-associated diseases. Determination of suitability of administering adenoviral vector(s) of the invention will depend, inter alia, on assessable clinical parameters such as serological indications and histological examination of tissue biopsies. Generally, a pharmaceutical composition comprising an adenoviral vector(s) is administered. Pharmaceutical compositions are described above.

The amount of adenoviral vector(s) to be administered will depend on several factors, such as route of administration, the condition of the individual, the degree of aggressiveness of the disease, the particular heterologous TREs employed, and the particular vector construct (i.e., which adenovirus genes are under heterologous TRE control).

If administered as a packaged adenovirus, from about 1 to about $10^{14}$, preferably from about $10^4$ to about $10^{12}$, more preferably from about $10^4$ to about $10^{10}$. If administered as a polynucleotide construct (i.e., not packaged as a virus), about 0.01 μg to about 100 μg can be administered, preferably 0.1 μg to about 500 μg, more preferably about 0.5 μg to about 200 μg. More than one adenoviral vector can be administered, either simultaneously or sequentially. Administrations are typically given periodically, while monitoring any response. Administration can be given, for example, intratumorally, intravenously or intraperitoneally.

The adenoviral vectors of the invention can be used alone or in conjunction with other active agents, such as chemotherapeutics, that promote the desired objective.

The following examples are provided to illustrate but not limit the invention.

EXAMPLES

Example 1

Generation of Adenovirus Vector Constructs in which a First Adenovirus Gene is Under Transcriptional Control of an hKLK2-TRE and a Second Adenovirus Gene is Under Transcriptional Control of a PSE-TRE 1.1 Construction of Adenovirus Constructs in which Expression of One Adenovirus Gene is Controlled by an hKLK2-TRE To generate hKLK2-TRE adenovirus constructs, four hKLK2-TRE fragments which contain at least the hKLK2 minimal promoter were amplified using the DNA sequence from approximately 12,000 bp lying upstream of the first exon in hKLK2 (SEQ ID NO:3) and synthetic oligonucleotides as described below. The four constructs were generated by ligating these fragments into pGEM-T vector.

CN294 is a pGEM-T vector derivative containing an hKLK2 full promoter. The fragment was amplified by PCR with oligonucleotide 42.100.1: 5'-GAT C ACCGG TGT CCA CGG CCA GGT GGT GC-3' (SEQ ID NO:11) (PinAI site underlined), which is complementary to the 5'-untranslated region (UTR) of the first exon in hKLK2, in combination with 42.100.2 (5'-GAT CAC CGGTGC TCA CGC CTG TAA TCT CAT CAC- 3'; SEQ ID NO:12; PinAI site underlined). 42.100.2 corresponds to the upstream region of the hKLK2 promoter.

CN296 is a pGEM-T vector derivative containing an hKLK2 fragment from nt −2247 to nt +33, which was amplified by PCR with oligonucleotides 42.100.1 and 42.100.3 (5'-GAT CAC CGG TGG TTT GGG ATG GCA TOG CTT TGG-3'; SEQ ID NO:13, PinAI site underlined). 42.100.3 corresponds to a region approximately 2300 bp upstream of hKLK2.

CN317 is a pGEM-T derivative containing the hKLK2 minimal promoter. A PCR fragment corresponding to the hKLK2 5'-UTR from nt −323 to nt +33 was amplified with two synthetic oligonucleotides; 42.100.1 and 43.121.1 (5'-GAT CAC CGG TAA AGA ATC AGT GAT CAT CCC AAC-3'; SEQ ID NO:14, PinAI site underlined).

CN310 is a pGEM-T vector derivative containing an hKLK2 full promoter and is identical to CN294 except EagI sites flank the insert. The fragment was amplified by PCR with oligonucleotide 42.174.1 (5'-GAT C CG GCC GTG GTG CTC ACG CCT GTA ATC-3'; SEQ ID NO:15, EagI site underlined) in combination with 42.174.2 (5'-GAT CCG GCC GTG TCC ACG GCC AGG TGG TGC AG-3'; SEQ ID NO:16; EagI site underlined).

hKLK2 Promoter-driven E1A Ad5 Plasmid CN303

CN303 was produced by inserting the hKLK2 promoter just upstream of the E1A coding segment in a derivative of pXC-1, a plasmid containing the left hand end of the Ad5 genome, as follows.

CN124 is a derivative of construct pXC-1 which contains the wild-type left hand end of Ad5, including both E1A and E1B (McKinnon (1982) *Gene* 19:33–42). CN124 also has, among other alterations, an artificial PinAI site at Ad5 nt 547 (just upstream of the E1A transcriptional start at nt 560 and the E1A coding segment beginning with ATG at 610). CN124 was linearized with PinAI and dephosphorylated with calf intestinal alkaline phosphatase (New England Biolabs).

CN294 was digested with PinAI to free the hKLK2 promoter. The hKLK2 promoter was then ligated into the PinAI linearized CN124, producing CN303. CN304 is similar to CN303 except for the hKLK2 promoter fragment is in the reverse orientation.

Thus, construct CN303 contains the hKLK2 promoter inserted upstream of and operably linked to the E1A coding segment in the Adenovirus 5 genome.

hKLK2 Promoter-driven E1B Ad5 Plasmid CN316

CN316 was produced by inserting the hKLK2-promoter just upstream of the E1B coding segment in a derivative of pXC-1, a plasmid containing the left hand end of the Ad5 genome, as follows.

CN124, described above, also contains an artificial EagI site at Ad5 nt 1682, just upstream of the E1B coding segment. The hKLK2 promoter was excised from CN310 with EagI and inserted into CN124 digested with EagI to produce CN316. CN316 contains the hKLK2 promoter immediately upstream of and operably linked to the E1B coding segment.

1.2 Construction of Adenovirus Constructs in which Expression of One Adenovirus Replication Gene is Controlled by an hKLK2-TRE and Expression of Another Adenovirus Replication Gene is Controlled by a PSE-TRE Ad5 Construct Comprising an hKLK2-TRE Driven E1A and a PSE-TRE Driven E1B (CN301)

CN301 was generated from CN125 by inserting an hKLK2 promoter upstream of the E1A gene as follows.

CN125 is a pXC-1 derivative in which expression of the E1B gene is driven by PSE. A PinAI site lies upstream of the E1A gene, whose expression is driven by its wild-type promoter. CN125 was created by inserting PSE as an EagI fragment from construct CN105 into the EagI site immediately upstream of the E1B gene in CN124. CN105 contains the PSE region from −5322 to −3875 relative to the PSA transcription start site.

The hKLK2-TRE fragment was freed from CN294 by PinAI digestion and ligated into PinAI digested CN125 to create CN301.

The CN301 construct contains the hKLK2 promoter immediately upstream of and operably-linked to the E1A gene and the PSE-TRE immediately upstream of and operably-linked to the E1B gene.

Ad5 Constructs Comprising PSE-TRE Driven E1A Gene and hKLK2 Promoter Driven E1B Gene (CN323)

CN323 was constructed as follows so that the expression of E1A is mediated by PSE-TRE, and expression of E1B is mediated by an hKLK2 promoter.

CN314 is a plasmid containing a PSE-TRE fragment in pGEM-T vector. This PSE fragment was amplified from CN706, an adenoviral construct in which a PSE-TRE (SEQ ID NO:2) drives expression of the E1A transcription unit in Ad5, with two synthetic oligonucleotides:

51.10.1 (5'-CTC ATT TTC AGT CAC CGG TAA GCT TGG-3'; SEQ ID NO:17) and 51.10.2 (5'-GAG CCG CTC CGA CAC CGG TAC CTC-3'; SEQ ID NO:18).

The PSE-TRE fragment was isolated by digesting CN314 with PinAI and ligated into PinAI digested CN316 (described above).

The CN323 construct is a plasmid containing PSE-TRE immediately upstream of and operably-linked to the E1A gene and the hKLK2 promoter immediately upstream of and operably-linked to the E1B gene.

1.3 Construction of Additional Adenoviral Constructs Comprising a First Adenoviral Gene Under Transcriptional Control of an hKLK2-TRE and a Second Adenoviral Gene Under Transcriptional Control of a PSE-TREs CN306 was derived from CN124 by removing the endogenous 64-nucleotide E1A promoter.

CN421 was constructed by inserting an hKLK2-TRE (comprising an hKLK2 enhancer from nucleotides −5155 to −3387 relative to the hKLK2 gene transcription start site (nucleotides 6859 to 8627 of SEQ ID NO:3) and an hKLK2 minimal promoter as in CN379 into CN306. The hKLK2-TRE fragment was amplified by PCR from CN379, digested with PinAI and ligated into similarly cut CN306, to produce CN421.

CN438 was constructed by inserting an hKLK2-TRE (comprising an hKLK2 enhancer from nucleotides −4814 to −3643 relative to the hKLK2 gene transcription start site (nucleotides 7200 to 8371 of SEQ ID NO:3) and a minimal hKLK2 promoter as in CN390 into CN306. The enhancer fragment was amplified by PCR from CN390, digested with PinAI and ligated into similarly cut CN306, to produce CN438.

CN321 was created from CN306 by inserting a large PSE-TRE amplified from CN96 (see U.S. Pat. No. 5,698,443; Rodriguez et al. (1997)).

CN416 was constructed by inserting an hKLK2-TRE (comprising an hKLK2 enhancer from nucleotides −5155 to −3387 relative to the hKLK2 gene transcription start site (nucleotides 6859 to 8627 of SEQ ID NO:3) and an hKLK2 minimal promoter as in CN379 into CN321. The enhancer fragment was amplified by PCR from CN379, digested with EagI and ligated into similarly cut CN321, to generate CN416.

CN422 was constructed by inserting an hKLK2-TRE (comprising an hKLK2 enhancer from nucleotides −5155 to −3387 relative to the hKLK2 gene transcription start site (nucleotides 6859 to 8627 of SEQ ID NO:3) and an hKLK2 minimal promoter as in CN379 into CN369. CN369 is a derivative of CN306 in which the endogenous E1B promoter was removed. The hKLK2-TRE was amplified from CN379, digested with EagI, and ligated into similarly cut CN369 to produce CN422.

CN444 was constructed by replacing the hKLK2-TRE of CN442 with an hKLK2-TRE comprising an hKLK2 enhancer from nucleotides −4814 to −3643 relative to the hKLK2 transcription start site (nucleotides 7200 to 8371 of SEQ ID NO:3) and a minimal hKLK2 promoter, as in CN390. The hKLK2-TRE was amplified from CN390, digested with EagI, and ligated into similarly cut CN369, to produce CN444.

CN446 is similar to CN444, except that the endogenous E1B promoter was not removed. The hKLK2-TRE was amplified from CN390, digested with EagI, and ligated into similarly cut CN321, to produce CN446.

CN459 and CN460 are similar to CN444, except that each contains an hKLK2-TRE comprising an hKLK2 enhancer from nucleotides −3993 to −3643 relative to the hKLK2 transcription start site and a hKLK2 minimal promoter, as in CN396.

CN463 was constructed by inserting an hKLK2-TRE (comprising an hKLK2 enhancer from nucleotides −4814 to −3643 relative to the hKLK2 transcription start site and a minimal hKLK2 promoter, as in CN390, into CN251. The hKLK2-TRE was excised from CN446 with EagI, and ligated into similarly cut CN251, to produce CN463.

1.4 Generation of Recombinant Adenoviruses

Adenovirus containing hKLK2-TRE were generated by homologous recombination in 293 cells. Briefly, CN301 was co-transfected with BHG10 (which contains right hand end of the adenovirus genome), into 293 cells. The cells were overlaid with media, and infectious virus generated by in vivo recombination was detected by cytopathic effect and isolated. Plaque-purified stocks of an adenovirus vector, designated CN747, were established. The structure of the recombinant virus was characterized by PCR, restriction endonuclease digestion and Southern blot. CN747 is a full-length Ad5 with the hKLK2 promoter driving the expression of E1A and a PSE-TRE driving expression of E1B.

Virus CN754 were generated with the same approach except that the CN301 plasmid was replaced with CN323. CN754 is a virus whose E1A and E1B are under the control of the PSE-TRE and the hKLK2-TRE, respectively.

Viruses CN753, CN755, CN759, CN761, CN763, CN764, CN765, CN767, CN768, CN769, CN770, CN772 and CN773 were generated using the method as described above, from the parent plasmids CN326, CN328, CN398, CN316, CN421, CN416, CN422, CN436, CN438, CN444, CN446, CN459, CN460, and CN463, respectively. These viral constructs are shown schematically in FIGS. 2A, 2B and 2B.

Example 2

Construction of Adenovirus Vectors in Which Expression of One Viral Replication Gene is Controlled by a PSE-TRE and Expression of Another is Controlled by a PB-TRE 2.1 Generation of Adenovirus Constructs in which Expression of one Adenovirus Gene is Controlled by a PB-TRE The 454 nucleotide fragment (nt about −426 to about +28) of the rat PB-TRE, which contains two androgen response elements (ARE sites) and a promoter element (SEQ ID NO:4), was amplified by PCR using rat genomic DNA as template and the following oligonucleotides primers:

5'-GATC ACCGGTAAGCTTCCACAAGTGCATTTAGCC-3', 42.2.1 (PinAI site underlined) (SEQ ID NO:19) and
5'-GATC ACCGGTCTGTAGGTATCTGGACCTCACTG-3', 42.2.2 (SEQ ID NO:20) or primers:
5'-GATC CGGCCGAAGCTTCCACAAGTGCATTTAGCC-3', 42.2.3 (EagI site underlined) (SEQ ID NO:21) and
5'-GATC CGGCCGCTGTAGGTATCTGGACCTCACTG-3'. 42.2.4 (SEQ ID NO:22)

The oligonucleotides created a unique PinAI (AgeI) site (A/CCGGT) or EagI site (C/GGCCG) at both ends of the PCR fragments. The PCR fragments were ligated into the pGEM-T vector (Promega) to generate plasmids CN249 and CN250. Similarly, CN256 was created using the same strategy but the PB-TRE fragment was ligated into the pCRT vector (Invitrogen); CN271 is identical to CN250 but with a HindIII site at the 5'-end. These plasmids provide the PB-TRE DNA fragments for the constructs reported below. In some of the adenovirus vectors described below, the endogenous (adenoviral) TREs were not deleted; rather, in each construct, the PB-TRE was inserted between the endogenous TRE (e.g., the E1A TRE) and its respective coding segment (e.g., the E1A coding segment). In other vectors, the endogenous (Ad5) promoter-enhancer has been deleted, and the prostate-specific promoter-enhancer placed immediately upstream of an early gene.

PB-TRE-driven E1A Ad5 Plasmid (CN251)

An adenovirus vector in which expression of early gene E1A is under transcriptional control of PB-TRE was constructed as follows.

CN124 was linearized with PinAI and dephosphorylated with calf intestinal alkaline phosphatase (New England Biolabs). CN249 was digested with PinAI to free the PB-TRE fragment. The PB-TRE fragment was then ligated into the PinAI-linearized CN124, producing CN251. CN253 is similar to CN251 except for the PB-TRE is in the reverse orientation.

Thus, construct CN251 contains the PB-TRE inserted upstream of and operably linked to the E1A coding segment in the Adenovirus 5 genome. The vector CN253 is similar, but the PB-TRE is in the reverse orientation.

PB-TRE-driven E1B Ad5 Plasmid (CN254)

An adenovirus derivative in which the expression of early gene E1B is under transcriptional control of the PB-TRE was constructed as follows.

CN124, which carries the left-end of Ad5, as described above, also contains an artificial EagI site at Ad5 nt 1682, or just upstream of the E1B coding segment. The PB-TRE fragment was excised from CN250 with EagI and inserted into CN124 digested with EagI. This produced CN254, which contains the PB-TRE immediately upstream of and operably linked to the E1B coding segment.

CN255 is identical to CN254, but the orientation of the PB-TRE insert is reversed. CN275 is the same as CN254, but with a HindIII site at the 5'-end.

2.2 Generation of Adenovirus Constructs in Which Expression of One Adenovirus Replication Gene is Controlled by a PB-TRE and Expression of Another Adenovirus Gene is Controlled by a PSE-TRE Adenovirus Vector Comprising a PB-TRE Driven E1A and a PSE-TRE Driven E1B (CN257)

An adenovirus vector in which expression of the E1A gene is under control of the PB-TRE and expression of the E1B gene is under control of the prostate specific antigen transcriptional regulatory element (PSE-TRE) was constructed as follows. The PSE-TRE region has been described in detail in, inter alia, U.S. Pat. Nos. 5,648,478 and 5,698,443; Lundwall (1989) *Biochim. Biophys. Res. Commun.* 161:1151–1159; and Zhang et al. (1997) *Nucleic Acids Res.* 25:3143–50.

The PinAI PB-TRE fragment was inserted into CN125 digested with PinAI, which cleaves just upstream of E1A, to create construct CN257, which is a plasmid containing a PB-TRE operably linked to the E1A gene and a PSE-TRE operably linked to the E1B gene. CN258 is similar to CN257, but with the opposite orientation of the PB-TRE fragment.

Ad5 Plasmid Comprising PSE-TRE Driven E1A and PB-TRE Driven E1B (CN273)

An adenovirus vector was constructed in which expression of E1A is mediated by a PSE-TRE and expression of E1B is mediated by a PB-TRE.

CN143 is a pBluescript (Stratagene, La Jolla, Calif.) derivative containing the PSE-TRE fragment. This fragment was excised with PinAI and ligated into PinAI-digested CN254. The final construct is a plasmid containing a PSE-TRE operably linked to the E1A gene and a PB-TRE operably linked to the E1B gene. CN274 is similar to CN273 except for the opposite orientation of PB-TRE.

CN306 was derived from CN124 by removing E1A endogenous promoter of 64 nts. CN321 was created from CN306 with a inserting of large PSE fragment amplified from CN96.

CN326 was derived from CN321 by inserting PB-TRE into EagI site. CN321 is a plasmid containing PSE (from CN96) at the PinAI site of CN306.

2.3 Construction of Adenovirus Constructs in Which Expression of One Adenovirus Replication Gene is Controlled by hKLK2-TRE and Expression of Another Adenovirus Replication Gene is Controlled by PB-TRE CN463 was generated from CN251 by inserting an hKLK2-TRE into the EagI site. The hKLK2-TRE was excited from plasmid CN446 with EagI, ligated into a similarly cut CN251, to produce CN463. The CN463 construct is a plasmid containing a PB-TRE immediately upstream and operably linked to the E1A gene and an hKLK2-TRE (comprising an hKLK2 enhancer from nucleotides −4814 to −3643 relative to the hKLK2 transcription start site and minimal hKLK2 promoter) immediately upstream and operably linked to the E1B gene.

2.4 Generation of Adenoviruses that Contain Two Heterologous TREs

Adenoviruses that contain two heterologous TREs were generated by homologous recombination in 293 cells. Briefly, 5 μg of CN257 and 5 μg of BHG10, which contains the right hand end of Ad5, was co-transfected into 293 cells. The cells were overlaid with medium, and infectious virus, generated by in vivo recombination, was detected by cytopathic effect and isolated. Plaque-purified stocks of an adenovirus vector, designated CN739, were established. The structure of the recombinant virus was characterized by PCR, restriction endonuclease digestion and Southern blot. The viral genome of CN739 has the E1A transcription unit of Ad5 under the control of PB-TRE while E1B is under the control of PSE-TRE.

As shown in FIG. 2, adenoviruses CN750, CN753, CN764, CN767, CN770, CN772, CN774, were generated with the same approach except that CN257 was replaced with CN273, CN326, CN416, CN436, CN446, CN459, CN463, respectively.

Example 3

In vitro Characterization of Adenoviral Constructs Comprising an Adenoviral Gene Under Transcriptional Control of Prostate Cell Specific Heterologous TREs Plaque Assays To determine whether the adenoviral constructs described in Examples 1 and 2 replicate preferentially in prostate cells, plaque assays were performed. A plaque assay is an infectious quantitative assay that quantifies how efficiently a particular virus produces an infection in a cell. Plaquing efficiency was evaluated in the following cell types: prostate tumor cell lines (LNCaP, PC-3), breast normal cell line (HBL-100), breast carcinoma cell line (MCF-7), ovarian tumor cell lines (OVCAR-3, SK-OV-3), hepatocarcinoma cell lines (HepG2, SK-Hep-1), and human embryonic kidney cells (293). LNCaP cells express both androgen receptor and PSA, while the other cell lines tested do not. 293 cells serve as a positive control for plaquing efficiency, since this cell line expresses Ad5 E1A and E1B proteins. The plaque assay was performed as follows. Confluent cell monolayers were seeded in 6-well dishes eighteen hours before infection. The monolayers were infected with 10-fold serial dilutions of each virus. After infecting monolayers for four hours in serum-free media (MEM), the media was removed and replaced with a solution of 0.75% low melting point agarose and tissue culture media. Plaques were scored two weeks after infection. CN702 has no modifications in its E1 region and is used as a wild type control.

TABLE 1

Adenovirus with heterolgous TREs plaque assay data (Percent of wild-type adenovirus (PFU/ml))

| Viruses | 293 | LNCaP | HBL-100 | OVCAR-3 | SK-OV-3 |
|---|---|---|---|---|---|
| CN702 | 100 | 100 | 100 | 100 | 100 |
| CN706 | 100 | 23 | 4.2 | 5.5 | 8.9 |
| CN764 | 100 | 31 | 0.25 | 0.032 | 0.003 |
| CN769 | 100 | 11 | 0.14 | 0.015 | 0.0008 |
| CN770 | 100 | 24 | 0.27 | 0.036 | 0.084 |
| CN772 | 100 | 29 | 0.27 | 0.096 | 0.21 |

TABLE 2

Adenovirus with heterologous TREs plaque assay data (Percent of wild-type adenovirus (PFU/ml))

| Viruses | 293 | LNCaP | HBL-100 | OVCAR-3 |
|---|---|---|---|---|
| CN702 | 100 | 100 | 100 | 100 |
| CN706 | 100 | 25 | 2.7 | 7.7 |
| CN753 | 100 | 33 | 0.067 | 0.52 |
| CN755 | 100 | 29 | 0.52 | 0.6 |

TABLE 3

Adenovirus with heterologous TREs plaque assay data
(Percent of wild-type adenovirus (PFU/ml))

| Viruses | 293 | LNCaP | HBL-100 | OVCAR-3 |
|---|---|---|---|---|
| CN702 | 100 | 100 | 100 | 100 |
| CN706 | 100 | 33 | 2.5 | 3.4 |
| CN739 | 100 | 35 | 0.12 | 0.0023 |
| CN753 | 100 | 41 | 0.23 | 0.11 |

TABLE 4

Adenovirus with heterologous TREs plaque assay data
(Percent of wild-type adenovirus (PFU/ml))

| Viruses | 293 | LNCaP | HBL-100 | OVCAR-3 |
|---|---|---|---|---|
| CN702 | 100 | 100 | 100 | 100 |
| CN753 | 100 | 37 | 0.15 | 0.086 |
| CN765 | 100 | 20 | 0.22 | 0.012 |
| CN772 | 100 | 29 | 0.27 | 0.096 |

TABLE 5

Adenovirus with heterologous TREs plaque assay data
(Percent of wild-type adenovirus (PFU/ml))

| Viruses | 293 | LNCaP | HBL-100 | OVCAR-3 | SK-OV-3 |
|---|---|---|---|---|---|
| CN702 | 100 | 100 | 100 | 100 | 100 |
| CN706 | 100 | 23 | 4.2 | 6.1 | 8.9 |
| CN764 | 100 | 31 | 0.25 | 0.032 | 0.003 |
| CN769 | 100 | 11 | 0.14 | 0.015 | 0.0008 |
| CN770 | 100 | 24 | 0.27 | 0.036 | 0.084 |

TABLE 6

Adenovirus with heterologous TREs plaque assay data
(Percent of wild-type adenovirus (PFU/ml))

| Viruses | 293 | LNCaP | PC-3 | HBL-100 | OVCAR-3 | HepG2 | SK-Hep 1 |
|---|---|---|---|---|---|---|---|
| CN702 | 100 | 100 | 100 | 100 | 100 | 100 | 100 |
| CN706 | 100 | 33 | 74 | 2.4 | 1.8 | 12 | 1.8 |
| CN739 | 100 | 35 | 46 | 0.058 | 0.0057 | 0.068 | 0.00 |

TABLE 7

Adenovirus with heterologous TREs plaque assay data
(Percent of wild-type adenovirus (PFU/ml))

| Viruses | 293 | LNCaP | MCF-7 |
|---|---|---|---|
| CN702 | 100 | 100 | 100 |
| CN706 | 100 | 25 | 1.5 |
| CN737 | 100 | 26 | 0.11 |

Tables 1–7 show the results of plaque assays performed with the adenoviral vectors described in Examples 1 and 2. The results are expressed as percent of wild-type adenovirus plaque-forming units (PFU) per ml. The tables show the average titer of duplicate samples for the viruses tested. The titer for a particular virus in all cell lines was normalized to its titer on 293 cells. Once the titers on a cell type were normalized to 293 cells, the normalized numbers of the recombinant viruses were compared to CN702. A ratio of less than 100 suggests that the virus tested plaques less efficiently than CN702. Conversely, a ratio greater than 100 suggests that the virus plaques more efficiently than CN702.

The following observations were made. First, hKLK2-TRE, PSE-TRE and PB-TRE engineered adenoviruses demonstrate preferential replication in prostate tumor cells. Since this carcinoma expresses androgen receptors, the PSE, hKLK2 and PB TREs contained in the adenoviral vectors should be active in promoting the transcription of the adenovirus early genes. The data presented in Tables 1–7 suggest that the heterologous TRE containing adenoviral vectors induce cytopathic effects with a slightly lower efficiency than wild type adenovirus in prostate tumor cells. Second, hKLK2-TRE, PSE-TRE and PB-TRE containing adenoviruses show a dramatically lower plaquing efficiency in non-prostate tumor cells when compared to wild type. For example, in the ovarian carcinoma cell line OVCAR-3, CN764 and CN739 produced 3,000- and 10,000-fold less plaques than wild type Ad5, respectively. The results are similar for these two viruses in HBL-100 cells, where virus replication is also severely compromised. Third, adenoviral vectors containing two prostate cell specific heterologous TREs give 10 to 100-fold (or more) less plaques in non-prostate cells that an adenoviral vector containing a single heterologous prostate cell specific TRE despite the titers of the two types of adenovirus vectors being similar in LNCaP cells. For example, PSE-TRE and hKLK2-TRE (CN764) or PSE-TRE and PB-TRE (CN739) adenovirus vectors give 10- to 100-fold less plaques in HBL-100 and OVCAR-3 cells than CN706, although their titers were similar to CN706 in LNCaP cells. Thus, adenoviruses engineered with two different prostate cell specific TREs were significantly attenuated relative to wild-type adenovirus and CN706 in non-prostate cells, but they showed similar activity to CN706 in LNCaPs.

As indicated above, adenoviruses containing two heterologous TREs demonstrated an unexpectedly high preferential replication in prostate tumor cells as compared to wild type adenovirus and to CN706, in which a PSE-TRE controls E1A. This increase in specificity is more than an additive effect of inserting a second prostate-specific TRE.

Since CN739 and CN764 appeared to be the most specific viruses, they were further characterized in the following experiments.

Cytopathic Effects

Figure 3:
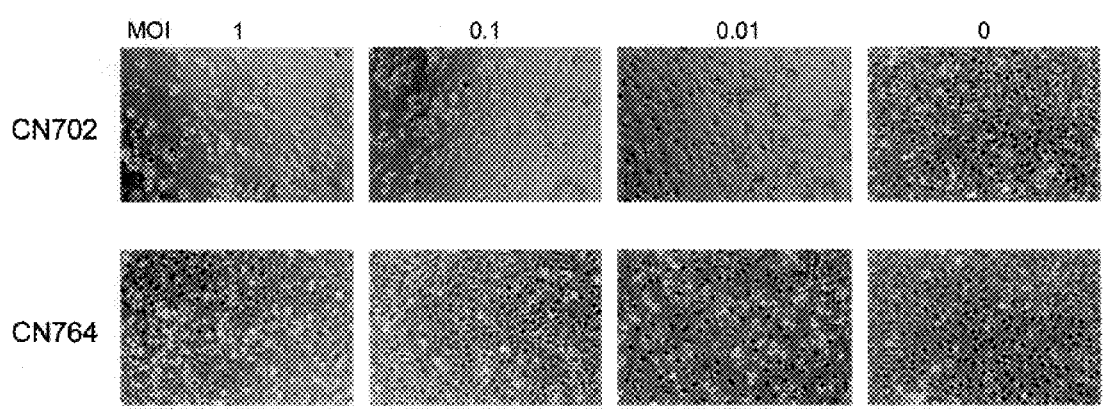
FIG. 3 shows the cytopathic effects of CN702 and CN764 at various multiplicities of infection on human microvascular endothelial cells.

To characterize the differential viral replication and cytopathic effects (CPE), CPE assays were performed as follows. Cells were infected with virus at increasing multiplicities of infection (MOI) and monitored for cytopathic effect. Assays were terminated when complete cytolysis of the monolayers was observed at an MOI of 0.01 with wild-type adenovirus. One primary, non-immortalized human microvascular endothelial cell line (hMVEC) was chosen to test its sensitivity to CN764 and wild-type adenovirus (CN702) infection, in vitro. As shown in FIG. 3, CN702 caused complete monolayer cytolysis of hMVECs at MOIs as low as 0.01 within 10 days. In contrast, CN764 infected hMVEC monolayers did not show significant cytopathic effects at the same time points with MOIs of 10, 1.0, 0.1 and 0.01. Cytolysis of hMVECs equivalent to that seen with wild-type adenovirus was only evident at MOIs between 100 and 1000 times as high (MOI>10).

When the CPE assay was performed with CN739, the results were similar to that of CN764 as CN739-infected hMVEC monolayers did not show significant cytopathic effects at the same time points with MOIs of 10, 1.0, 0.1 and 0.01.

Thus, CN764 and CN739-mediated cytolysis is significantly attenuated relative to wild-type adenovirus in primary normal human cells.

Differential Viral Replication

Figure 4:
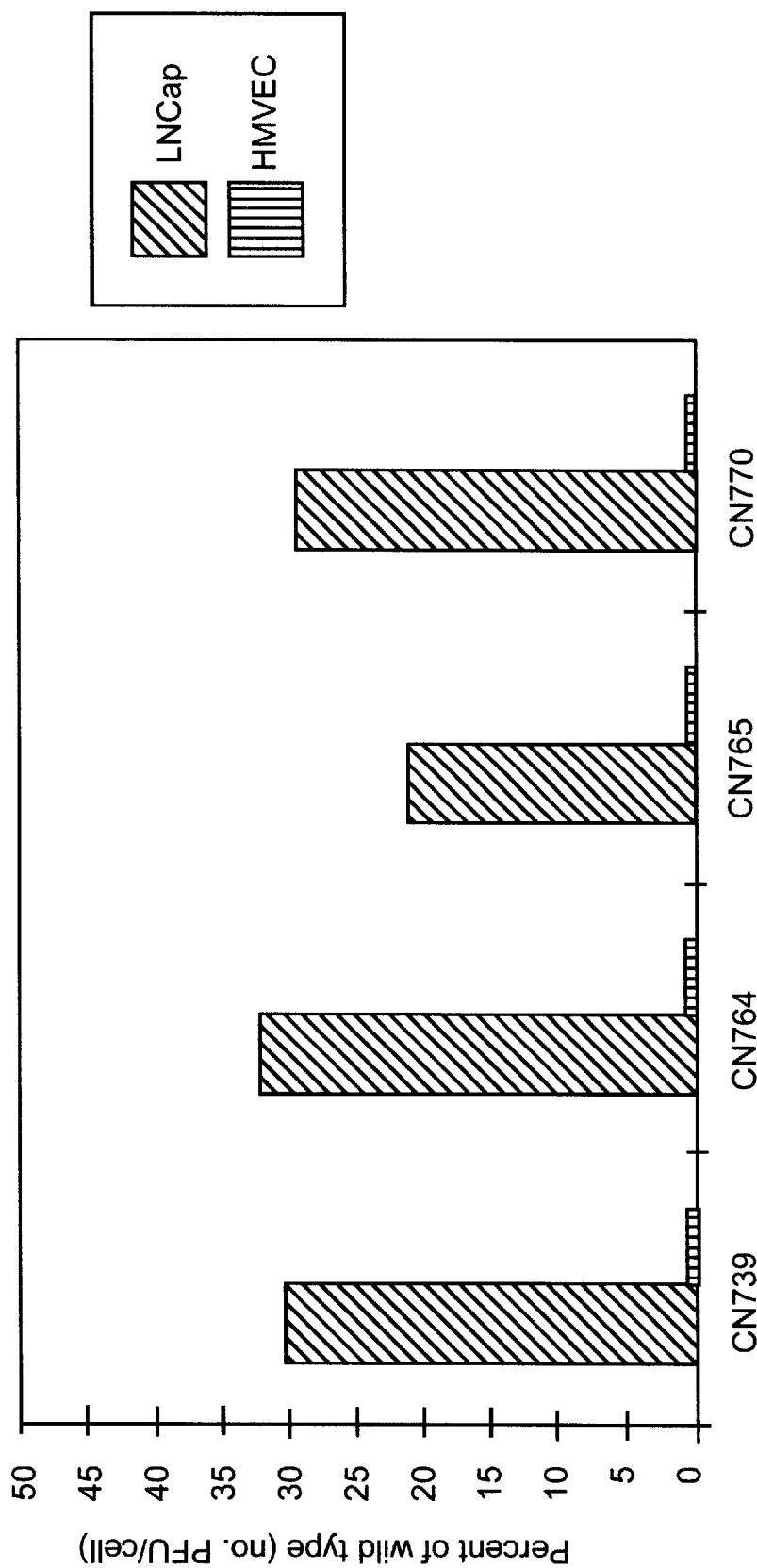
FIG. 4 is a bar graph showing the number of plaque-forming units, expressed as percentage of plaques obtained with wild-type adenovirus, obtained when either LNCaP cells (hatched bars) or HMVEC cells (bars with square pattern) were infected with adenoviral vectors CN739, CN764, CN765 or CN770.

To determine if levels of virus replication correlate with the cytopathic effects of CN739 in prostate tumor cells or human normal cells, virus replication titration was carried out on PSA producing prostate tumor cells (LNCaP) and primary human microvascular endothelial cells (hMVECs). Cells were grown to 70–90% confluence and infected with either wild-type adenovirus (CN702) or CN739, CN764, CN765, CN770 for 90 min at a MOI of 10. Fifty-five hours after infection, the virus was released from the cells by three freeze/thaw cycles, and the resulting supernatant was titered on 293 cells. The amount of CN739 produced 56 hours after infection was normalized against the amount of wild-type virus produced in the same cell line during the same time period. The data, shown in FIG. 4, indicate that the titers of adenovirus vectors containing two different prostate cell specific TREs were 30% of CN702 titers in LNCaPs, but were reduced to less than 1/100 those of the wild-type viruses in normal cells. These data suggest that CN764-like viruses replicate poorly in primary normal human cells, and are somewhat attenuated in prostate cancer cells.

One-step Growth Curve

Figure 5A:
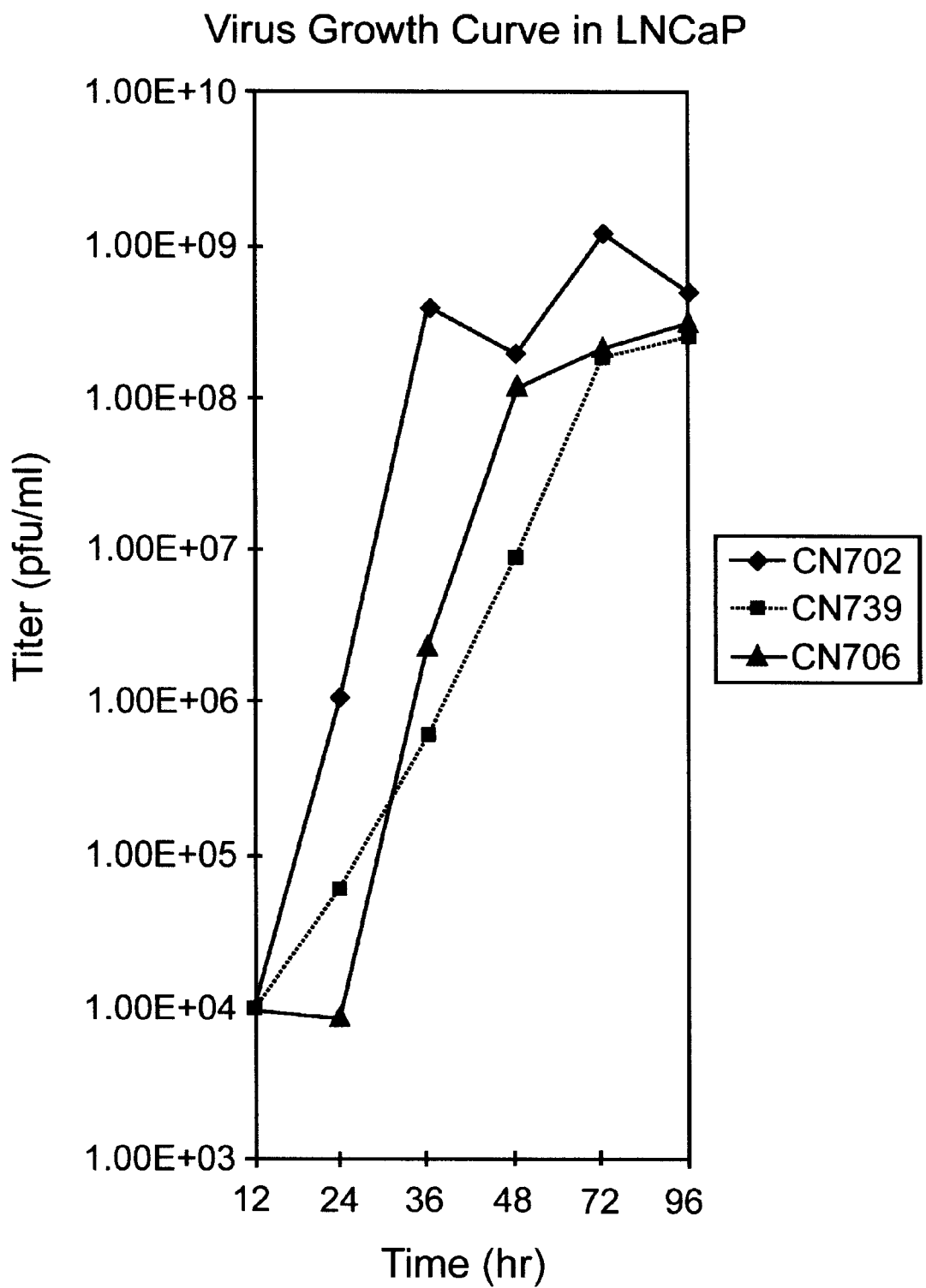
FIGS. 5A and 5B are line graphs illustrating the one-step growth curve of an adenovirus, CN739, in which multiple adenoviral early genes are placed under the control of prostate cell specific heterologous TREs, in prostate (LNCaP) and non-prostate cells (HMVEC).
Figure 5B:
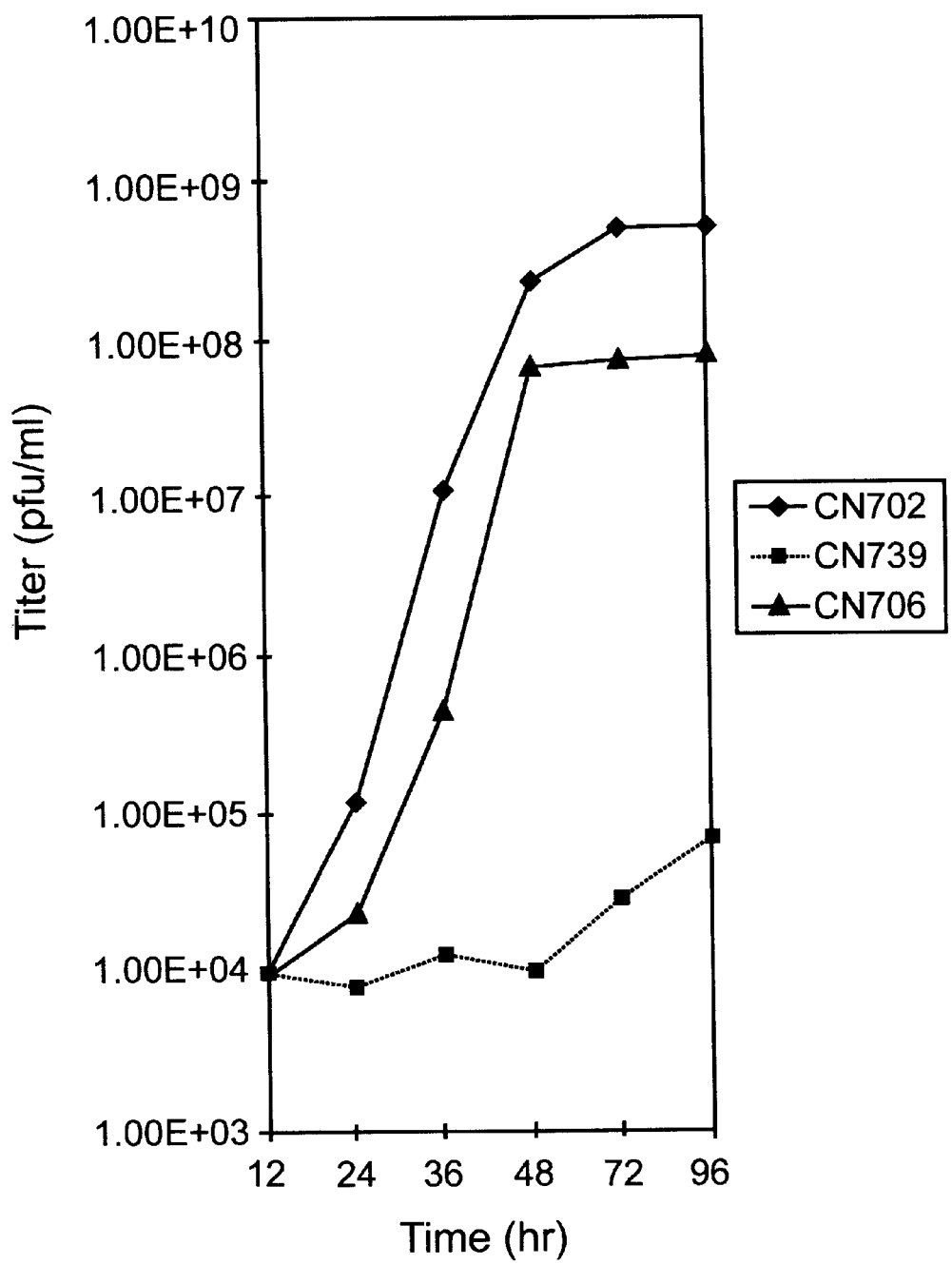

The efficiency and kinetics of replication of CN739, CN706 and CN702 were measured using a one-step growth curve assay in LNCaPs and hMVECs. Replicate monolayers of LNCaPs and hMVECs were infected at a MOI of 10 to obtain a synchronous infection of all the cells. Duplicate cultures were harvested at various times post-infection. The number of infectious virus was determined by plaque assay on 293 cells (FIG. 5). CN739 and CN706 grew at a similar efficiency in LNCaPs.

However, under identical conditions, CN739 grew poorly in the hMVECs, producing about 10,000-fold and 80,000-fold less infectious virus than CN706 and wild-type adenovirus, respectively.

Thus, the one-step growth curve demonstrated that an adenovirus containing two different prostate cell specific TREs, each controlling a different adenoviral gene, grew well in prostate tumor cells but grew poorly in non-prostate endothelial cells, indicating significantly enhanced specificity for target cells.

Stability of the Adenoviruses Containing Two Different Heterologous TREs

The use of two different heterologous TREs in the adenovirus vectors appears to provide stability to the genome during adenoviral replication. CN739 and CN764 were plaque purified for three times and their DNA were examined by PCR, as well as, Southern blot analysis. By this analysis, the viral genomes do not appear to have undergone sequence rearrangement or loss since the fragments were of the expected sizes. The results indicate that the adenoviral genome of the adenovirus vectors containing two different heterologous TREs are stable.

Example 4

Testing Cytotoxic Ability of Adenovirus Vectors on Tumor Xenografts

An especially useful objective in the development of target cell specific adenoviral vectors is to treat patients with neoplasia comprising the target cells. For example, the prostate cell specific adenoviral vectors described above may be useful to treat patients with prostate carcinoma. An initial indicator of the feasibility is to test the vectors using a technique known in the art, such as testing the vectors for cytotoxicity against neoplastic cell, such as prostate carcinoma, xenografts grown subcutaneously in Balb/c nu/nu mice. To examine the therapeutic efficacy of CN739 in vivo, LNCaP tumor xenografts were grown in athymic mice. The tumor cells were injected subcutaneously into each flank of each mouse, and after establishment of palpable tumors (mean tumor volume 300 mm$^3$), the tumors were directly injected with CsCl purified CN739 at 2.5×10$^8$ particles per mm$^3$, or PBS containing 10% glycerol (vehicle) as a control. Tumor growth was then followed for 6 weeks, at which time the mean tumor volume in each group was determined and serum samples were collected for PSA analysis on day 0 and weekly thereafter.

Figure 6:
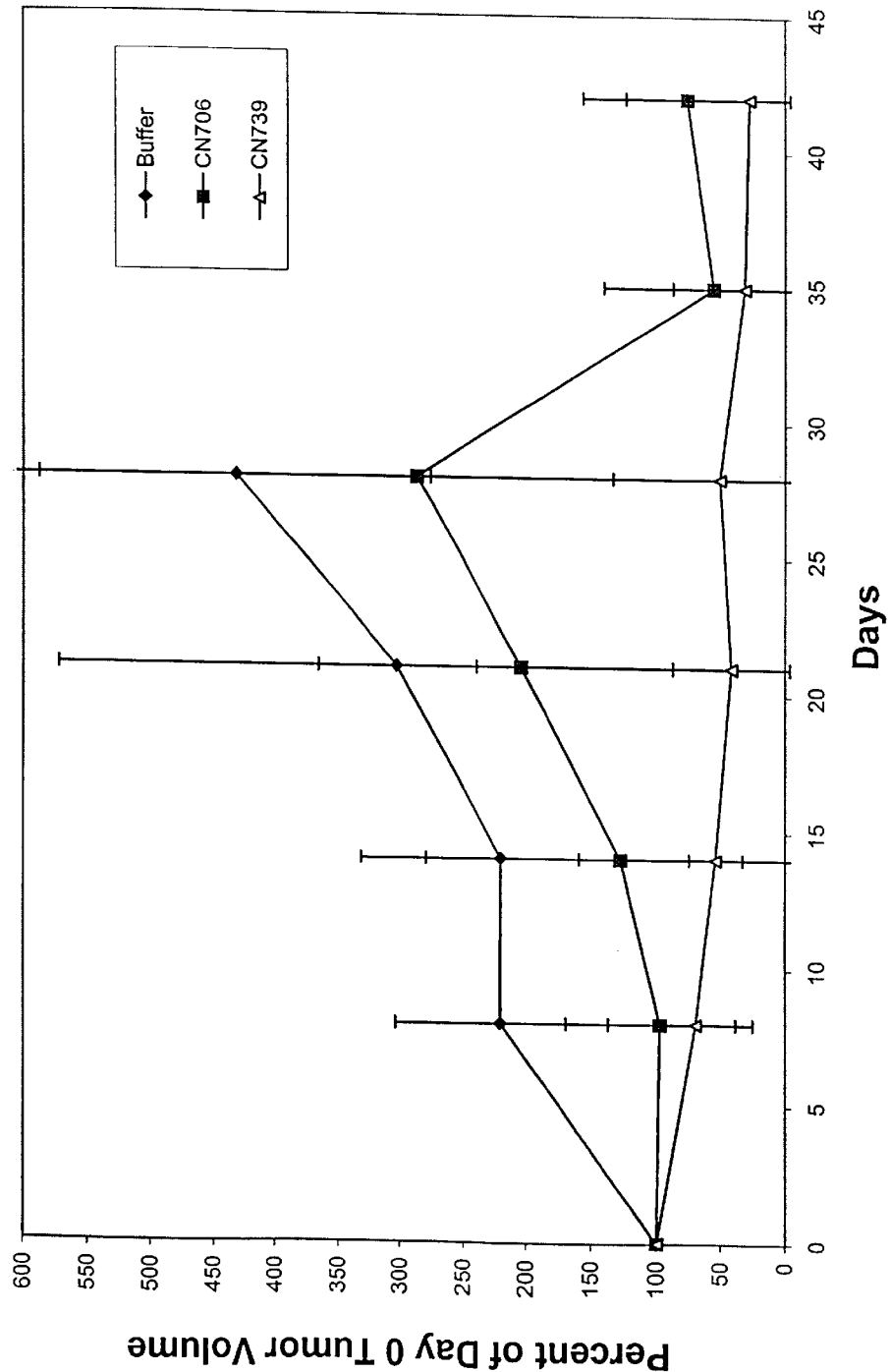
FIG. 6 is a line graph illustrating the efficacy in treating a prostate cancer tumor in mice of an adenovirus, CN739, in which multiple adenoviral early genes are placed under control of prostate cell specific heterologous TREs.

The data depicted in FIG. 6 show that treatment of LNCaP tumors with CN739 resulted in an 80% reduction in average tumor volume whereas the average tumor volume in vehicle-treated group I, at day 28, had increased to 400% of the initial volume. Four of seven (57%) animals in CN739-treated group II were free of palpable tumors at day 42. This study demonstrates that a fixed, single dose of an adenovirus containing two different prostate cell specific TREs, each operably linked to two different adenoviral genes, (CN739) per tumor is efficacious against LNCaP xenografts in vivo.

Effects on Serum PSA Levels

The serum PSA level is a widely used marker for the diagnosis and management of prostate carcinoma. LNCaP cells express and secrete high levels of PSA into the culture media and into circulation. An experiment was designed to examine the effects of treatment with CN739 on the serum PSA concentration in mice with LNCaP tumor xenografts.

Following treatment, the average serum PSA level in group I (vehicle only) increased to approximately 800% of the initial value by day 28, whereas the average PSA level in group II (CN706 treatment) and group III (CN739 treatment) remained essentially constant through day 21 and declined to 10% of the initial value by day 35 (FIG. 7). There was a statistically significant difference (p<0.001; T-test) between group I and group II on day 14 and thereafter.

These results demonstrate that CN739 treatment is efficacious in the LNCaP xenograft model when the outcome is measured either by reduction in tumor growth or serum PSA concentration. Taken together with the in vitro data, it appears that an adenovirus with two different prostate cell specific TREs (CN739) has a therapeutic efficacy in vivo similar to that of an adenovirus with a single prostate cell specific TRE (CN706) but in addition has a higher cell-specificity than CN706.

While it is likely that a therapeutic based on the viruses described here would be given intralesionally (i.e., direct injection), it would also be desirable to determine if intravenous (IV) administration of the virus can affect tumor growth. If so, then it is conceivable that the virus could be used to treat metastatic tumor deposits inaccessible to direct injection. For this experiment, groups of five mice bearing prostate cancer tumors are inoculated with 10$^8$ pfu of an adenoviral vector of the present invention by tail vein injection, or 10$^8$ pfu of a replication defective adenovirus (CMV-LacZ) to control for non-specific toxic effects of the virus, or with buffer used to carry the virus. The effect of IV injection of the adenoviral vector on tumor size is compared to the sham treatment.

Example 5

Figure 8A:
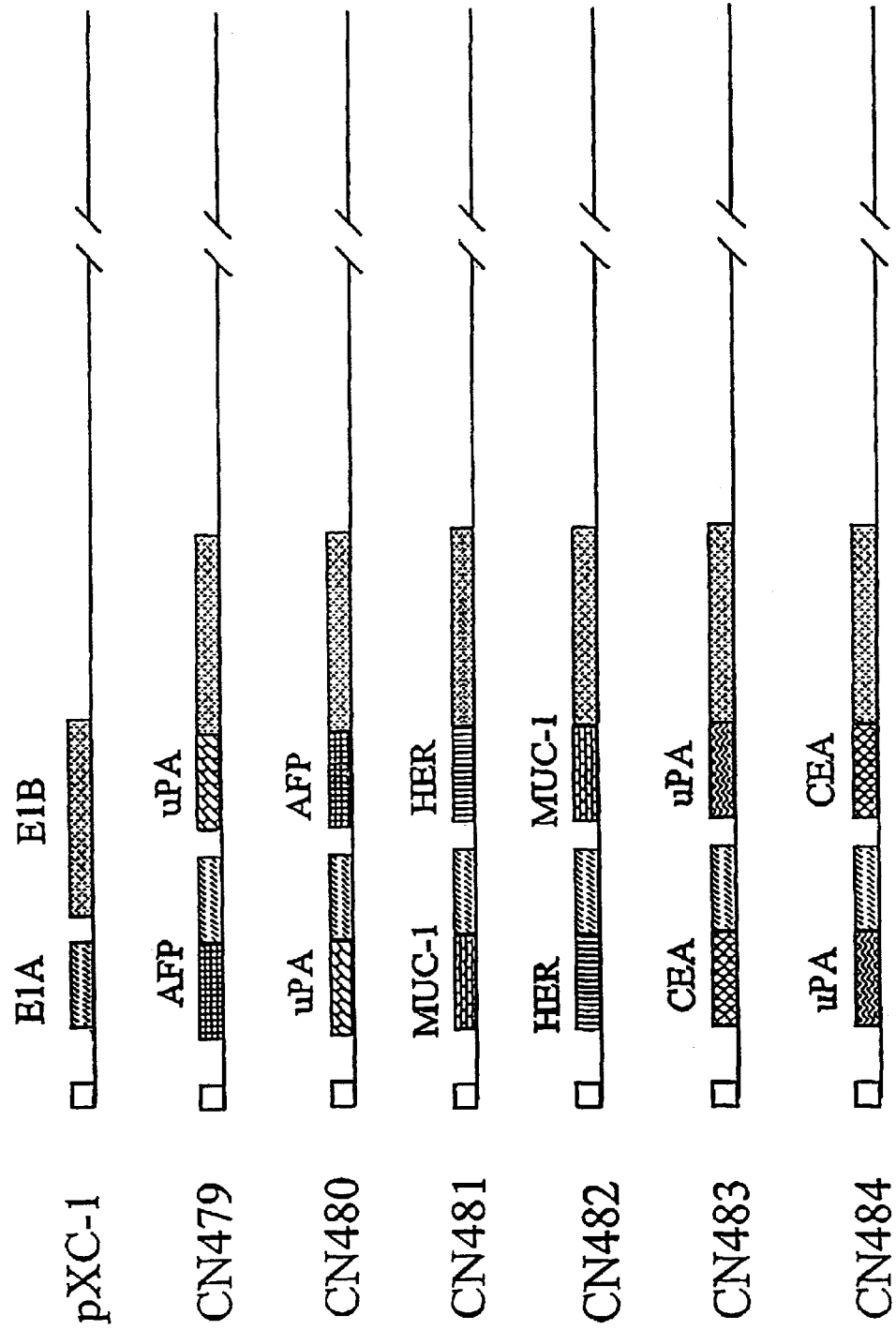
FIGS. 8(A)–(B) are schematic diagrams of examples of adenovirus vectors in which the E1A and E1B genes are under transcriptional control of cell specific heterologous TREs. Each adenovirus vector contains at least two different heterologous TREs, both of which are functional in the same cell.
Figure 8B:
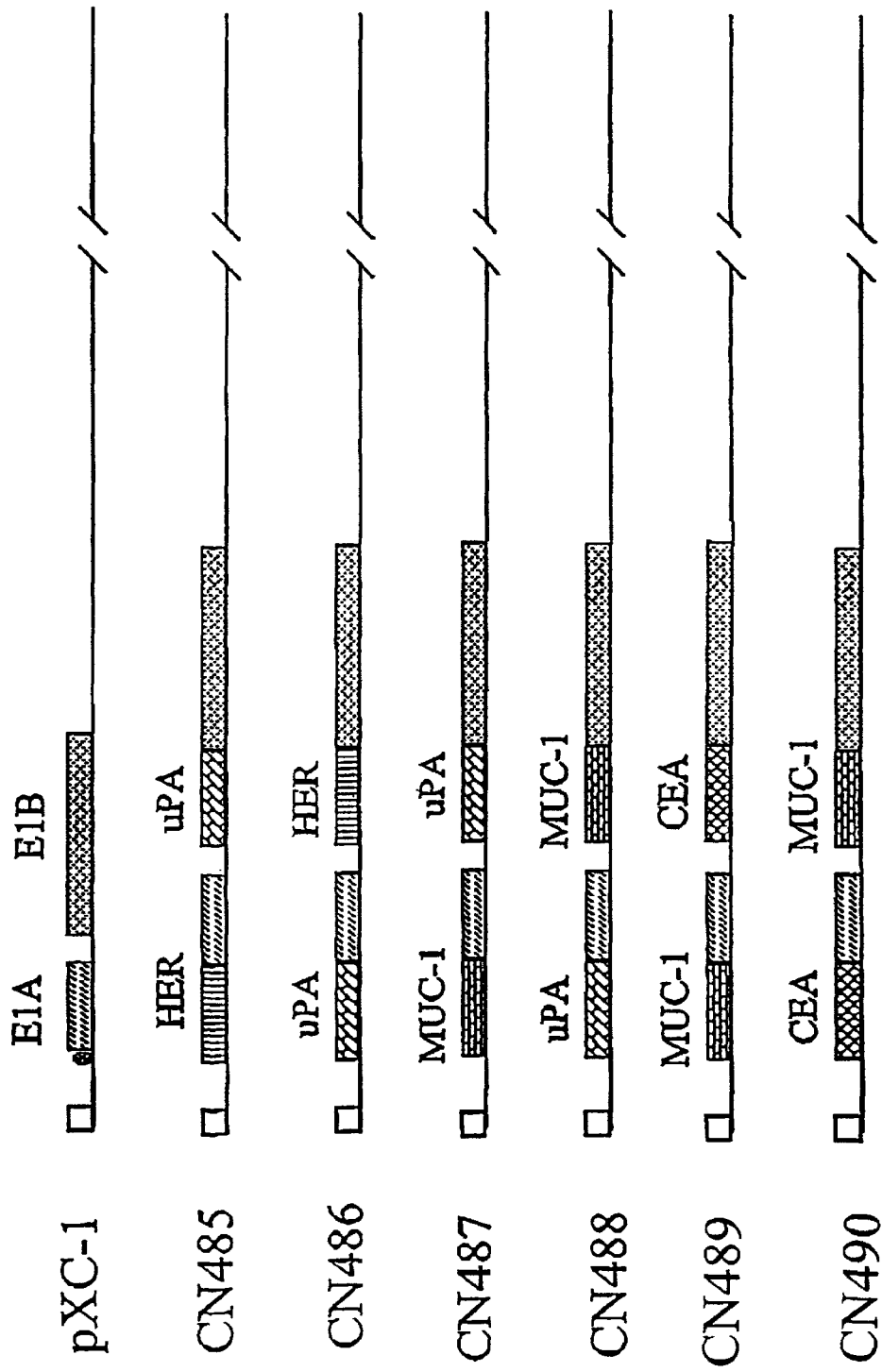

Construction of other Adenovirus Constructs Comprising a First Adenoviral Gene Under Control of a Cell Specific Heterologous TRE and at Least a Second Gene Under Control of a Second Heterologous TRE, where Both Heterologous TREs are Functional in the Same Cell Adenovirus vectors containing heterologous TREs may be generated so as to target the adenoviral replication to a variety of neoplasia. The following describes examples of cell specific (in some cases, tumor cell specific) TREs that may be used to control the expression of adenovirus genes so as to lead to replication of the adenovirus vectors preferentially in the target cells as compared to non-target cells. Cell specific adenovirus vectors are listed under a type of neoplsia for which the vectors may provide a treatment. Several of the adenovirus vectors may be useful in the treatment of more than one type of neoplasia because the TREs are functional in more than one type of tumor cell, as described herein. Schematic diagrams of exemplary adenovirus vectors are depicted in FIGS. 8 (A)–(B).

Generation of Liver Neoplasia Specific Adenovirus Vectors

As described above, TREs from the AFP gene have been shown to be specifically active in liver neoplasia. Human AFP enhancer domains A and B (included in the region −3954 bp to −3335 bp relative to the AFP cap site) were PCR amplified from human genomic DNA using the following primers:

5' GTGACCGGTGCATTGCTGTGAACTCTGTA 3' (39.055B) (SEQ ID NO:23) and

5' ATAAGTGGCCTGGATAAAGCTGAGTGG 3' (39.044D) (SEQ ID NO:24)

The AFP promoter was amplified from −163 to +34 using the following primers:

5' GTCACCGGTCTTTGTTATTGGCAGTGGT 3' (39.055J) (SEQ ID NO:25)

5' ATCCAGGCCACTTATGAGCTCTGTGTCCTT 3' (29.055M) (SEQ ID NO:26)

The enhancer and promoter segments were annealed, and a fusion construct was generated using overlap PCR with primers 39.055B and 39.055J. This minimal enhancer/promoter fragment was digested with PinAI and ligated with CN124 using the engineered AgeI site 5' of the E1A cap site to produce CN219. In CN219, the AFP-TRE is immediately upstream of and operably linked to the E1A coding sequence.

The AFP-TRE described above was amplified with the following primers (EagI sites under lined):

5' TATCGGCCGGCATTGCTGTGAACTCT 3' (39.077A) (SEQ ID NO:27) and

5' TTACGGCCGCTTTGTTATTGGCAGTG 3' (39.077C) (SEQ ID NO:28)

The PCR product was digested with EagI and ligated into the EagI site immediately upstream of the E1B gene in CN124 to make CN234. In CN234, the AFP-TRE is immediately upstream of and operably linked to the E1B coding sequence.

uPA promoter and the other transcription response element (Riccio et al. (1985) *Nucleic Acids Res.* 13:2759–2771; Cannio et al. (1991) *Nucleic Acids Res.* 19:2303–2308) are amplified by PCR with EagI sites at the ends and ligated into EagI digested CN219, to generate CN479. CN479 is a construct with the AFP-TRE operably linked to E1A and uPA-TRE operably linked to E1B. Similarly, uPA-TRE is engineered into CN234 at the PinAI site, to produce CN480. CN480 is a construct in which E1A is under transcriptional control of uPA-TRE and E1B is under transcriptional control of AFP-TRE.

Generation of Breast Cancer Cell Specific Adenovirus Vectors

As described above, TREs from the MUC1 gene have been identified that are specifically active in breast cancer cells. An adenovirus vector in which expression of the E1A gene is under control of MUC1-TRE was constructed as follows.

The MUC1-TRE region of SEQ ID NO:29 was amplified from human genomic DNA by PCR with the following primer pairs:

5' TAA TCC GGA COG TGA CCA CTA GAG GG 3' (39.088A, SEQ ID NO:30) and

5' TAT TCC GGA TCA CTT AGG CAG CGC TG 3' (39.088B, SEQ ID NO:31).

The primers were constructed with BspEI ends, which are compatible with the AgeI site in CN124. As described herein, CN124 has an AgeI site at Ad5 nt 547 (just upstream of the E1A transcriptional start at nt 498 and the E1A coding segment beginning with ATG at 610) and an EagI site at Ad5 nt 1682, or just upstream of the E1B coding segment. The MUC1-TRE PCR product was digested with BspI and ligated into the AgeI site of CN124 to make CN226. In CN226, the MUC1-TRE is immediately upstream of and operably linked to the E1A coding sequence.

The MUC1-TRE was amplified from CN226 to include EagI ends with the following primer pairs:

5' TAA CGG CCG CGG TGA CCA CTA GAG 3' (39.120A, SEQ ID NO:32) and

5' TAT COG CCG GCA GAA CAG ATT CAG 3' (39.120B, SEQ ID NO:33).

The MUC1-TRE PCR product was digested with EagI and ligated in the EagI site CN124 to make CN292. In CN292, the MUC1-TRE is immediately upstrem of and operably linked to the E1B gene.

Human HER-2/neu (HER)-TRE (Tal et al. (1987) *Mol. Cell. Biol.* 7:2597–2601; Hudson et al. (1990) *J. Biol. Chem.* 265:4389-4393; Grooteclaes et al. (1994) *Cancer Res.* 54:4193–4199; Ishii et al. (1987) *Proc. Natl. Acad. Sci. USA* 84:4374–4378; Scott et al. (1994) *J. Biol. Chem.* 269:19848–19858) is amplified from human genomic DNA with an EagI site at end, ligated into a EagI cut CN226, to produce CN481. CN481 is a construct in which the MUC1-TRE is operably linkedad to the E1A gene and HER-TRE is operably linked to the E1B gene. Similarly, HER-TRE is amplified from CN481 by PCR with PinAI site at the end, and ligated into a similarly cut CN292; to produce CN482. CN482 is a construct in which the HER-TRE is operably linked to the E1A gene and the MUC1-TRE is operably linked to the E1B gene.

Another set of breast cancer cell specific adenoviral vectors is generated when the uPA-TRE is released from CN485 with EagI and ligated into a similarly cut CN481, to produce CN487. CN487 is a construct in which the MUC1-TRE is operably linked to the E1A gene and the uPA-TRE is operably linked to the E1B gene. CN488 is the same as CN487 except the positions of two heterologousTREs are exchanged. CN488 is a construct in which the uPA-TRE is operably linked to the E1A gene and the MUC1-TRE is operably linked to the E1B gene.

Another set of breast cancer cell specific adenoviral vectors is generated when the CEA-TRE is released from CN484 with EagI and ligated into a similarly cut CN487, to produce CN489. CN489 is a construct in which the MUC1-TRE is operably linked to the E1A gene and the CEA-TRE is operably linked to the E1B gene. CN490 is the same as CN489 except the positions of two heterologousTREs are exchanged. CN490 is a construct in which the CEA-TRE is operably linked to the E1A gene and the MUC1-TRE is operably linked to the E1B gene.

Generation of Colon Cancer Cell Specific Adenovirus Vectors

As described above, TREs from the CEA gene have been identified that are specifically active in a number of neoplasia including colon cancers. An adenovirus vector in which expression of the E1A gene is under control of CEA-TRE was constructed as follows.

A TRE of the carcinoembryonic antigen (CEA-TRE), about −402 to about +69 bp relative to the transcriptional start (SEQ ID NO:7), was amplified by PCR from human genomic DNA using primers(which introduced AgeI sites at the ends):

5' ATT ACC GGT AGC CAC CAC CCA GTG AG 3' (39.174B, SEQ ID NO:34) and

5' TAG ACC GGT GCT TGA GTT CCA GGA AC 3' (39.174D, SEQ ID NO:35).

The CEA-TRE PCR fragment was ligated into pGEM-T vector which had been linearized with EcoRV and designated CN265. The CEA-TRE was excised from CN265 by digestion with PinAI and was ligated into similarly digested CN124 to generate CN266. CN266 is a construct in which the CEA-TRE is operably linked to the E1A gene.

The CEA-TRE was amplified from CN266 by PCR using primers:

5' TAA CGG CCG AGC CAC CAC CCA 3' (39.180A, SEQ ID NO:36) and

5' TAT CGG CCG GCT TGA GTT CCA GG 3' (39.180B, SEQ ID NO:37)

The unique restriction site EagI was introduced by the primer pair at the ends of the PCR amplified product. The PCR product was ligated into pGEM-T Vector (Promega), and the resultant plasmid designated CN284. The EagI CEA-TRE fragment was excised from CN284 and isolated by gel electrophoresis, and ligated into CN124 which had been cut with EagI to make CN290. CN290 is a construct in which the CEA-TRE is immediately upstream of and operably linked to the E1B gene.

A uPA-TRE is released from CN479 with EagI and ligated into a similarly cut CN266, to produce CN483. CN483 is a construct in which the CEA-TRE is operably linked to the E1A gene and the uPA-TRE is operably linked to the E1B gene. Similarly, CN484 is a construct in which the uPA-TRE is operably linked to the E1A gene and the CEA-TRE is operably linked to the E1B gene.

Generation of Colon Cancer Cell Specific Adenovirus Vectors

CN485 is a construct in which the HER-TRE is operably linked to the E1A gene and the uPA-TRE is operably linked to the E1B gene. uPA-TRE is released from CN479 with EagI and ligated to a similarly cut CN482, to produce CN485.

CN486 is the same as CN485 except the position of two heterologous TREs are exchanged. CN486 is a construct in which the uPA-TRE is operably linked to the E1A gene and the HER-TRE is operably linked to the E1B gene.

Generation Additional Adenovirus Vectors Containing Multiple Heterologous TREs

The invention does not exclude additional genes under transcriptional control of heterologous TREs. Accordingly, adenovirus vectors may be generated in which a third gene is under trascriptional control of a third heterologous TRE, where all the TREs are different from each other and all are functional in the same cell.

Figure 9:
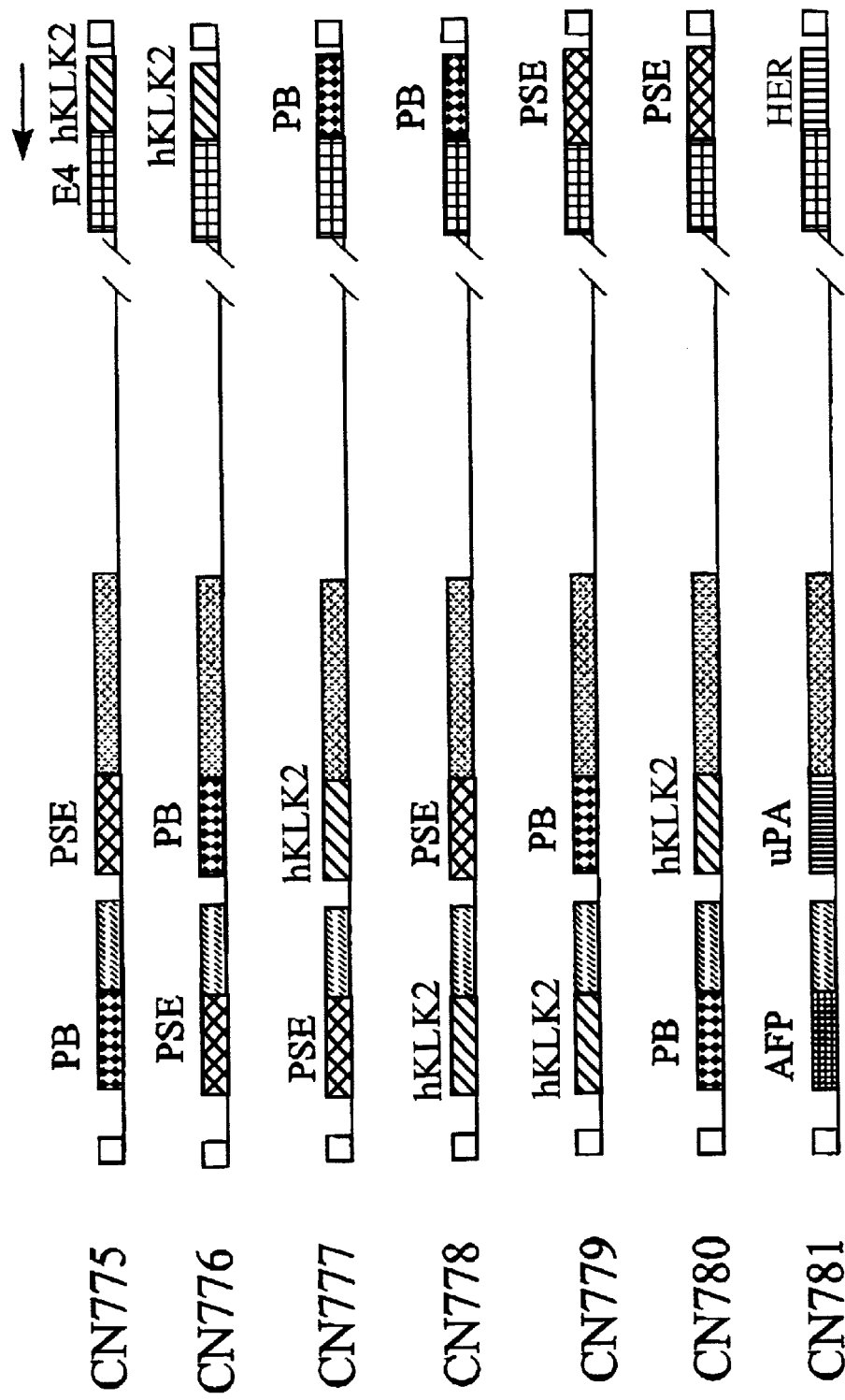
FIG. 9 depicts schematic diagrams of examples of adenovirus vectors in which the E1A, E1B, and E4 genes are under transcriptional control of cell specific heterologous TREs. Each adenovirus vector contains three different heterologous TREs, all of which are functional in the same cell.

An adenovirus vector is generated through the insertion of the PB-TRE, the PSE-TRE, and the hKLK2-TRE in operable linkage with three genes, for example, the E1A, E1B, and E4 genes. These prostate cell specific TREs are amplified as described above and inserted into the adenovirus vectors as described herein. FIG. 9 depicts examples of such adenoviral constructs.

Also depicted in FIG. 9 is an example of a construct in which three genes are controlled by three other cell specific TREs described above. The adenovirus construct CN781, for example, may be useful to target liver neoplasia in which the HER-TRE is functional.

Adenoviruses that contain multiple heterologous TREs are generated by homologous recombination in 293 cells as described above.

Example 6

Characterization of an E3 Deleted Adenovirus, CN751, that Contains the Adenovirus Death Protein Gene An Adenovirus death protein mutant, CN751, was constructed to test whether such a construct may be more effective for cytotoxicity. The Adenovirus death protein (ADP), an 11.6 kD Asn-glycosylated integral membrane peptide expressed at high levels late in infection, migrates to the nuclear membrane of infected cells and affects efficient lysis of the host. The Adenovirus 5 (Ad5) E3 region expresses the adp gene.

Construction of CN751

CN751 was constructed in two parts. First, an E3 deleted platform plasmid that contains Ad5 sequence 3' from the BamHI site at 21562 bp was generated. The Ad2 adp was engineered into the remainder of the E3 region of this plasmid to yield CN252. An ADP cassette is constructed using overlap PCR. The Y leader, an important sequence for correct expression of some late genes, is PCR-amplified using primers:

5' GCCTTAATTAAAAGCAAACCTCACCTCCG ... Ad2 28287 bp (37.124.1) (SEQ ID NO:38); and 5' GTGGAACAAAAGGTGATTAAAAAATCCCAG ... Ad2 28622 bp (37.146.1) (SEQ ID NO:39).

The ADP coding region is PCR amplified using primers:

5' CACCTTTTGTTCCACCGCTCTGCTTATTAC ... Ad2 29195 bp (37.124.3) (SEQ ID NO:40) and 5' GGCTTAATTAACTGTGAAAGGTGGGAGC ... Ad2 29872 bp (37.124.4) (SEQ ID NO:41).

The two fragments were annealed and the overlap product was PCR amplified using primers 37.124.1 and 37.124.4. The ends of the product were polished with Klenow fragment and ligated to BamHI cut pGEM-72 (+) (CN241; Promega, Madison, Wis.). The ADP cassette was excised by digesting CN241 with Pac 1 restriction endonuclease and ligated with two vectors, CN247 and CN248 generating plasmids CN252 and CN270, respectively. CN247 contains a unique PacI site in the E3 region and was constructed as follows. A plasmid containing the full length Ad5 genome, TG3602 (Transgene, France), was digested with BamHI and religated to yield CN221. The backbone of this plasmid (outside of the Ad5 sequence) contained a PacI site that needed to be removed to enable further manipulations. This was effected by digesting CN221 with PacI and polishing the ends with T4 DNA polymerase, resulting in CN246. CN246 was digested with AscI and AvrII (to remove intact E3 region). This fragment was replaced by a similarly cut fragment derived from BHG11. The resulting plasmid, CN247, contained a deleted E3 region and a PacI site suitable for insertion of the ADP cassette fragment (described above). Ligation of CN247 with the ADP cassette generated CN252.

To construct the second part, the 5' Ad5 sequence necessary for CN751 was obtained by digesting purified CN702 DNA with EcoRI and isolating the left hand fragment by gel extraction. After digesting CN252 with EcoRI, the left hand fragment of CN702 and CN252 were ligated. 293 cells were transfected with this ligation mixture by using the standard lipofection transfection protocol developed at Calydon, Inc. and incubated at 37° C. Ten days later, the cells were harvested, freeze-thawed three times, and the supernatant was plaqued on 293 monolayers. Individual plaques were picked and used to infect monolayers of 293 cells to grow enough virus to test. After several days, plate lysates were screened using a polymerase chain reaction (PCR) based assay to detect candidate viruses. One of the plaques that scored positive was designated CN751.

Structural Characterization of CN751

The structure of CN751 was confirmed by two methods. First, primers 37.124.1 and 37.124.4 were used to screen candidate viruses by PCR to detect the presence of the adp cassette. CN751 produced an extension fragment consistent with the expected product (1065 bp). Second, CN751 was analyzed by Southern blot. Viral DNA was purified, digested with PacI, SacI, and AccI/XhoI, and probed with a sequence homologous to the ADP coding region. The structure of CN751 matched the expected pattern.

In Vitro Characterization of CN751

Two experiments were conducted to examine the cytotoxicity and virus yield of CN751. In the first study, CN751's cytotoxicity was evaluated in LNCaP cells by measuring the accumulation of a cytosolic enzyme, lactate dehydrogenase (LDH), in the supernatant over several days. The level of extracellular LDH correlates with the extent of cell lysis. Healthy cells release very little, if any, enzyme, whereas dead cells release large quantities. LDH was chosen as a marker because it is a stable protein that can be readily detected by a simple protocol. CN751's ability to cause cell death was compared to that of CN702, a vector lacking the ADP gene, and Rec700, a vector containing the ADP gene.

Monolayers of LNCaP cells were infected at a multiplicity of infection of one with either CN702, Rec700, or CN751 and then seeded in 96 well dishes. Samples were harvested once a day from one day after infection to five days after infection and scored using Promega's Cytotox 96 kit. This assay uses a coupled enzymatic reaction which converts a tetrazolium salt to a red formazan product that can be determined in a plate reader at 490 nm.

Figure 10:
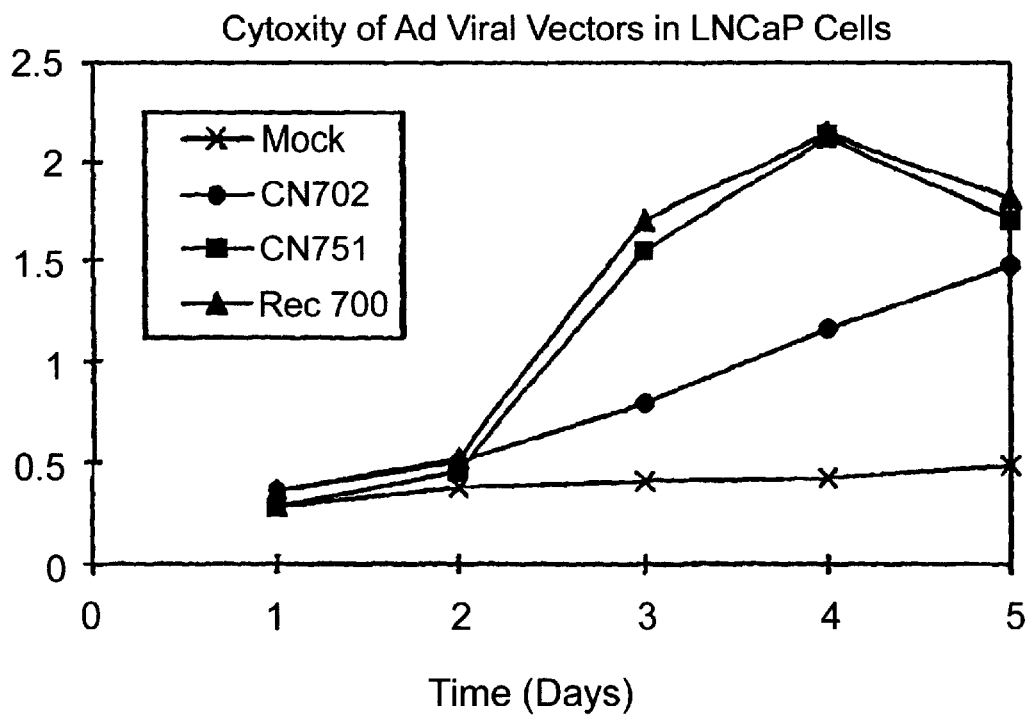
FIG. 10 is a graph depicting cytotoxicity of an adenoviral vector containing the coding sequence for adenoviral death protein (ADP), CN751 (solid squares), compared to control CN702 (solid circles), Rec 700 (solid triangles) and mock infection (Xs).

Since the absorbance of a sample corresponds to the level of LDH released from infected cells, a plot of how a sample's absorbance changes with time describes how efficiently the viruses studied induce cell lysis (FIG. 10). Each data point represents the average of sixteen separate samples. The results suggest that CN751 kills cells more efficiently than the adp- control, CN702, and similarly to the adp+ control, Rec700. The concentration of LDH in the supernatant increases rapidly from two days and reaches a maximum at four days in wells infected with CN751. In contrast, LDH concentration in the supernatant of CN702 infected cells begins to rise slowly at two days and continues until the conclusion of the experiment. Significantly, the amount of LDH released from CN751 infected cells at three days is two times that released from CN702 infected cells. The data demonstrate that adenovirus vectors with adp gene kill cells more efficiently than adenovirus vectors that lack the adp gene.

Figure 11:
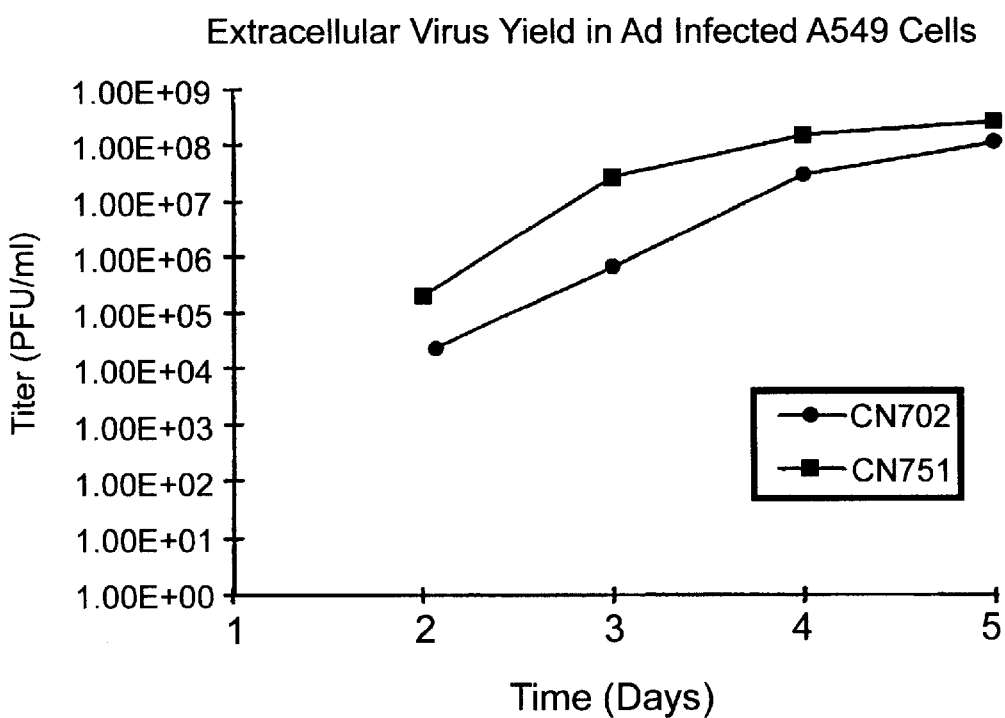
FIG. 11 is a graph comparing extracellular virus yield of CN751 (solid squares) and CN702 (solid circles).

Not only is it important for adenovirus vectors to kill cells efficiently, they must also be able to shed progeny that can infect other target cells. Viral vectors that can shed large amounts of virus might be better therapeutics than those that shed only small amounts. A virus yield assay was undertaken to evaluate whether CN751 can induce the efficient release of its progeny from the infected cell. A549 cells were infected at an MOI of five. Supernatant was harvested at various times after infection and titered on 293 cells to determine the virus yield (FIG. 11). The data suggests that cells infected with CN751 shed virus more efficiently than those infected with CN702. At forty-eight hours post infection, CN751 infected cells have released ten times more virus than CN702 infected. At seventy-two hours post infection, CN751 infected cells have released forty times more virus. In sum, the virus yield data demonstrate that adenovirus vectors with the adp gene release more virus.

In Vivo Characterization of CN751

Figure 12:
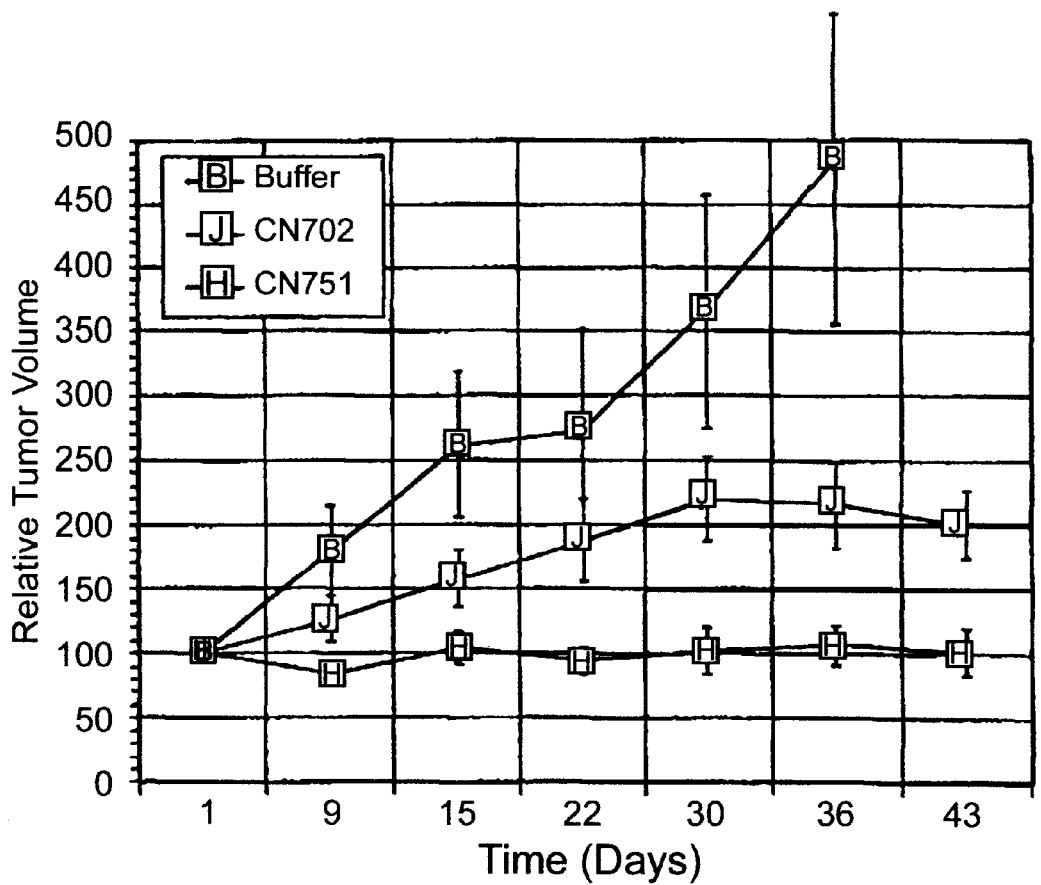
FIG. 12 is a graph comparing tumor volume in mice harboring LNCaP tumor xenografts challenged with CN751 ("H"), CN702 ("J"), or buffer ("B").

LNCaP nude mouse xenografts were challenged with a single intratumoral dose ($1\times10^4$ particles/mm$^3$ tumor) of either CN751, a vector containing the ADP gene, or CN702, a vector lacking the gene. A third group of tumors was treated with buffer alone. The tumors were monitored weekly for six weeks and their relative volume was graphed against time. The results are shown in FIG. 12. Error bars represent the standard error for each sample group. The initial average tumor volume for CN751 treated animals (n=14) was 320 mm$^3$ for CN702 treated (n=14), and 343 mm$^3$ for buffer. treated (n=8). The data suggest that CN751 kills tumor cells more effectively than CN702. On average, tumors challenged with CN751 remained the same size throughout the course of the experiments while nine out of fourteen tumors (64%) regressed. Those treated with CN702 doubled in size. Buffer treated tumors grew to nearly five times their initial volume. The Students T-test indicates that the difference in tumor size between CN751 and CN702 treated tumors was statistically significant from day 7 (p=0.016) through the end of the experiment (p=0.003).

All publications and patent applications mentioned in this specification are herein incorporated by reference to the same extent as if each individual publication or patent application was specifically and individually indicated to be incorporated by reference.

Although the foregoing has been described in some detail by way of illustration and example for purposes of clarity of understanding, it will be apparent to those skilled in the art that certain changes and modifications can be practiced. Therefore, the description and examples should not be construed as limiting the scope of the invention, which is delineated by the appended claims.

What is claimed is:

1. A replication-competent adenovirus vector for selective cytolysis of a target cell, comprising:
    a first adenovirus gene essential for replication under transcriptional control of a first heterologous transcriptional regulatory element (TRE) and at least a second adenovirus gene under transcriptional control of a second heterologous TRE, wherein the first and the second heterologous TREs are cell-specific, the first heterologous is different from the second heterologous TRE, and the heterologous TREs are functional in the same cell.

2. The adenovirus vector of claim 1, wherein said adenovirus gene essential for replication is an adenovirus early gene.

3. The adenovirus vector of claim 2, wherein said gene essential for replication is the adenovirus E1A gene.

4. The adenovirus vector of claim 1, wherein said gene essential for replication is an adenovirus late gene.

5. The adenovirus vector of claim 1, wherein said second adenovirus gene is essential for replication.

6. The adenovirus vector of claim 5, wherein said first and second genes are adenovirus early genes.

7. The adenovirus vector of claim 1, wherein said vector comprises a cytotoxic gene.

8. The adenovirus vector of claim 1, wherein the first heterologous TRE is prostate cell-specific.

9. The adenovirus vector of claim 1, wherein the first heterologous TRE is a PSA-TRE.

10. An isolated host cell comprising the adenovirus vector of claim 1.

11. A composition comprising the adenovirus vector of claim 1 and a pharmaceutically acceptable excipient.

12. The adenovirus vector of claim 1, wherein said first heterologous TRE is selected from the group consisting of a prostate-specific antigen (PSA) transcriptional regulatory element (PSA-TRE), a probasin transcriptional regulatory element (PB-TRE), a human glandular kallikrein transcriptional regulatory element (HKLK2-TRE), a carcinoembryonic antigen transcriptional regulatory element (CEA-TRE), an α-fetoprotein transcriptional regulatory element (AFP-TRE), a urokinase-type plasminogen activator transcriptional regulatory element (uPA TRE); a mucin transcriptional regulatory element (MUC1-TRE) and a HER-2/neu transcriptional regulatory element (HER-2/neu TRE).

13. The adenovirus vector of claim 12, wherein said adenovirus gene essential for replication is an adenovirus early gene.

14. The adenovirus vector of claim 12, wherein said vector comprises a therapeutic gene.

15. The adenovirus vector of claim 12, wherein said vector comprises a cytotoxic gene.

16. An isolated host cell comprising the adenovirus vector of claim 12.

17. A composition comprising the adenovirus vector of claim 12, and a pharmaceutically acceptable excipient.

* * * * *

UNITED STATES PATENT AND TRADEMARK OFFICE
CERTIFICATE OF CORRECTION

PATENT NO. : 6,432,700 B1 Page 1 of 1
DATED : August 13, 2002
INVENTOR(S) : Henderson, Daniel R. et al.

It is certified that error appears in the above-identified patent and that said Letters Patent is hereby corrected as shown below:

<u>Column 8,</u>
Line 11, please correct as follows:
-- deoxyribonucleotides --

<u>Column 92,</u>
Line 65, please correct as follows:
-- heterologous TRE is different from the second heterologous --

Signed and Sealed this

Fifteenth Day of July, 2003

JAMES E. ROGAN
*Director of the United States Patent and Trademark Office*

SEQUENCE LISTING (1) GENERAL INFORMATION:

(iii) NUMBER OF SEQUENCES: 41

(2) INFORMATION FOR SEQ ID NO:1:

(i) SEQUENCE CHARACTERISTICS:
        (A) LENGTH: 5836 base pairs
        (B) TYPE: nucleic acid
        (C) STRANDEDNESS: single (D) TOPOLOGY: linear (xi) SEQUENCE DESCRIPTION: SEQ ID NO:1:

```
AAGCTTCTAG TTTTCTTTTC CCGGTGACAT CGTGGAAAGC ACTAGCATCT CTAAGCAATG    60
ATCTGTGACA ATATTCACAG TGTAATGCCA TCCAGGGAAC TCAACTGAGC CTTGATGTCC   120
AGAGATTTTT GTGTTTTTTT CTGAGACTGA GTCTCGCTCT GTGCCAGGCT GGAGTGCAGT   180
GGTGCAACCT TGGCTCACTG CAAGCTCCGC CTCCTGGGTT CACGCCATTC TCCTGCCTCA   240
GCCTCCTGAG TAGCTGGGAC TACAGGCACC CGCCACCACG CCTGGCTAAT TTTTTTGTAT   300
TTTTAGTAGA GATGGGGTTT CACTGTGTTA GCCAGGATGG TCTCAGTCTC CTGACCTCGT   360
GATCTGCCCA CCTTGGCCTC CCAAAGTGCT GGGATGACAG GCGTGAGCCA CCGCGCCTGG   420
CCGATATCCA GAGATTTTTT GGGGGGCTCC ATCACACAGA CATGTTGACT GTCTTCATGG   480
TTGACTTTTA GTATCCAGCC CCTCTAGAAA TCTAGCTGAT ATAGTGTGGC TCAAAACCTT   540
CAGCACAAAT CACACCGTTA GACTATCTGG TGTGGCCCAA ACCTTCAGGT GAACAAAGGG   600
ACTCTAATCT GGCAGGATAT CCAAAGCAT  TAGAGATGAC CTCTTGCAAA GAAAAAGAAA   660
TGGAAAAGAA AAAGAAAGAA AGGAAAAAAA AAAAAAAAAA GAGATGACCT CTCAGGCTCT   720
GAGGGGAAAC GCCTGAGGTC TTTGAGCAAG GTCAGTCCTC TGTTGCACAG TCTCCCTCAC   780
AGGGTCATTG TGACGATCAA ATGTGGTCAC GTGTATGAGG CACCAGCACA TGCCTGGCTC   840
TGGGGAGTGC CGTGTAAGTG TATGCTTGCA CTGCTGAATG CTTGGGATGT GTCAGGGATT   900
ATCTTCAGCA CTTACAGATG CTCATCTCAT CCTCACAGCA TCACTATGGG ATGGGTATTA   960
CTGGCCTCAT TTGATGGAGA AAGTGGCTGT GGCTCAGAAA GGGGGGACCA CTAGACCAGG  1020
GACACTCTGG ATGCTGGGGA CTCCAGAGAC CATGACCACT CACCAACTGC AGAGAAATTA  1080
ATTGTGGCCT GATGTCCCTG TCCTGGAGAG GGTGGAGGTG GACCTTCACT AACCTCCTAC  1140
CTTGACCCTC TCTTTTAGGG CTCTTTCTGA CCTCCACCAT GGTACTAGGA CCCCATTGTA  1200
TTCTGTACCC TCTTGACTCT ATGACCCCCA CTGCCCACTG CATCCAGCTG GGTCCCCTCC  1260
TATCTCTATT CCCAGCTGGC CAGTGCAGTC TCAGTGCCCA CCTGTTTGTC AGTAACTCTG  1320
AAGGGGCTGA CATTTTACTG ACTTGCAAAC AAATAAGCTA ACTTTCCAGA GTTTTGTGAA  1380
TGCTGGCAGA GTCCATGAGA CTCCTGAGTC AGAGGCAAAG GCTTTTACTG CTCACAGCTT  1440
AGCAGACAGC ATGAGGTTCA TGTTCACATT AGTACACCTT GCCCCCCCCA AATCTTGTAG  1500
GGTGACCAGA GCAGTCTAGG TGGATGCTGT GCAGAAGGGG TTTGTGCCAC TGGTGAGAAA  1560
CCTGAGATTA GGAATCCTCA ATCTTATACT GGGACAACTT GCAAACCTGC TCAGCCTTTG  1620
TCTCTGATGA AGATATTATC TTCATGATCT TGGATTGAAA ACAGACCTAC TCTGGAGGAA  1680
CATATTGTAT CGATTGTCCT TGACAGTAAA CAAATCTGTT GTAAGAGACA TTATCTTTAT  1740
TATCTAGGAC AGTAAGCAAG CCTGGATCTG AGAGAGATAT CATCTTGCAA GGATGCCTGC  1800
TTTACAAACA TCCTTGAAAC AACAATCCAG AAAAAAAAAG GTGTTGCTGT CTTTGCTCAG  1860
AAGACACACA GATACGTGAC AGAACCATGG AGAATTGCCT CCCAACGCTG TTCAGCCAGA  1920
GCCTTCCACC CTTGTCTGCA GGACAGTCTC AACGTTCCAC CATTAAATAC TTCTTCTATC  1980
ACATCCTGCT TCTTTATGCC TAACCAAGGT TCTAGGTCCC GATCGACTGT GTCTGGCAGC  2040
ACTCCACTGC CAAACCCAGA ATAAGGCAGC GCTCAGGATC CCGAAGGGGC ATGGCTGGGG  2100
ATCAGAACTT CTGGGTTTGA GTGAGGAGTG GGTCCACCCT CTTGAATTTC AAAGGAGGAA  2160
GAGGCTGGAT GTGAAGGTAC TGGGGGAGGG AAAGTGTCAG TTCCGAACTC TTAGGTCAAT  2220
GAGGGAGGAG ACTGGTAAGG TCCCAGCTCC CGAGGTACTG ATGTGGGAAT GGCCTAAGAA  2280
```

```
TCTCATATCC TCAGGAAGAA GGTGCTGGAA TCCTGAGGGG TAGAGTTCTG GGTATATTTG    2340

TGGCTTAAGG CTCTTTGGCC CCTGAAGGCA GAGGCTGGAA CCATTAGGTC CAGGGTTTGG    2400

GGTGATAGTA ATGGGATCTC TTGATTCCTC AAGAGTCTGA GGATCGAGGG TTGCCCATTC    2460

TTCCATCTTG CCACCTAATC CTTACTCCAC TTGAGGGTAT CACCAGCCCT TCTAGCTCCA    2520

TGAAGGTCCC CTGGGCAAGC ACAATCTGAG CATGAAAGAT GCCCCAGAGG CCTTGGGTGT    2580

CATCCACTCA TCATCCAGCA TCACACTCTG AGGGTGTGGC CAGCACCATG ACGTCATGTT    2640

GCTGTGACTA TCCCTGCAGC GTGCCTCTCC AGCCACCTGC CAACCGTAGA GCTGCCCATC    2700

CTCCTCTGGT GGGAGTGGCC TGCATGGTGC CAGGCTGAGG CCTAGTGTCA GACAGGGAGC    2760

CTGGAATCAT AGGGATCCAG GACTCAAAAG TGCTAGAGAA TGGCCATATG TCACCATCCA    2820

TGAAATCTCA AGGGCTTCTG GGTGGAGGGC ACAGGGACCT GAACTTATGG TTTCCCAAGT    2880

CTATTGCTCT CCCAAGTGAG CTCCCCAGAT ACGAGGCACT GTGCCAGCAT CAGCCTTATC    2940

TCCACCACAT CTTGTAAAAG GACTACCCAG GGCCCTGATG AACACCATGG TGTGTACAGG    3000

AGTAGGGGGT GGAGGCACGG ACTCCTGTGA GGTCACAGCC AAGGGAGCAT CATCATGGGT    3060

GGGGAGGAGG CAATGGACAG GCTTGAGAAC GGGGATGTGG TTGTATTTGG TTTTCTTTGG    3120

TTAGATAAAG TGCTGGGTAT AGGATTGAGA GTGGAGTATG AAGACCAGTT AGGATGGAGG    3180

ATCAGATTGG AGTTGGGTTA GATAAAGTGC TGGGTATAGG ATTGAGAGTG GAGTATGAAG    3240

ACCAGTTAGG ATGGAGGATC AGATTGGAGT TGGGTTAGAG ATGGGGTAAA ATTGTGCTCC    3300

GGATGAGTTT GGGATTGACA CTGTGGAGGT GGTTTGGGAT GGCATGGCTT TGGGATGGAA    3360

ATAGATTTGT TTTGATGTTG GCTCAGACAT CCTTGGGGAT TGAACTGGGG ATGAAGCTGG    3420

GTTTGATTTT GGAGGTAGAA GACGTGGAAG TAGCTGTCAG ATTTGACAGT GGCCATGAGT    3480

TTTGTTTGAT GGGGAATCAA ACAATGGGGG AAGACATAAG GGTTGGCTTG TTAGGTTAAG    3540

TTGCGTTGGG TTGATGGGGT CGGGGCTGTG TATAATGCAG TTGGATTGGT TTGTATTAAA    3600

TTGGGTTGGG TCAGGTTTTG GTTGAGGATG AGTTGAGGAT ATGCTTGGGG ACACCGGATC    3660

CATGAGGTTC TCACTGGAGT GGAGACAAAC TTCCTTTCCA GGATGAATCC AGGGAAGCCT    3720

TAATTCACGT GTAGGGGAGG TCAGGCCACT GGCTAAGTAT ATCCTTCCAC TCCAGCTCTA    3780

AGATGGTCTT AAATTGTGAT TATCTATATC CACTTCTGTC TCCCTCACTG TGCTTGGAGT    3840

TTACCTGATC ACTCAACTAG AAACAGGGGA AGATTTTATC AAATTCTTTT TTTTTTTTTT    3900

TTTTTTTGA GACAGAGTCT CACTCTGTTG CCCAGGCTGG AGTGCAGTGG CGCAGTCTCG     3960

GCTCACTGCA ACCTCTGCCT CCCAGGTTCA AGTGATTCTC CTGCCTCAGC CTCCTGAGTT    4020

GCTGGGATTA CAGGCATGCA GCACCATGCC CAGCTAATTT TTGTATTTTT AGTAGAGATG    4080

GGGTTTCACC AATGTTTGCC AGGCTGGCCT CGAACTCCTG ACCTGGTGAT CCACCTGCCT    4140

CAGCCTCCCA AAGTGCTGGG ATTACAGGCG TCAGCCACCG CGCCCAGCCA CTTTTGTCAA    4200

ATTCTTGAGA CACAGCTCGG GCTGGATCAA GTGAGCTACT CTGGTTTTAT TGAACAGCTG    4260

AAATAACCAA CTTTTTGGAA ATTGATGAAA TCTTACGGAG TTAACAGTGG AGGTACCAGG    4320

GCTCTTAAGA GTTCCCGATT CTCTTCTGAG ACTACAAATT GTGATTTTGC ATGCCACCTT    4380

AATCTTTTTT TTTTTTTTTT TAAATCGAGG TTTCAGTCTC ATTCTATTTC CCAGGCTGGA    4440

GTTCAATAGC GTGATCACAG CTCACTGTAG CCTTGAACTC CTGGCCTTAA GAGATTCTCC    4500

TGCTTCGGTC TCCCAATAGC TAAGACTACA GTAGTCCACC ACCATATCCA GATAATTTTT    4560

AAATTTTTTG GGGGGCCGGG CACAGTGGCT CACGCCTGTA ATCCCAACAC CATGGGAGGC    4620
```

```
TGAGATGGGT GGATCACGAG GTCAGGAGTT TGAGACCAGC CTGACCAACA TGGTGAAACT    4680

CTGTCTCTAC TAAAAAAAAA AAAAATAGAA AAATTAGCCG GGCGTGGTGG CACACGGCAC    4740

CTGTAATCCC AGCTACTGAG GAGGCTGAGG CAGGAGAATC ACTTGAACCC AGAAGGCAGA    4800

GGTTGCAATG AGCCGAGATT GCGCCACTGC ACTCCAGCCT GGGTGACAGA GTGAGACTCT    4860

GTCTCAAAAA AAAAAAATTT TTTTTTTTTT TTTGTAGAGA TGGATCTTGC TTTGTTTCTC    4920

TGGTTGGCCT TGAACTCCTG GCTTCAAGTG ATCCTCCTAC CTTGGCCTCG AAAGTGTTG    4980

GGATTACAGG CGTGAGCCAC CATGACTGAC CTGTCGTTAA TCTTGAGGTA CATAAACCTG    5040

GCTCCTAAAG GCTAAAGGCT AAATATTTGT TGGAGAAGGG GCATTGGATT TTGCATGAGG    5100

ATGATTCTGA CCTGGGAGGG CAGGTCAGCA GGCATCTCTG TTGCACAGAT AGAGTGTACA    5160

GGTCTGGAGA ACAAGGAGTG GGGGGTTATT GGAATTCCAC ATTGTTTGCT GCACGTTGGA    5220

TTTTGAAATG CTAGGGAACT TTGGGAGACT CATATTTCTG GGCTAGAGGA TCTGTGGACC    5280

ACAAGATCTT TTTATGATGA CAGTAGCAAT GTATCTGTGG AGCTGGATTC TGGGTTGGGA    5340

GTGCAAGGAA AAGAATGTAC TAAATGCCAA GACATCTATT TCAGGAGCAT GAGGAATAAA    5400

AGTTCTAGTT TCTGGTCTCA GAGTGGTGCA GGGATCAGGG AGTCTCACAA TCTCCTGAGT    5460

GCTGGTGTCT TAGGGCACAC TGGGTCTTGG AGTGCAAAGG ATCTAGGCAC GTGAGGCTTT    5520

GTATGAAGAA TCGGGGATCG TACCCACCCC CTGTTTCTGT TTCATCCTGG GCATGTCTCC    5580

TCTGCCTTTG TCCCCTAGAT GAAGTCTCCA TGAGCTACAA GGGCCTGGTG CATCCAGGGT    5640

GATCTAGTAA TTGCAGAACA GCAAGTGCTA GCTCTCCCTC CCCTTCCACA GCTCTGGGTG    5700

TGGGAGGGGG TTGTCCAGCC TCCAGCAGCA TGGGGAGGGC CTTGGTCAGC CTCTGGGTGC    5760

CAGCAGGGCA GGGGCGGAGT CCTGGGGAAT GAAGGTTTTA TAGGGCTCCT GGGGGAGGCT    5820

CCCCAGCCCC AAGCTT                                                   5836

(2) INFORMATION FOR SEQ ID NO:2:

(i) SEQUENCE CHARACTERISTICS:
        (A) LENGTH: 5835 base pairs
        (B) TYPE: nucleic acid
        (C) STRANDEDNESS: single
        (D) TOPOLOGY: linear (xi) SEQUENCE DESCRIPTION: SEQ ID NO:2:

AAGCTTCTAG TTTTCTTTTC CCGGTGACAT CGTGGAAAGC ACTAGCATCT CTAAGCAATG     60

ATCTGTGACA ATATTCACAG TGTAATGCCA TCCAGGGAAC TCAACTGAGC CTTGATGTCC    120

AGAGATTTTT GTGTTTTTTT CTGAGACTGA GTCTCGCTCT GTGCCAGGCT GGAGTGCAGT    180

GGTGCAACCT TGGCTCACTG CAAGCTCCGC CTCCTGGGTT CACGCCATTC TCCTGCCTCA    240

GCCTCCTGAG TAGCTGGGAC TACAGGCACC CGCCACCACG CCTGGCTAAT TTTTTTGTAT    300

TTTTAGTAGA GATGGGGTTT CACTGTGTTA GCCAGGATGG TCTCAGTCTC CTGACCTCGT    360

GATCTGCCCA CCTTGGCCTC CCAAAGTGCT GGGATGACAG GCGTGAGCCA CCGCGCCTGG    420

CCGATATCCA GAGATTTTTT GGGGGGCTCC ATCACACAGA CATGTTGACT GTCTTCATGG    480

TTGACTTTTA GTATCCAGCC CCTCTAGAAA TCTAGCTGAT ATAGTGTGGC TCAAAACCTT    540

CAGCACAAAT CACACCGTTA GACTATCTGG TGTGGCCCAA ACCTTCAGGT GAACAAAGGG    600

ACTCTAATCT GGCAGGATAC TCCAAAGCAT TAGAGATGAC CTCTTGCAAA GAAAAAGAAA    660

TGGAAAAGAA AAAGAAAGAA AGGAAAAAAA AAAAAAAAAA GAGATGACCT CTCAGGCTCT    720

GAGGGGAAAC GCCTGAGGTC TTTGAGCAAG GTCAGTCCTC TGTTGCACAG TCTCCCTCAC    780
```

-continued

```
AGGGTCATTG TGACGATCAA ATGTGGTCAC GTGTATGAGG CACCAGCACA TGCCTGGCTC    840

TGGGGAGTGC CGTGTAAGTG TATGCTTGCA CTGCTGAATG GCTGGGATGT GTCAGGGATT    900

ATCTTCAGCA CTTACAGATG CTCATCTCAT CCTCACAGCA TCACTATGGG ATGGGTATTA    960

CTGGCCTCAT TTGATGGAGA AAGTGGCTGT GGCTCAGAAA GGGGGGACCA CTAGACCAGG   1020

GACACTCTGG ATGCTGGGGA CTCCAGAGAC CATGACCACT CACCAACTGC AGAGAAATTA   1080

ATTGTGGCCT GATGTCCCTG TCCTGGAGAG GGTGGAGGTG GACCTTCACT AACCTCCTAC   1140

CTTGACCCTC TCTTTTAGGG CTCTTTCTGA CCTCCACCAT GGTACTAGGA CCCCATTGTA   1200

TTCTGTACCC TCTTGACTCT ATGACCCCCA CCGCCCACTG CATCCAGCTG GGTCCCCTCC   1260

TATCTCTATT CCCAGCTGGC CAGTGCAGTC TCAGTGCCCA CCTGTTTGTC AGTAACTCTG   1320

AAGGGGCTGA CATTTTACTG ACTTGCAAAC AAATAAGCTA ACTTTCCAGA GTTTTGTGAA   1380

TGCTGGCAGA GTCCATGAGA CTCCTGAGTC AGAGGCAAAG GCTTTTACTG CTCACAGCTT   1440

AGCAGACAGC ATGAGGTTCA TGTTCACATT AGTACACCTT GCCCCCCCCA AATCTTGTAG   1500

GGTGACCAGA GCAGTCTAGG TGGATGCTGT GCAGAAGGGG TTTGTGCCAC TGGTGAGAAA   1560

CCTGAGATTA GGAATCCTCA ATCTTATACT GGGACAACTT GCAAACCTGC TCAGCCTTTG   1620

TCTCTGATGA AGATATTATC TTCATGATCT TGGATTGAAA ACAGACCTAC TCTGGAGGAA   1680

CATATTGTAT CGATTGTCCT TGACAGTAAA CAAATCTGTT GTAAGAGACA TTATCTTTAT   1740

TATCTAGGAC AGTAAGCAAG CCTGGATCTG AGAGAGATAT CATCTTGCAA GGATGCCTGC   1800

TTTACAAACA TCCTTGAAAC AACAATCCAG AAAAAAAAAG GTGTTACTGT CTTTGCTCAG   1860

AAGACACACA GATACGTGAC AGAACCATGG AGAATTGCCT CCCAACGCTG TTCAGCCAGA   1920

GCCTTCCACC CTTTCTGCAG GACAGTCTCA ACGTTCCACC ATTAAATACT TCTTCTATCA   1980

CATCCCGCTT CTTTATGCCT AACCAAGGTT CTAGGTCCCG ATCGACTGTG TCTGGCAGCA   2040

CTCCACTGCC AAACCCAGAA TAAGGCAGCG CTCAGGATCC CGAAGGGCA TGGCTGGGA    2100

TCAGAACTTC TGGGTTTGAG TGAGGAGTGG GTCCACCCTC TTGAATTTCA AAGGAGGAAG   2160

AGGCTGGATG TGAAGGTACT GGGGGAGGGA AAGTGTCAGT TCCGAACTCT TAGGTCAATG   2220

AGGGAGGAGA CTGGTAAGGT CCCAGCTCCC GAGGTACTGA TGTGGGAATG GCCTAAGAAT   2280

CTCATATCCT CAGGAAGAAG GTGCTGGAAT CCTGAGGGGT AGAGTTCTGG GTATATTTGT   2340

GGCTTAAGGC TCTTTGGCCC CTGAAGGCAG AGGCTGGAAC CATTAGGTCC AGGGTTTGGG   2400

GTGATAGTAA TGGGATCTCT TGATTCCTCA AGAGTCTGAG GATCGAGGGT TGCCCATTCT   2460

TCCATCTTGC CACCTAATCC TTACTCCACT TGAGGGTATC ACCAGCCCTT CTAGCTCCAT   2520

GAAGGTCCCC TGGGCAAGCA CAATCTGAGC ATGAAAGATG CCCCAGAGGC CTTGGGTGTC   2580

ATCCACTCAT CATCCAGCAT CACACTCTGA GGGTGTGGCC AGCACCATGA CGTCATGTTG   2640

CTGTGACTAT CCCTGCAGCG TGCCTCTCCA GCCACCTGCC AACCGTAGAG CTGCCCATCC   2700

TCCTCTGGTG GGAGTGGCCT GCATGGTGCC AGGCTGAGGC CTAGTGTCAG ACAGGGAGCC   2760

TGGAATCATA GGGATCCAGG ACTCAAAAGT GCTAGAGAAT GGCCATATGT CACCATCCAT   2820

GAAATCTCAA GGGCTTCTGG GTGGAGGGCA CAGGGACCTG AACTTATGGT TCCCAAGTC   2880

TATTGCTCTC CAAGTGAGT CTCCCAGATA CGAGGCACTG TGCCAGCATC AGCCTTATCT   2940

CCACCACATC TTGTAAAAGG ACTACCCAGG GCCCTGATGA ACACCATGGT GTGTACAGGA   3000

GTAGGGGTG GAGGCACGGA CTCCTGTGAG GTCACAGCCA AGGGAGCATC ATCATGGGTG   3060

GGGAGGAGGC AATGGACAGG CTTGAGAACG GGGATGTGGT TGTATTTGGT TTTCTTTGGT   3120

TAGATAAAGT GCTGGGTATA GGATTGAGAG TGGAGTATGA AGACCAGTTA GGATGGAGGA   3180
```

```
TCAGATTGGA GTTGGGTTAG ATAAAGTGCT GGGTATAGGA TTGAGAGTGG AGTATGAAGA    3240

CCAGTTAGGA TGGAGGATCA GATTGGAGTT GGGTTAGAGA TGGGGTAAAA TTGTGCTCCG    3300

GATGAGTTTG GGATTGACAC TGTGGAGGTG GTTTGGGATG GCATGGCTTT GGGATGGAAA    3360

TAGATTTGTT TTGATGTTGG CTCAGACATC CTTGGGGATT GAACTGGGGA TGAAGCTGGG    3420

TTTGATTTTG GAGGTAGAAG ACGTGGAAGT AGCTGTCAGA TTTGACAGTG GCCATGAGTT    3480

TTGTTTGATG GGGAATCAAA CAATGGGGGA AGACATAAGG GTTGGCTTGT TAGGTTAAGT    3540

TGCGTTGGGT TGATGGGGTC GGGGCTGTGT ATAATGCAGT TGGATTGGTT TGTATTAAAT    3600

TGGGTTGGGT CAGGTTTTGG TTGAGGATGA GTTGAGGATA TGCTTGGGGA CACCGGATCC    3660

ATGAGGTTCT CACTGGAGTG GAGACAAACT TCCTTTCCAG GATGAATCCA GGGAAGCCTT    3720

AATTCACGTG TAGGGGAGGT CAGGCCACTG GCTAAGTATA TCCTTCCACT CCAGCTCTAA    3780

GATGGTCTTA AATTGTGATT ATCTATATCC ACTTCTGTCT CCCTCACTGT GCTTGGAGTT    3840

TACCTGATCA CTCAACTAGA AACAGGGGAA GATTTTATCA AATTCTTTTT TTTTTTTTTT    3900

TTTTTTTGAG ACAGAGTCTC ACTCTGTTGC CCAGGCTGGA GTGCAGTGGC GCAGTCTCGG    3960

CTCACTGCAA CCTCTGCCTC CCAGGTTCAA GTGATTCTCC TGCCTCAGCC TCCTGAGTTG    4020

CTGGGATTAC AGGCATGCAG CACCATGCCC AGCTAATTTT TGTATTTTTA GTAGAGATGG    4080

GGTTTCACCA ATGTTTGCCA GGCTGGCCTC GAACTCCTGA CCTGGTGATC CACCTGCCTC    4140

AGCCTCCCAA AGTGCTGGGA TTACAGGCGT CAGCCACCGC GCCCAGCCAC TTTTGTCAAA    4200

TTCTTGAGAC ACAGCTCGGG CTGGATCAAG TGAGCTACTC TGGTTTTATT GAACAGCTGA    4260

AATAACCAAC TTTTTGGAAA TTGATGAAAT CTTACGGAGT TAACAGTGGA GGTACCAGGG    4320

CTCTTAAGAG TTCCCGATTC TCTTCTGAGA CTACAAATTG TGATTTTGCA TGCCACCTTA    4380

ATCTTTTTTT TTTTTTTTTT AAATCGAGGT TTCAGTCTCA TTCTATTTCC CAGGCTGGAG    4440

TTCAATAGCG TGATCACAGC TCACTGTAGC CTTGAACTCC TGGCCTTAAG AGATTCTCCT    4500

GCTTCGGTCT CCCAATAGCT AAGACTACAG TAGTCCACCA CCATATCCAG ATAATTTTTA    4560

AATTTTTTGG GGGGCCGGGC ACAGTGGCTC ACGCCTGTAA TCCCAACACC ATGGGAGGCT    4620

GAGATGGGTG GATCACGAGG TCAGGAGTTT GAGACCAGCC TGACCAACAT GGTGAAACTC    4680

TGTCTCTACT AAAAAAAAAA AAAATAGAAA AATTAGCCGG GCGTGGTGGC ACACGGCACC    4740

TGTAATCCCA GCTACTGAGG AGGCTGAGGC AGGAGAATCA CTTGAACCCA GAAGGCAGAG    4800

GTTGCAATGA GCCGAGATTG CGCCACTGCA CTCCAGCCTG GGTGACAGAG TGAGACTCTG    4860

TCTCAAAAAA AAAAAATTTT TTTTTTTTTT TTGTAGAGAT GGATCTTGCT TTGTTTCTCT    4920

GGTTGGCCTT GAACTCCTGG CTTCAAGTGA TCCTCCTACC TTGGCCTCGG AAAGTGTTGG    4980

GATTACAGGC GTGAGCCACC ATGACTGACC TGTCGTTAAT CTTGAGGTAC ATAAACCTGG    5040

CTCCTAAAGG CTAAAGGCTA AATATTTGTT GGAGAAGGGG CATTGGATTT TGCATGAGGA    5100

TGATTCTGAC CTGGGAGGGC AGGTCAGCAG GCATCTCTGT TGCACAGATA GAGTGTACAG    5160

GTCTGGAGAA CAAGGAGTGG GGGGTTATTG GAATTCCACA TTGTTTGCTG CACGTTGGAT    5220

TTTGAAATGC TAGGGAACTT TGGGAGACTC ATATTTCTGG GCTAGAGGAT CTGTGGACCA    5280

CAAGATCTTT TTATGATGAC AGTAGCAATG TATCTGTGGA GCTGGATTCT GGGTTGGGAG    5340

TGCAAGGAAA AGAATGTACT AAATGCCAAG ACATCTATTT CAGGAGCATG AGGAATAAAA    5400

GTTCTAGTTT CTGGTCTCAG AGTGGTGCAT GGATCAGGGA GTCTCACAAT CTCCTGAGTG    5460

CTGGTGTCTT AGGGCACACT GGGTCTTGGA GTGCAAAGGA TCTAGGCACG TGAGGCTTTG    5520
```

(2) INFORMATION FOR SEQ ID NO:3:

(i) SEQUENCE CHARACTERISTICS:
        (A) LENGTH: 12047 base pairs
        (B) TYPE: nucleic acid
        (C) STRANDEDNESS: single
        (D) TOPOLOGY: linear (xi) SEQUENCE DESCRIPTION: SEQ ID NO:3:

```
TATGAAGAAT CGGGGATCGT ACCCACCCCC TGTTTCTGTT TCATCCTGGG CATGTCTCCT   5580
CTGCCTTTGT CCCCTAGATG AAGTCTCCAT GAGCTACAAG GGCCTGGTGC ATCCAGGGTG   5640
ATCTAGTAAT TGCAGAACAG CAAGTGCTAG CTCTCCCTCC CCTTCCACAG CTCTGGGTGT   5700
GGGAGGGGGT TGTCCAGCCT CCAGCAGCAT GGGGAGGGCC TTGGTCAGCC TCTGGGTGCC   5760
AGCAGGGCAG GGGCGGAGTC CTGGGGAATG AAGGTTTTAT AGGGCTCCTG GGGGAGGCTC   5820
CCCAGCCCCA AGCTT                                                   5835

GAATTCAGAA ATAGGGGAAG GTTGAGGAAG GACACTGAAC TCAAAGGGGA TACAGTGATT     60
GGTTTATTTG TCTTCTCTTC ACAACATTGG TGCTGGAGGA ATTCCCACCC TGAGGTTATG    120
AAGATGTCTG AACACCCAAC ACATAGCACT GGAGATATGA GCTCGACAAG AGTTTCTCAG    180
CCACAGAGAT TCACAGCCTA GGGCAGGAGG ACACTGTACG CCAGGCAGAA TGACATGGGA    240
ATTGCGCTCA CGATTGGCTT GAAGAAGCAA GGACTGTGGG AGGTGGGCTT TGTAGTAACA    300
AGAGGGCAGG GTGAACTCTG ATTCCCATGG GGGAATGTGA TGGTCCTGTT ACAAATTTTT    360
CAAGCTGGCA GGGAATAAAA CCCATTACGG TGAGGACCTG TGGAGGGCGG CTGCCCCAAC    420
TGATAAAGGA AATAGCCAGG TGGGGGCCTT TCCCATTGTA GGGGGGACAT ATCTGGCAAT    480
AGAAGCCTTT GAGACCCTTT AGGGTACAAG TACTGAGGCA GCAAATAAAA TGAAATCTTA    540
TTTTTCAACT TTATACTGCA TGGGTGTGAA GATATATTTG TTTCTGTACA GGGGGTGAGG    600
GAAAGGAGGG GAGGAGGAAA GTTCCTGCAG GTCTGGTTTG GTCTTGTGAT CCAGGGGGTC    660
TTGGAACTAT TTAAATTAAA TTAAATTAAA ACAAGCGACT GTTTTAAATT AAATTAAATT    720
AAATTAAATT TTACTTTATT TTATCTTAAG TTCTGGGCTA CATGTGCAGG ACGTGCAGCT    780
TTGTTACATA GGTAAACGTG TGCCATGGTG GTTTGCTGTA CCTATCAACC CATCACCTAG    840
GTATTAAGCC CAGCATGCAT TAGCTGTTTT TCCTGACGCT CTCCCTCTCC CTGACTCCCA    900
CAACAGGCCC CAGTGTGTGT TGTTCCCCTC CCTGTGTCCA TGTGTTCTCA TTGTTCAGCT    960
CCCACTTATA AGTGAGAACA TGTGGTGTTT GGTTTTCTGT TTCTGTGTTA GTTTGCTGAG   1020
GATAATGGCT TCCACCTCCA TCCATGTTCC TGCAAAGGAC GTGATCTTAT TCTTTTTTAT   1080
GGTTGCATAG AAATTGTTTT TACAAATCCA ATTGATATTG TATTTAATTA CAAGTTAATC   1140
TAATTAGCAT ACTAGAAGAG ATTACAGAAG ATATTAGGTA CATTGAATGA GGAAATATAT   1200
AAAATAGGAC GAAGGTGAAA TATTAGGTAG GAAAAGTATA ATAGTTGAAA GAAGTAAAAA   1260
AAAATATGCA TGAGTAGCAG AATGTAAAAG AGGTGAAGAA CGTAATAGTG ACTTTTTAGA   1320
CCAGATTGAA GGACAGAGAC AGAAAAATTT TAAGGAATTG CTAAACCATG TGAGTGTTAG   1380
AAGTACAGTC AATAACATTA AAGCCTCAGG AGGAGAAAAG AATAGGAAAG GAGGAAATAT   1440
GTGAATAAAT AGTAGAGACA TGTTTGATGG ATTTTAAAAT ATTTGAAAGA CCTCACATCA   1500
AAGGATTCAT ACCGTGCCAT TGAAGAGGAA GATGGAAAAG CCAAGAAGCC AGATGAAAGT   1560
TAGAAATATT ATTGGCAAAG CTTAAATGTT AAAAGTCCTA GAGAGAAAGG ATGGCAGAAA   1620
TATTGGCGGG AAAGAATGCA GAACCTAGAA TATAAATTCA TCCCAACAGT TTGGTAGTGT   1680
```

```
GCAGCTGTAG CCTTTTCTAG ATAATACACT ATTGTCATAC ATCGCTTAAG CGAGTGTAAA   1740

ATGGTCTCCT CACTTTATTT ATTTATATAT TTATTTAGTT TTGAGATGGA GCCTCGCTCT   1800

GTCTCCTAGG CTGGAGTGCA ATAGTGCGAT ACCACTCACT GCAACCTCTG CCTCCTCTGT   1860

TCAAGTGATT TTCTTACCTC AGCCTCCCGA GTAGCTGGGA TTACAGGTGC GTGCCACCAC   1920

ACCCGGCTAA TTTTTGTATT TTTTGTAGAG ACGGGGTTTT GCCATGTTGG CCAGGCTGGT   1980

CTTGAACTCC TGACATCAGG TGATCCACCT GCCTTGGCCT CCTAAAGTGC TGGGATTACA   2040

GGCATGAGCC ACCGTGCCCA ACCACTTTAT TTATTTTTTA TTTTTATTTT TAAATTTCAG   2100

CTTCTATTTG AAATACAGGG GGCACATATA TAGGATTGTT ACATGGGTAT ATTGAACTCA   2160

GGTAGTGATC ATACTACCCA ACAGGTAGGT TTTCAACCCA CTCCCCCTCT TTTCCTCCCC   2220

ATTCTAGTAG TGTGCAGTGT CTATTGTTCT CATGTTTATG TCTATGTGTG CTCCAGGTTT   2280

AGCTCCCACC TGTAAGTGAG AACGTGTGGC ATTTGATTTT CTGTCCCTGT GTTAATTCAC   2340

TTAGGATTAT GGCTTCCAGC TCCATTCATA TTGCTGTAAA GGATATGATT CATTTTTCAT   2400

GGCCATGCAG TATTCCATAT TGCGTATAGA TCACATTTTC TTTCTTTTTT TTTTTTGAGA   2460

CGGAGTCTTG CTTTGCTGCC TAGGCTGGAG TGCAGTAGCA CGATCTCGGC TCACTGCAAG   2520

CTTCACCTCC GGGGTTCACG TCATTCTTCT GTCTCAGCTT CCCAAGTAGC TGGGACTACA   2580

GGCGCCCGCC ACCACGTCCG GCTAATTTTT TTGTGTGTTT TTAGTAGAGA TGGGGGTTTC   2640

ACTGTGTTAG CCAGGATGGT CTTGATCTCC TGACCTTGTG GTCCACCTGC CTCGGTCTCC   2700

CAAAGTGCTG GGATTACAGG GGTGAGCCAC TGCGCCCGGC CCATATATAC CACATTTTCT   2760

TTAACCAATC CACCATTGAT GGGCAACTAG GTAGATTCCA TGGATTCCAC AGTTTTGCTA   2820

TTGTGTGCAG TGTGGCAGTA GACATATGAA TGAATGTGTC TTTTTGGTAT AATGATTTGC   2880

ATTCCTTTGG GTATACAGTC ATTAATAGGA GTGCTGGGTT GAACGGTGGC TCTGTTTAAA   2940

ATTCTTTGAG AATTTTCCAA ACTGTTTGCC ATAGAGAGCA AACTAATTTA CATTTCCACG   3000

AACAGTATAT AAGCATTCCC TTTTCTCCAC AGCTTTGTCA TCATGGTTTT TTTTTTTCTT   3060

TATTTTAAAA AAGAATATGT TGTTGTTTTC CCAGGGTACA TGTGCAGGAT GTGCAGGTTT   3120

GTTACATAGG TAGTAAACGT GAGCCATGGT GGTTTGCTGC ACCTGTCAAC CCATTACCTG   3180

GGTATGAAGC CCTGCCTGCA TTAGCTCTTT TCCCTAATGC TCTCACTACT GCCCCACCCT   3240

CACCCTGACA GGGCAAACAG ACAACCTACA GAATGGGAGG AAATTTTTGC AATCTATTCA   3300

TCTGACAAAG GTCAAGAATA TCCAGAATCT ACAAGGAACT TAAGCAAATT TTTACTTTTT   3360

AATAATAGCC ACTCTGACTG GCGTGAAATG GTATCTCATT GTGGTTTTCA TTTGAATTTC   3420

TCTGATGATC AGTGACGATG AGCATTTTTT CATATTTGTT GGCTGCTTGT ACGTCTTTTG   3480

AGAAGTGTCT CTTCATGCCT TTTGGCCACT TTAATGGGAT TATTTTTTGC TTTTTAGTTT   3540

AAGTTCCTTA TAGATTCTGG ATATTAGACT TCTTATTGGA TGCATAGTTT GTGAATACTC   3600

TCTTCCATTC TGTAGGTTGT CTGTTTACTC TATTGATGGC TTCTTTTGCT GTGCCGAAGC   3660

ATCTTAGTTT AATTAGAAAC CACCTGCCAA TTTTTGTTTT TGTTGCAATT GCTTTTGGGG   3720

ACTTAGTCAT AAACTCTTTG CCAAGGTCTG GGTCAAGAAG AGTATTTCCT AGGTTTTCTT   3780

CTAGAATTTT GAAAGTCTGA ATGTAAACAT TTGCATTTTT AATGCATCTT GAGTTAGTTT   3840

TTGTATATGT GAAAGGTCTA CTCTCATTTT CTTTCCCTCT TCTTTCTTT  CTTTCTTTTC   3900

TTTCTTTCTT TCTTTCTTTC TTTCTTTCTT TCTTTCTTTC TTTCTTTTTG TCCTTCTTTC   3960

TTTCTTTCTT TCTCTTTCTT TCTCTCTTTC TTTTTTTTTT TTGATGGAGT ATTGCTCTGT   4020

TGCCCAGGCT GCAGTGCAGC GGCACGATCT CGGCTCACTG CAACCTCTGC CTCCTGGGTT   4080
```

```
CAACTGATTC TCCTGCATCA GCCTTCCAAG TAGCTGGGAT TATAGGCGCC CGCCACCACG    4140

CCCGACTAAT TTTTGTATTT TTAGTAGAGA CGGGGTTGTG CCATGTTGGC CAGGCTGGTT    4200

TGAAACTCCT GACCTCAAAC GATCTGCCTG CCTTGGCCTC CCAAAGTGCT GGGATTACAG    4260

GTGTGAGCCA CTGTGCCCAG CCAAGAATGT CATTTTCTAA GAGGTCCAAG AACCTCAAGA    4320

TATTTTGGGA CCTTGAGAAG AGAGGAATTC ATACAGGTAT TACAAGCACA GCCTAATGGC    4380

AAATCTTTGG CATGGCTTGG CTTCAAGACT TTAGGCTCTT AAAAGTCGAA TCCAAAAATT    4440

TTTATAAAAG CTCCAGCTAA GCTACCTTAA AAGGGGCCTG TATGGCTGAT CACTCTTCTT    4500

GCTATACTTT ACACAAATAA ACAGGCCAAA TATAATGAGG CCAAAATTTA TTTTGCAAAT    4560

AAATTGGTCC TGCTATGATT TACTCTTGGT AAGAACAGGG AAAATAGAGA AAAATTTAGA    4620

TTGCATCTGA CCTTTTTTTC TGAATTTTTA TATGTGCCTA CAATTTGAGC TAAATCCTGA    4680

ATTATTTTCT GGTTGCAAAA ACTCTCTAAA GAAGAACTTG GTTTTCATTG TCTTCGTGAC    4740

ACATTTATCT GGCTCTTTAC TAGAACAGCT TTCTTGTTTT TGGTGTTCTA GCTTGTGTGC    4800

CTTACAGTTC TACTCTTCAA ATTATTGTTA TGTGTATCTC ATAGTTTTCC TTCTTTTGAG    4860

AAAACTGAAG CCATGGTATT CTGAGGACTA GAGATGACTC AACAGAGCTG GTGAATCTCC    4920

TCATATGCAA TCCACTGGGC TCGATCTGCT TCAAATTGCT GATGCACTGC TGCTAAAGCT    4980

ATACATTTAA AACCCTCACT AAAGGATCAG GGACCATCAT GGAAGAGGAG GAAACATGAA    5040

ATTGTAAGAG CCAGATTCGG GGGGTAGAGT GTGGAGGTCA GAGCAACTCC ACCTTGAATA    5100

AGAAGGTAAA GCAACCTATC CTGAAAGCTA ACCTGCCATG GTGGCTTCTG ATTAACCTCT    5160

GTTCTAGGAA GACTGACAGT TTGGGTCTGT GTCATTGCCC AAATCTCATG TTAAATTGTA    5220

ATCCCCAGTG TTCGGAGGTG GGACTTGGTG GTAGGTGATT CGGTCATGGG AGTAGATTTT    5280

CTTCTTTGTG GTGTTACAGT GATAGTGAGT GAGTTCTCGT GAGATCTGGT CATTTAAAAG    5340

TGTGTGGCCC CTCCCCTCCC TCTCTTGGTC CTCCTACTGC CATGTAAGAT ACCTGCTCCT    5400

GCTTTGCCTT CTACCATAAG TAAAAGCCCC CTGAGGCCTC CCCAGAAGCA GATGCCACCA    5460

TGCTTCCTGT ACAGCCTGCA GAACCATCAG CCAATTAAAC CTCTTTTCTG TATAAATTAC    5520

CAGTCTTGAG TATCTCTTTA CAGCAGTGTG AGAACGGACT AATACAAGGG TCTCCAAAAT    5580

TCCAAGTTTA TGTATTCTTT CTTGCCAAAT AGCAGGTATT TACCATAAAT CCTGTCCTTA    5640

GGTCAAACAA CCTTGATGGC ATCGTACTTC AATTGTCTTA CACATTCCTT CTGAATGACT    5700

CCTCCCCTAT GGCATATAAG CCCTGGGTCT TGGGGATAAT GGCAGAGGG GTCCACCATC    5760

TTGTCTGGCT GCCACCTGAG ACACGGACAT GGCTTCTGTT GGTAAGTCTC TATTAAATGT    5820

TTCTTTCTAA GAAACTGGAT TTGTCAGCTT GTTTCTTTGG CCTCTCAGCT TCCTCAGACT    5880

TTGGGGTAGG TTGCACAACC CTGCCCACCA CGAAACAAAT GTTTAATATG ATAAATATGG    5940

ATAGATATAA TCCACATAAA TAAAAGCTCT TGGAGGGCCC TCAATAATTG TTAAGAGTGT    6000

AAATGTGTCC AAAGATGGAA AATGTTTGAG AACTACTGTC CCAGAGATTT TCCTGAGTTC    6060

TAGAGTGTGG GAATATAGAA CCTGGAGCTT GGCTTCTTCA GCCTAGAATC AGGAGTATGG    6120

GGCTGAAGTC TGAAGCTTGG CTTCAGCAGT TTGGGGTTGG CTTCCGGAGC ACATATTTGA    6180

CATGTTGCGA CTGTGATTTG GGGTTTGGTA TTTGCTCTGA ATCCTAATGT CTGTCCTTGA    6240

GGCATCTAGA ATCTGAAATC TGTGGTCAGA ATTCTATTAT CTTGAGTAGG ACATCTCCAG    6300

TCCTGGTTCT GCCTTCTAGG GCTGGAGTCT GTAGTCAGTG ACCCGGTCTG GCATTTCAAC    6360

TTCATATACA GTGGGCTATC TTTTGGTCCA TGTTTCAACC AAACAACCGA ATAAACCATT    6420
```

-continued

```
AGAACCTTTC CCCACTTCCC TAGCTGCAAT GTTAAACCTA GGATTTCTGT TTAATAGGTT    6480

CATATGAATA ATTTCAGCCT GATCCAACTT TACATTCCTT CTACCGTTAT TCTACACCCA    6540

CCTTAAAAAT GCATTCCCAA TATATTCCCT GGATTCTACC TATATATGGT AATCCTGGCT    6600

TTGCCAGTTT CTAGTGCATT AACATACCTG ATTTACATTC TTTTACTTTA AAGTGGAAAT    6660

AAGAGTCCCT CTGCAGAGTT CAGGAGTTCT CAAGATGGCC CTTACTTCTG ACATCAATTG    6720

AGATTTCAAG GGAGTCGCCA AGATCATCCT CAGGTTCAGT GATTGCTGGT AGCCCTCATA    6780

TAACTCAATG AAAGCTGTTA TGCTCATGGC TATGGTTTAT TACAGCAAAA GAATAGAGAT    6840

GAAAATCTAG CAAGGGAAGA GTTGCATGGG GCAAAGACAA GGAGAGCTCC AAGTGCAGAG    6900

ATTCCTGTTG TTTTCTCCCA GTGGTGTCAT GGAAAGCAGT ATCTTCTCCA TACAATGATG    6960

TGTGATAATA TTCAGTGTAT TGCCAATCAG GAACTCAAC TGAGCCTTGA TTATATTGGA     7020

GCTTGGTTGC ACAGACATGT CGACCACCTT CATGGCTGAA CTTTAGTACT TAGCCCCTCC    7080

AGACGTCTAC AGCTGATAGG CTGTAACCCA ACATTGTCAC CATAAATCAC ATTGTTAGAC    7140

TATCCAGTGT GGCCCAAGCT CCCGTGTAAA CACAGGCACT CTAAACAGGC AGGATATTTC    7200

AAAAGCTTAG AGATGACCTC CCAGGAGCTG AATGCAAAGA CCTGGCCTCT TTGGGCAAGG    7260

AGAATCCTTT ACCGCACACT CTCCTTCACA GGGTTATTGT GAGGATCAAA TGTGGTCATG    7320

TGTGTGAGAC ACCAGCACAT GTCTGGCTGT GGAGAGTGAC TTCTATGTGT GCTAACATTG    7380

CTGAGTGCTA AGAAAGTATT AGGCATGGCT TTCAGCACTC ACAGATGCTC ATCTAATCCT    7440

CACAACATGG CTACAGGGTG GGCACTACTA GCCTCATTTG ACAGAGGAAA GGACTGTGGA    7500

TAAGAAGGGG GTGACCAATA GGTCAGAGTC ATTCTGGATG CAAGGGGCTC CAGAGGACCA    7560

TGATTAGACA TTGTCTGCAG AGAAATTATG GCTGGATGTC TCTGCCCCGG AAAGGGGGAT    7620

GCACTTTCCT TGACCCCCTA TCTCAGATCT TGACTTTGAG GTTATCTCAG ACTTCCTCTA    7680

TGATACCAGG AGCCCATCAT AATCTCTCTG TGTCCTCTCC CCTTCCTCAG TCTTACTGCC    7740

CACTCTTCCC AGCTCCATCT CCAGCTGGCC AGGTGTAGCC ACAGTACCTA ACTCTTTGCA    7800

GAGAACTATA AATGTGTATC CTACAGGGGA GAAAAAAAA AAGAACTCTG AAAGAGCTGA     7860

CATTTTACCG ACTTGCAAAC ACATAAGCTA ACCTGCCAGT TTTGTGCTGG TAGAACTCAT    7920

GAGACTCCTG GGTCAGAGGC AAAAGATTTT ATTACCCACA GCTAAGGAGG CAGCATGAAC    7980

TTTGTGTTCA CATTTGTTCA CTTTGCCCCC CAATTCATAT GGGATGATCA GAGCAGTTCA    8040

GGTGGATGGA CACAGGGGTT TGTGGCAAAG GTGAGCAACC TAGGCTTAGA AATCCTCAAT    8100

CTTATAAGAA GGTACTAGCA AACTTGTCCA GTCTTTGTAT CTGACGGAGA TATTATCTTT    8160

ATAATTGGGT TGAAAGCAGA CCTACTCTGG AGGAACATAT TGTATTTATT GTCCTGAACA    8220

GTAAACAAAT CTGCTGTAAA ATAGACGTTA ACTTTATTAT CTAAGGCAGT AAGCAAACCT    8280

AGATCTGAAG GCGATACCAT CTTGCAAGGC TATCTGCTGT ACAAATATGC TTGAAAAGAT    8340

GGTCCAGAAA AGAAAACGGT ATTATTGCCT TTGCTCAGAA GACACACAGA AACATAAGAG    8400

AACCATGGAA AATTGTCTCC CAACACTGTT CACCCAGAGC CTTCCACTCT TGTCTGCAGG    8460

ACAGTCTTAA CATCCCATCA TTAGTGTGTC TACCACATCT GGCTTCACCG TGCCTAACCA    8520

AGATTTCTAG GTCCAGTTCC CCACCATGTT TGGCAGTGCC CCACTGCCAA CCCCAGAATA    8580

AGGGAGTGCT CAGAATTCCG AGGGGACATG GGTGGGATC AGAACTTCTG GGCTTGAGTG      8640

CAGAGGGGC CCATACTCCT TGGTTCCGAA GGAGGAAGAG GCTGGAGGTG AATGTCCTTG      8700

GAGGGGAGGA ATGTGGGTTC TGAACTCTTA AATCCCCAAG GGAGGAGACT GGTAAGGTCC    8760

CAGCTTCCGA GGTACTGACG TGGGAATGGC CTGAGAGGTC TAAGAATCCC GTATCCTCGG    8820
```

```
GAAGGAGGGG CTGAAATTGT GAGGGGTTGA GTTGCAGGGG TTTGTTAGCT TGAGACTCCT   8880
TGGTGGGTCC CTGGGAAGCA AGGACTGGAA CCATTGGCTC CAGGGTTTGG TGTGAAGGTA   8940
ATGGGATCTC CTGATTCTCA AAGGGTCAGA GGACTGAGAG TTGCCCATGC TTTGATCTTT   9000
CCATCTACTC CTTACTCCAC TTGAGGGTAA TCACCTACTC TTCTAGTTCC ACAAGAGTGC   9060
GCCTGCGCGA GTATAATCTG CACATGTGCC ATGTCCCGAG GCCTGGGGCA TCATCCACTC   9120
ATCATTCAGC ATCTGCGCTA TGCGGGCGAG GCCGGCGCCA TGACGTCATG TAGCTGCGAC   9180
TATCCCTGCA GCGCGCCTCT CCCGTCACGT CCCAACCATG GAGCTGTGGA CGTGCGTCCC   9240
CTGGTGGATG TGGCCTGCGT GGTGCCAGGC CGGGGCCTGG TGTCCGATAA AGATCCTAGA   9300
ACCACAGGAA ACCAGGACTG AAAGGTGCTA GAGAATGGCC ATATGTCGCT GTCCATGAAA   9360
TCTCAAGGAC TTCTGGGTGG AGGGCACAGG AGCCTGAACT TACGGGTTTG CCCCAGTCCA   9420
CTGTCCTCCC AAGTGAGTCT CCCAGATACG AGGCACTGTG CCAGCATCAG CTTCATCTGT   9480
ACCACATCTT GTAACAGGGA CTACCCAGGA CCCTGATGAA CACCATGGTG TGTGCAGGAA   9540
GAGGGGTGA AGGCATGGAC TCCTGTGTGG TCAGAGCCCA GAGGGGCCA TGACGGGTGG    9600
GGAGGAGGCT GTGGACTGGC TCGAGAAGTG GGATGTGGTT GTGTTTGATT TCCTTTGGCC   9660
AGATAAAGTG CTGGATATAG CATTGAAAAC GGAGTATGAA GACCAGTTAG AATGGAGGGT   9720
CAGGTTGGAG TTGAGTTACA GATGGGTAA AATTCTGCTT CGGATGAGTT TGGGGATTGG    9780
CAATCTAAAG GTGGTTTGGG ATGGCATGGC TTTGGGATGG AAATAGGTTT GTTTTTATGT   9840
TGGCTGGGAA GGGTGTGGGG ATTGAATTGG GGATGAAGTA GGTTTAGTTT TGGAGATAGA   9900
ATACATGGAG CTGGCTATTG CATGCGAGGA TGTGCATTAG TTTGGTTTGA TCTTTAAATA   9960
AAGGAGGCTA TTAGGGTTGT CTTGAATTAG ATTAAGTTGT GTTGGGTTGA TGGGTTGGGC  10020
TTGTGGGTGA TGTGGTTGGA TTGGGCTGTG TTAAATTGGT TTGGGTCAGG TTTTGGTTGA  10080
GGTTATCATG GGGATGAGGA TATGCTTGGG ACATGGATTC AGGTGGTTCT CATTCAAGCT  10140
GAGGCAAATT TCCTTTCAGA CGGTCATTCC AGGGAACGAG TGGTTGTGTG GGGGAAATCA  10200
GGCCACTGGC TGTGAATATC CCTCTATCCT GGTCTTGAAT TGTGATTATC TATGTCCATT  10260
CTGTCTCCTT CACTGTACTT GGAATTGATC TGGTCATTCA GCTGGAAATG GGGGAAGATT  10320
TTGTCAAATT CTTGAGACAC AGCTGGGTCT GGATCAGCGT AAGCCTTCCT TCTGGTTTTA  10380
TTGAACAGAT GAAATACACAT TTTTTTTTTC AAAATCACAG AAATCTTATA GAGTTAACAG  10440
TGGACTCTTA TAATAAGAGT TAACACCAGG ACTCTTATTC TTGATTCTTT TCTGAGACAC  10500
CAAAATGAGA TTTCTCAATG CCACCCTAAT TCTTTTTTTT TTTTTTTTT TTTTTGAGAC   10560
ACAGTCTGGG TCTTTTGCTC TGTCACTCAG GCTGGAGCGC AGTGGTGTGA TCATAGCTCA  10620
CTGAACCCTT GACCTCCTGG ACTTAAGGGA TCCTCCTGCT TCAGCCTCCT GAGTAGATGG  10680
GGCTACAGGT GCTTGCCACC ACACCTGGCT AATTAAATTT TTTTTTTTT TTTGTAGAGA   10740
AAGGGTCTCA CTTTGTTGCC CTGGCTGATC TTGAACTTCT GACTTCAAGT GATTCTTCAG  10800
CCTTGGACTC CCAAAGCACT GGGATTGCTG GCATGAGCCA CTCACCGTGC CTGGCTTGCA  10860
GCTTAATCTT GGAGTGTATA AACCTGGCTC CTGATAGCTA GACATTTCAG TGAGAAGGAG  10920
GCATTGGATT TTGCATGAGG ACAATTCTGA CCTAGGAGGG CAGGTCAACA GGAATCCCCG  10980
CTGTACCTGT ACGTTGTACA GGCATGGAGA ATGAGGAGTG AGGAGGCCGT ACCGGAACCC  11040
CATATTGTTT AGTGGACATT GGATTTTGAA ATAATAGGGA ACTTGGTCTG GGAGAGTCAT  11100
ATTTCTGGAT TGGACAATAT GTGGTATCAC AAGGTTTTAT GATGAGGGAG AAATGTATGT  11160
```

```
GGGGAACCAT TTTCTGAGTG TGGAAGTGCA AGAATCAGAG AGTAGCTGAA TGCCAACGCT  11220

TCTATTTCAG GAACATGGTA AGTTGGAGGT CCAGCTCTCG GGCTCAGACG GGTATAGGGA  11280

CCAGGAAGTC TCACAATCCG ATCATTCTGA TATTTCAGGG CATATTAGGT TTGGGGTGCA  11340

AAGGAAGTAC TTGGGACTTA GGCACATGAG ACTTTGTATT GAAAATCAAT GATTGGGGCT  11400

GGCCGTGGTG CTCACGCCTG TAATCTCATC ACTTTGGGAG ACCGAAGTGG GAGGATGGCT  11460

TGATCTCAAG AGTTGGACAC CAGCCTAGGC AACATGGCCA GACCCTCTCT CTACAAAAAA  11520

ATTAAAAATT AGCTGGATGT GGTGGTGCAT GCTTGTGGTC TCAGCTATCC TGGAGGCTGA  11580

GACAGGAGAA TCGGTTGAGT CTGGGAGTTC AAGGCTACAG GGAGCTGCGA TCACGCCGCT  11640

GCACTCCAGC CTGGGAAACA GAGTGAGACT GTCTCAGAAT TTTTTTAAAA AGAATCAGT  11700

GATCATCCCA ACCCCTGTTG CTGTTCATCC TGAGCCTGCC TTCTCTGGCT TTGTTCCCTA  11760

GATCACATCT CCATGATCCA TAGGCCCTGC CCAATCTGAC CTCACACCGT GGGAATGCCT  11820

CCAGACTGAT CTAGTATGTG TGGAACAGCA AGTGCTGGCT CTCCCTCCCC TTCCACAGCT  11880

CTGGGTGTGG GAGGGGGTTG TCCAGCCTCC AGCAGCATGG GGAGGGCCTT GGTCAGCATC  11940

TAGGTGCCAA CAGGGCAAGG GCGGGGTCCT GGAGAATGAA GGCTTTATAG GGCTCCTCAG  12000

GGAGGCCCCC CAGCCCCAAA CTGCACCACC TGGCCGTGGA CACCGGT                12047

(2) INFORMATION FOR SEQ ID NO:4:

(i) SEQUENCE CHARACTERISTICS:
        (A) LENGTH: 454 base pairs
        (B) TYPE: nucleic acid
        (C) STRANDEDNESS: single
        (D) TOPOLOGY: linear (xi) SEQUENCE DESCRIPTION: SEQ ID NO:4:

AAGCTTCCAC AAGTGCATTT AGCCTCTCCA GTATTGCTGA TGAATCCACA GTTCAGGTTC    60

AATGGCGTTC AAAACTTGAT CAAAAATGAC CAGACTTTAT ATTCTTACAC CAACATCTAT   120

CTGATTGGAG GAATGGATAA TAGTCATCAT GTTTAAACAT CTACCATTCC AGTTAAGAAA   180

ATATGATAGC ATCTTGTTCT TAGTCTTTTT CTTAATAGGG ACATAAAGCC CACAAATAAA   240

AATATGCCTG AAGAATGGGA CAGGCATTGG GCATTGTCCA TGCCTAGTAA AGTACTCCAA   300

GAACCTATTT GTATACTAGA TGACACAATG TCAATGTCTG TGTACAACTG CCAACTGGGA   360

TGCAAGACAC TGCCCATGCC AATCATCCTG AAAAGCAGCT ATAAAAAGCA GGAAGCTACT   420

CTGCACCTTG TCAGTGAGGT CCAGATACCT ACAG                               454

(2) INFORMATION FOR SEQ ID NO:5:

(i) SEQUENCE CHARACTERISTICS:
        (A) LENGTH: 5224 base pairs
        (B) TYPE: nucleic acid
        (C) STRANDEDNESS: single
        (D) TOPOLOGY: linear (xi) SEQUENCE DESCRIPTION: SEQ ID NO:5:

GAATTCTTAG AAATATGGGG GTAGGGGTGG TGGTGGTAAT TCTGTTTTCA CCCCATAGGT    60

GAGATAAGCA TTGGGTTAAA TGTGCTTTCA CACACACATC ACATTTCATA AGAATTAAGG   120

AACAGACTAT GGGCTGGAGG ACTTTGAGGA TGTCTGTCTC ATAACACTTG GGTTGTATCT   180

GTTCTATGGG GCTTGTTTTA AGCTTGGCAA CTTGCAACAG GGTTCACTGA CTTTCTCCCC   240

AAGCCCAAGG TACTGTCCTC TTTTCATATC TGTTTTGGGG CCTCTGGGGC TTGAATATCT   300

GAGAAAATAT AAACATTTCA ATAATGTTCT GTGGTGAGAT GAGTATGAGA GATGTGTCAT   360
```

```
TCATTTGTAT CAATGAATGA ATGAGGACAA TTAGTGTATA AATCCTTAGT ACAACAATCT    420

GAGGGTAGGG GTGGTACTAT TCAATTTCTA TTTATAAAGA TACTTATTTC TATTTATTTA    480

TGCTTGTGAC AAATGTTTTG TTCGGGACCA CAGGAATCAC AAAGATGAGT CTTTGAATTT    540

AAGAAGTTAA TGGTCCAGGA ATAATTACAT AGCTTACAAA TGACTATGAT ATACCATCAA    600

ACAAGAGGTT CCATGAGAAA ATAATCTGAA AGGTTTAATA AGTTGTCAAA GGTGAGAGGG    660

CTCTTCTCTA GCTAGAGACT AATCAGAAAT ACATTCAGGG ATAATTATTT GAATAGACCT    720

TAAGGGTTGG GTACATTTTG TTCAAGCATT GATGGAGAAG GAGAGTGAAT ATTTGAAAAC    780

ATTTTCAACT AACCAACCAC CCAATCCAAC AAACAAAAAA TGAAAAGAAT CTCAGAAACA    840

GTGAGATAAG AGAAGGAATT TTCTCACAAC CCACACGTAT AGCTCAACTG CTCTGAAGAA    900

GTATATATCT AATATTTAAC ACTAACATCA TGCTAATAAT GATAATAATT ACTGTCATTT    960

TTTAATGTCT ATAAGTACCA GGCATTTAGA AGATATTATT CCATTTATAT ATCAAAATAA   1020

ACTTGAGGGG ATAGATCATT TTCATGATAT ATGAGAAAAA TTAAAAACAG ATTGAATTAT   1080

TTGCCTGTCA TACAGCTAAT AATTGACCAT AAGACAATTA GATTTAAATT AGTTTTGAAT   1140

CTTTCTAATA CCAAAGTTCA GTTTACTGTT CCATGTTGCT TCTGAGTGGC TTCACAGACT   1200

TATGAAAAAG TAAACGGAAT CAGAATTACA TCAATGCAAA AGCATTGCTG TGAACTCTGT   1260

ACTTAGGACT AAACTTTGAG CAATAACACA CATAGATTGA GGATTGTTTG CTGTTAGCAT   1320

ACAAACTCTG GTTCAAAGCT CCTCTTTATT GCTTGTCTTG GAAAATTTGC TGTTCTTCAT   1380

GGTTTCTCTT TTCACTGCTA TCTATTTTTC TCAACCACTC ACATGGCTAC AATAACTGTC   1440

TGCAAGCTTA TGATTCCCAA ATATCTATCT CTAGCCTCAA TCTTGTTCCA GAAGATAAAA   1500

AGTAGTATTC AAATGCACAT CAACGTCTCC ACTTGGAGGG CTTAAAGACG TTTCAACATA   1560

CAAACCGGGG AGTTTTGCCT GGAATGTTTC CTAAAATGTG TCCTGTAGCA CATAGGGTCC   1620

TCTTGTTCCT TAAAATCTAA TTACTTTTAG CCCAGTGCTC ATCCCACCTA TGGGGAGATG   1680

AGAGTGAAAA GGGAGCCTGA TTAATAATTA CACTAAGTCA ATAGGCATAG AGCCAGGACT   1740

GTTTGGGTAA ACTGGTCACT TTATCTTAAA CTAAATATAT CCAAAACTGA ACATGTACTT   1800

AGTTACTAAG TCTTTGACTT TATCTCATTC ATACCACTCA GCTTTATCCA GGCCACTTAT   1860

TTGACAGTAT TATTGCGAAA ACTTCCTAAC TGGTCTCCTT ATCATAGTCT TATCCCCTTT   1920

TGAAACAAAA GAGACAGTTT CAAAATACAA ATATGATTTT TATTAGCTCC CTTTTGTTGT   1980

CTATAATAGT CCCAGAAGGA GTTATAAACT CCATTTAAAA AGTCTTTGAG ATGTGGCCCT   2040

TGCCAACTTT GCCAGGAATT CCCAATATCT AGTATTTTCT ACTATTAAAC TTTGTGCCTC   2100

TTCAAAACTG CATTTTCTCT CATTCCCTAA GTGTGCATTG TTTTCCCTTA CCGGTTGGTT   2160

TTTCCACCAC CTTTTACATT TTCCTGGAAC ACTATACCCT CCCTCTTCAT TTGGCCCACC   2220

TCTAATTTTC TTTCAGATCT CCATGAAGAT GTTACTTCCT CCAGGAAGCC TTATCTGACC   2280

CCTCCAAAGA TGTCATGAGT TCCTCTTTTC ATTCTACTAA TCACAGCATC CATCACACCA   2340

TGTTGTGATT ACTGATACTA TTGTCTGTTT CTCTGATTAG GCAGTAAGCT CAACAAGAGC   2400

TACATGGTGC CTGTCTCTTG TTGCTGATTA TTCCCATCCA AAAACAGTGC CTGGAATGCA   2460

GACTTAACAT TTTATTGAAT GAATAAATAA AACCCCATCT ATCGAGTGCT ACTTTGTGCA   2520

AGACCCGGTT CTGAGGCATT TATATTTATT GATTTATTTA ATTCTCATTT AACCATGAAG   2580

GAGGTACTAT CACTATCCTT ATTTTATAGT TGATAAAGAT AAAGCCCAGA GAAATGAATT   2640

AACTCACCCA AAGTCATGTA GCTAAGTGAC AGGGCAAAAA TTCAAACCAG TTCCCCAACT   2700
```

-continued

```
TTACGTGATT AATACTGTGC TATACTGCCT CTCTGATCAT ATGGCATGGA ATGCAGACAT    2760

CTGCTCCGTA AGGCAGAATA TGGAAGGAGA TTGGAGGATG ACACAAAACC AGCATAATAT    2820

CAGAGGAAAA GTCCAAACAG GACCTGAACT GATAGAAAAG TTGTTACTCC TGGTGTAGTC    2880

GCATCGACAT CTTGATGAAC TGGTGGCTGA CACAACATAC ATTGGCTTGA TGTGTACATA    2940

TTATTTGTAG TTGTGTGTGT ATTTTTATAT ATATATTTGT AATATTGAAA TAGTCATAAT    3000

TTACTAAAGG CCTACCATTT GCCAGGCATT TTTACATTTG TCCCCTCTAA TCTTTTGATG    3060

AGATGATCAG ATTGGATTAC TTGGCCTTGA AGATGATATA TCTACATCTA TATCTATATC    3120

TATATCTATA TCTATATCTA TATCTATATC TATATCTATA TATGTATATC AGAAAAGCTG    3180

AAATATGTTT TGTAAAGTTA TAAAGATTTC AGACTTTATA GAATCTGGGA TTTGCCAAAT    3240

GTAACCCCTT TCTCTACATT AAACCCATGT TGGAACAAAT ACATTTATTA TTCATTCATC    3300

AAATGTTGCT GAGTCCTGGC TATGAACCAG ACACTGTGAA AGCCTTTGGG ATATTTTGCC    3360

CATGCTTGGG CAAGCTTATA TAGTTTGCTT CATAAAACTC TATTTCAGTT CTTCATAACT    3420

AATACTTCAT GACTATTGCT TTTCAGGTAT TCCTTCATAA CAAATACTTT GGCTTTCATA    3480

TATTTGAGTA AAGTCCCCCT TGAGGAAGAG TAGAAGAACT GCACTTTGTA AATACTATCC    3540

TGGAATCCAA ACGGATAGAC AAGGATGGTG CTACCTCTTT CTGGAGAGTA CGTGAGCAAG    3600

GCCTGTTTTG TTAACATGTT CCTTAGGAGA CAAAACTTAG GAGAGACACG CATAGCAGAA    3660

AATGGACAAA AACTAACAAA TGAATGGGAA TTGTACTTGA TTAGCATTGA AGACCTTGTT    3720

TATACTATGA TAAATGTTTG TATTTGCTGG AAGTGCTACT GACGGTAAAC CCTTTTTGTT    3780

TAAATGTGTG CCCTAGTAGC TTGCAGTATG ATCTATTTTT TAAGTACTGT ACTTAGCTTA    3840

TTTAAAAATT TTATGTTTAA AATTGCATAG TGCTCTTTCA TTGAAGAAGT TTTGAGAGAG    3900

AGATAGAATT AAATTCACTT ATCTTACCAT CTAGAGAAAC CCAATGTTAA AACTTTGTTG    3960

TCCATTATTT CTGTCTTTTA TTCAACATTT TTTTTAGAGG GTGGGAGGAA TACAGAGGAG    4020

GTACAATGAT ACACAAATGA GAGCACTCTC CATGTATTGT TTTGTCCTGT TTTTCAGTTA    4080

ACAATATATT ATGAGCATAT TTCCATTTCA TTAAATATTC TTCCACAAAG TTATTTTGAT    4140

GGCTGTATAT CACCCTACTT TATGAATGTA CCATATTAAT TTATTTCCTG GTGTGGGTTA    4200

TTTGATTTTA TAATCTTACC TTTAGAATAA TGAACACCCT GTGAAGCTTT AGAAAATACT    4260

GGTGCCTGGG TCTCAACTCC ACAGATTCTG ATTTAACTGG TCTGGGTTAC AGACTAGGCA    4320

TTGGGAATTC AAAAAGTTCC CCCAGTGATT CTAATGTGTA GCCAAGATCG GGAACCCTTG    4380

TAGACAGGGA TGATAGGAGG TGAGCCACTC TTAGCATCCA TCATTTAGTA TTAACATCAT    4440

CATCTTGAGT TGCTAAGTGA ATGATGCACC TGACCCACTT TATAAAGACA CATGTGCAAA    4500

TAAAATTATT ATAGGACTTG GTTTATTAGG GCTTGTGCTC TAAGTTTTCT ATGTTAAGCC    4560

ATACATCGCA TACTAAATAC TTTAAAATGT ACCTTATTGA CATACATATT AAGTGAAAAG    4620

TGTTTCTGAG CTAAACAATG ACAGCATAAT TATCAAGCAA TGATAATTTG AAATGAATTT    4680

ATTATTCTGC AACTTAGGGA CAAGTCATCT CTCTGAATTT TTTGTACTTT GAGAGTATTT    4740

GTTATATTTG CAAGATGAAG AGTCTGAATT GGTCAGACAA TGTCTTGTGT GCCTGGCATA    4800

TGATAGGCAT TTAATAGTTT TAAAGAATTA ATGTATTTAG ATGAATTGCA TACCAAATCT    4860

GCTGTCTTTT CTTTATGGCT TCATTAACTT AATTTGAGAG AAATTAATTA TTCTGCAACT    4920

TAGGGACAAG TCATGTCTTT GAATATTCTG TAGTTTGAGG AGAATATTTG TTATATTTGC    4980

AAAATAAAAT AAGTTTGCAA GTTTTTTTTT TCTGCCCCAA AGAGCTCTGT GTCCTTGAAC    5040

ATAAAATACA AATAACCGCT ATGCTGTTAA TTATTGGCAA ATGTCCCATT TCAACCTAA     5100
```

```
GGAAATACCA TAAAGTAACA GATATACCAA CAAAAGGTTA CTAGTTAACA GGCATTGCCT    5160

GAAAAGAGTA TAAAAGAATT TCAGCATGAT TTTCCATATT GTGCTTCCAC CACTGCCAAT    5220

AACA                                                                 5224

(2) INFORMATION FOR SEQ ID NO:6:

(i) SEQUENCE CHARACTERISTICS:
        (A) LENGTH: 822 base pairs
        (B) TYPE: nucleic acid
        (C) STRANDEDNESS: single
        (D) TOPOLOGY: linear (xi) SEQUENCE DESCRIPTION: SEQ ID NO:6:

GCATTGCTGT GAACTCTGTA CTTAGGACTA AACTTTGAGC AATAACACAC ATAGATTGAG      60

GATTGTTTGC TGTTAGCATA CAAACTCTGG TTCAAAGCTC CTCTTTATTG CTTGTCTTGG    120

AAAATTTGCT GTTCTTCATG GTTTCTCTTT TCACTGCTAT CTATTTTTCT CAACCACTCA    180

CATGGCTACA ATAACTGTCT GCAAGCTTAT GATTCCCAAA TATCTATCTC TAGCCTCAAT    240

CTTGTTCCAG AAGATAAAAA GTAGTATTCA AATGCACATC AACGTCTCCA CTTGGAGGGC    300

TTAAAGACGT TTCAACATAC AAACCGGGGA GTTTTGCCTG GAATGTTTCC TAAAATGTGT    360

CCTGTAGCAC ATAGGGTCCT CTTGTTCCTT AAAATCTAAT TACTTTTAGC CCAGTGCTCA    420

TCCCACCTAT GGGGAGATGA GAGTGAAAAG GGAGCCTGAT TAATAATTAC ACTAAGTCAA    480

TAGGCATAGA GCCAGGACTG TTTGGGTAAA CTGGTCACTT TATCTTAAAC TAAATATATC    540

CAAAACTGAA CATGTACTTA GTTACTAAGT CTTTGACTTT ATCTCATTCA TACCACTCAG    600

CTTTATCCAG GCCACTTATG AGCTCTGTGT CCTTGAACAT AAAATACAAA TAACCGCTAT    660

GCTGTTAATT ATTGGCAAAT GTCCCATTTT CAACCTAAGG AAATACCATA AAGTAACAGA    720

TATACCAACA AAAGGTTACT AGTTAACAGG CATTGCCTGA AAAGAGTATA AAGAATTTC     780

AGCATGATTT TCCATATTGT GCTTCCACCA CTGCCAATAA CA                       822

(2) INFORMATION FOR SEQ ID NO:7:

(i) SEQUENCE CHARACTERISTICS:
        (A) LENGTH: 472 base pairs
        (B) TYPE: nucleic acid
        (C) STRANDEDNESS: single
        (D) TOPOLOGY: linear (xi) SEQUENCE DESCRIPTION: SEQ ID NO:7:

AGCCACCACC CAGTGAGCCT TTTTCTAGCC CCCAGAGCCA CCTCTGTCAC CTTCCTGTTG      60

GGCATCATCC CACCTTCCCA GAGCCCTGGA GAGCATGGGG AGACCCGGGA CCCTGCTGGG    120

TTTCTCTGTC ACAAAGGAAA ATAATCCCCC TGGTGTGACA GACCCAAGGA CAGAACACAG    180

CAGAGGTCAG CACTGGGGAA GACAGGTTGT CCTCCCAGGG GATGGGGGTC CATCCACCTT    240

GCCGAAAAGA TTTGTCTGAG GAACTGAAAA TAGAAGGGAA AAAAGAGGAG GGACAAAAGA    300

GGCAGAAATG AGAGGGGAGG GGACAGAGGA CACCTGAATA AAGACCACAC CCATGACCCA    360

CGTGATGCTG AGAAGTACTC CTGCCCTAGG AAGAGACTCA GGGCAGAGGG AGGAAGGACA    420

GCAGACCAGA CAGTCACAGC AGCCTTGACA AAACGTTCCT GGAACTCAAG CA            472

(2) INFORMATION FOR SEQ ID NO:8:

(i) SEQUENCE CHARACTERISTICS:
        (A) LENGTH: 858 base pairs
        (B) TYPE: nucleic acid
```

(C) STRANDEDNESS: single
        (D) TOPOLOGY: linear (xi) SEQUENCE DESCRIPTION: SEQ ID NO:8:

CGAGCGGCCC CTCAGCTTCG GCGCCCAGCC CCGCAAGGCT CCCGGTGACC ACTAGAGGGC    60

GGGAGGAGCT CCTGGCCAGT GGTGGAGAGT GGCAAGGAAG GACCCTAGGG TTCATCGGAG   120

CCCAGGTTTA CTCCCTTAAG TGGAAATTTC TTCCCCCACT CCTCCTTGGC TTTCTCCAAG   180

GAGGGAACCC AGGCTGCTGG AAAGTCCGGC TGGGGCGGGG ACTGTGGGTT CAGGGGAGAA   240

CGGGGTGTGG AACGGGACAG GGAGCGGTTA GAAGGGTGGG GCTATTCCGG GAAGTGGTGG   300

GGGGAGGGAG CCCAAAACTA GCACCTAGTC CACTCATTAT CCAGCCCTCT TATTTCTCGG   360

CCGCTCTGCT TCAGTGGACC CGGGGAGGGC GGGGAAGTGG AGTGGGAGAC CTAGGGGTGG   420

GCTTCCCGAC CTTGCTGTAC AGGACCTCGA CCTAGCTGGC TTTGTTCCCC ATCCCCACGT   480

TAGTTGTTGC CCTGAGGCTA AAACTAGAGC CCAGGGGCCC CAAGTTCCAG ACTGCCCCTC   540

CCCCCTCCCC CGGAGCCAGG GAGTGGTTGG TGAAAGGGGG AGGCCAGCTG GAGAACAAAC   600

GGGTAGTCAG GGGGTTGAGC GATTAGAGCC CTTGTACCCT ACCCAGGAAT GGTTGGGGAG   660

GAGGAGGAAG AGGTAGGAGG TAGGGGAGGG GGCGGGGTTT TGTCACCTGT CACCTGCTCG   720

CTGTGCCTAG GGCGGGCGGG CGGGGAGTGG GGGGACCGGT ATAAAGCGGT AGGCGCCTGT   780

GCCCGCTCCA CCTCTCAAGC AGCCAGCGCC TGCCTGAATC TGTTCTGCCC CCTCCCCACC   840

CATTTCACCA CCACCATG                                                858

(2) INFORMATION FOR SEQ ID NO:9:

(i) SEQUENCE CHARACTERISTICS:
        (A) LENGTH: 307 base pairs
        (B) TYPE: nucleic acid
        (C) STRANDEDNESS: single
        (D) TOPOLOGY: linear (ix) FEATURE:
        (A) NAME/KEY: Coding Sequence
        (B) LOCATION: 2...304
        (D) OTHER INFORMATION:

(xi) SEQUENCE DESCRIPTION: SEQ ID NO:9:

G ATG ACC GGC TCA ACC ATC GCG CCC ACA ACG GAC TAT CGC AAC ACC ACT    49
  Met Thr Gly Ser Thr Ile Ala Pro Thr Thr Asp Tyr Arg Asn Thr Thr
  1               5                   10                  15

GCT ACC GGA CTA ACA TCT GCC CTA AAT TTA CCC CAA GTT CAT GCC TTT      97
Ala Thr Gly Leu Thr Ser Ala Leu Asn Leu Pro Gln Val His Ala Phe
            20                  25                  30

GTC AAT GAC TGG GCG AGC TTG GAC ATG TGG TGG TTT TCC ATA GCG CTT     145
Val Asn Asp Trp Ala Ser Leu Asp Met Trp Trp Phe Ser Ile Ala Leu
        35                  40                  45

ATG TTT GTT TGC CTT ATT ATT ATG TGG CTT ATT TGT TGC CTA AAG CGC     193
Met Phe Val Cys Leu Ile Ile Met Trp Leu Ile Cys Cys Leu Lys Arg
50                  55                  60

AGA CGC GCC AGA CCC CCC ATC TAT AGG CCT ATC ATT GTG CTC AAC CCA     241
Arg Arg Ala Arg Pro Pro Ile Tyr Arg Pro Ile Ile Val Leu Asn Pro
65                  70                  75                  80

CAC AAT GAA AAA ATT CAT AGA TTG GAC GGT CTG AAA CCA TGT TCT CTT     289
His Asn Glu Lys Ile His Arg Leu Asp Gly Leu Lys Pro Cys Ser Leu
                85                  90                  95

CTT TTA CAG TAT GAT TAA                                             307
Leu Leu Gln Tyr Asp
            100

(2) INFORMATION FOR SEQ ID NO:10:

(i) SEQUENCE CHARACTERISTICS:
        (A) LENGTH: 101 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:10:

```
Met Thr Gly Ser Thr Ile Ala Pro Thr Thr Asp Tyr Arg Asn Thr Thr
 1               5                  10                  15

Ala Thr Gly Leu Thr Ser Ala Leu Asn Leu Pro Gln Val His Ala Phe
            20                  25                  30

Val Asn Asp Trp Ala Ser Leu Asp Met Trp Trp Phe Ser Ile Ala Leu
        35                  40                  45

Met Phe Val Cys Leu Ile Ile Met Trp Leu Ile Cys Cys Leu Lys Arg
    50                  55                  60

Arg Arg Ala Arg Pro Pro Ile Tyr Arg Pro Ile Ile Val Leu Asn Pro
65                  70                  75                  80

His Asn Glu Lys Ile His Arg Leu Asp Gly Leu Lys Pro Cys Ser Leu
                85                  90                  95

Leu Leu Gln Tyr Asp
           100
```

(2) INFORMATION FOR SEQ ID NO:11:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:11:

GATCACCGGT GTCCACGGCC AGGTGGTGC                    29

(2) INFORMATION FOR SEQ ID NO:12:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:12:

GATCACCGGT GCTCACGCCT GTAATCTCAT CAC              33

(2) INFORMATION FOR SEQ ID NO:13:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:13:

GATCACCGGT GGTTTGGGAT GGCATGGCTT TGG              33

(2) INFORMATION FOR SEQ ID NO:14:

(i) SEQUENCE CHARACTERISTICS:

(A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:14:

GATCACCGGT AAAGAATCAG TGATCATCCC AAC                33

(2) INFORMATION FOR SEQ ID NO:15:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:15:

GATCCGGCCG TGGTGCTCAC GCCTGTAATC                30

(2) INFORMATION FOR SEQ ID NO:16:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO:16:

GATCCGGCCG TGTCCACGGC CAGGTGGTGC AG                32

(2) INFORMATION FOR SEQ ID NO:17:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:17:

CTCATTTTCA GTCACCGGTA AGCTTGG                27

(2) INFORMATION FOR SEQ ID NO:18:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:18:

GAGCCGCTCC GACACCGGTA CCTC                24

(2) INFORMATION FOR SEQ ID NO:19:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO:19:

GATCACCGGT AAGCTTCCAC AAGTGCATTT AGCC                34

(2) INFORMATION FOR SEQ ID NO:20:

(i) SEQUENCE CHARACTERISTICS:
        (A) LENGTH: 33 base pairs (B) TYPE: nucleic acid
            (C) STRANDEDNESS: single
            (D) TOPOLOGY: linear (xi) SEQUENCE DESCRIPTION: SEQ ID NO:20:

GATCACCGGT CTGTAGGTAT CTGGACCTCA CTG                          33

(2) INFORMATION FOR SEQ ID NO:21:

(i) SEQUENCE CHARACTERISTICS:
            (A) LENGTH: 34 base pairs
            (B) TYPE: nucleic acid
            (C) STRANDEDNESS: single
            (D) TOPOLOGY: linear (xi) SEQUENCE DESCRIPTION: SEQ ID NO:21:

GATCCGGCCG AAGCTTCCAC AAGTGCATTT AGCC                         34

(2) INFORMATION FOR SEQ ID NO:22:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (xi) SEQUENCE DESCRIPTION: SEQ ID NO:22:

GATCCGGCCG CTGTAGGTAT CTGGACCTCA CTG                          33

(2) INFORMATION FOR SEQ ID NO:23:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (xi) SEQUENCE DESCRIPTION: SEQ ID NO:23:

GTGACCGGTG CATTGCTGTG AACTCTGTA                               29

(2) INFORMATION FOR SEQ ID NO:24:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (xi) SEQUENCE DESCRIPTION: SEQ ID NO:24:

ATAAGTGGCC TGGATAAAGC TGAGTGG                                 27

(2) INFORMATION FOR SEQ ID NO:25:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (xi) SEQUENCE DESCRIPTION: SEQ ID NO:25:

GTCACCGGTC TTTGTTATTG GCAGTGGT                                28

(2) INFORMATION FOR SEQ ID NO:26:

(i) SEQUENCE CHARACTERISTICS:
            (A) LENGTH: 30 base pairs
            (B) TYPE: nucleic acid

```
        (C) STRANDEDNESS: single
        (D) TOPOLOGY: linear (xi) SEQUENCE DESCRIPTION: SEQ ID NO:26:

ATCCAGGCCA CTTATGAGCT CTGTGTCCTT                                            30

(2) INFORMATION FOR SEQ ID NO:27:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:27:

TATCGGCCGG CATTGCTGTG AACTCT                                                26

(2) INFORMATION FOR SEQ ID NO:28:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:28:

TTACGGCCGC TTTGTTATTG GCAGTG                                                26

(2) INFORMATION FOR SEQ ID NO:29:

(i) SEQUENCE CHARACTERISTICS:
        (A) LENGTH: 786 base pairs
        (B) TYPE: nucleic acid
        (C) STRANDEDNESS: single
        (D) TOPOLOGY: linear (xi) SEQUENCE DESCRIPTION: SEQ ID NO:29:

CGGTGACCAC TAGAGGGCGG GAGGAGCTCC TGGCCAGTGG TGGAGAGTGG CAAGGAAGGA            60

CCCTAGGGTT CATCGGAGCC CAGGTTTACT CCCTTAAGTG GAAATTTCTT CCCCCACTCC           120

TCCTTGGCTT TCTCCAAGGA GGGAACCCAG GCTGCTGGAA AGTCCGGCTG GGGCGGGGAC           180

TGTGGGTTCA GGGGAGAACG GGGTGTGGAA CGGGACAGGG AGCGGTTAGA AGGGTGGGGC           240

TATTCCGGGA AGTGGTGGGG GGAGGGAGCC CAAAACTAGC ACCTAGTCCA CTCATTATCC           300

AGCCCTCTTA TTTCTCGGCC GCTCTGCTTC AGTGGACCCG GGAGGGCGG GGAAGTGGAG            360

TGGGAGACCT AGGGGTGGGC TTCCCGACCT TGCTGTACAG GACCTCGACC TAGCTGGCTT           420

TGTTCCCCAT CCCCACGTTA GTTGTTGCCC TGAGGCTAAA ACTAGAGCCC AGGGGCCCCA           480

AGTTCCAGAC TGCCCCTCCC CCCTCCCCCG GAGCCAGGGA GTGGTTGGTG AAAGGGGGAG           540

GCCAGCTGGA GAACAAACGG GTAGTCAGGG GGTTGAGCGA TTAGAGCCCT TGTACCCTAC           600

CCAGGAATGG TTGGGGAGGA GGAGGAAGAG GTAGGAGGTA GGGGAGGGGG CGGGGTTTTG           660

TCACCTGTCA CCTGCTCGCT GTGCCTAGGG CGGGCGGGCG GGGAGTGGGG GGACCGGTAT           720

AAAGCGGTAG CGCCTGTGC CCGCTCCACC TCTCAAGCAG CCAGCGCCTG CCTGAATCTG            780

TTCTGC                                                                     786

(2) INFORMATION FOR SEQ ID NO:30:

(i) SEQUENCE CHARACTERISTICS:
        (A) LENGTH: 26 base pairs
        (B) TYPE: nucleic acid
        (C) STRANDEDNESS: single
```

(D) TOPOLOGY: linear (xi) SEQUENCE DESCRIPTION: SEQ ID NO:30:

TAATCCGGAC GGTGACCACT AGAGGG                                        26

(2) INFORMATION FOR SEQ ID NO:31:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:31:

TATTCCGGAT CACTTAGGCA GCGCTG                                        26

(2) INFORMATION FOR SEQ ID NO:32:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:32:

TAACGGCCGC GGTGACCACT AGAG                                          24

(2) INFORMATION FOR SEQ ID NO:33:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:33:

TATCGGCCGG CAGAACAGAT TCAG                                          24

(2) INFORMATION FOR SEQ ID NO:34:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:34:

ATTACCGGTA GCCACCACCC AGTGAG                                        26

(2) INFORMATION FOR SEQ ID NO:35:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:35:

TAGACCGGTG CTTGAGTTCC AGGAAC                                        26

(2) INFORMATION FOR SEQ ID NO:36:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:36:

TAACGGCCGA GCCACCACCC A                                              21

(2) INFORMATION FOR SEQ ID NO:37:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:37:

TATCGGCCGG CTTGAGTTCC AGG                                            23

(2) INFORMATION FOR SEQ ID NO:38:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:38:

GCCTTAATTA AAAGCAAACC TCACCTCCG                                      29

(2) INFORMATION FOR SEQ ID NO:39:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:39:

GTGGAACAAA AGGTGATTAA AAAATCCCAG                                     30

(2) INFORMATION FOR SEQ ID NO:40:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:40:

CACCTTTTGT TCCACCGCTC TGCTTATTAC                                     30

(2) INFORMATION FOR SEQ ID NO:41:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:41:

GGCTTAATTA ACTGTGAAAG GTGGGAGC                                       28